(12) United States Patent
Konofagou et al.

(10) Patent No.: US 10,166,379 B2
(45) Date of Patent: *Jan. 1, 2019

(54) SYSTEMS AND METHODS FOR OPENING OF A TISSUE BARRIER

(71) Applicant: THE TRUSTEES OF COLUMBIA UNIVERSITY IN THE CITY OF NEW YORK, New York, NY (US)

(72) Inventors: Elisa E. Konofagou, New York, NY (US); James J. Choi, Englewood, NJ (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/165,942

(22) Filed: May 26, 2016

(65) Prior Publication Data
US 2016/0346526 A1 Dec. 1, 2016

Related U.S. Application Data

(63) Continuation of application No. 13/426,400, filed on Mar. 21, 2012, now Pat. No. 9,358,023, which is a
(Continued)

(51) Int. Cl.
*A61M 37/00* (2006.01)
*A61B 17/225* (2006.01)
(Continued)

(52) U.S. Cl.
CPC ....... *A61M 37/0092* (2013.01); *A61B 5/0071* (2013.01); *A61B 5/055* (2013.01);
(Continued)

(58) Field of Classification Search
CPC .............. A61M 37/0092; A61M 37/00; A61B 8/0808; A61B 2017/22005; A61B 2017/22008; A61B 8/08
See application file for complete search history.

(56) References Cited

U.S. PATENT DOCUMENTS

| | | | |
|---|---|---|---|
| 3,598,111 A | 8/1971 | Kahn | |
| 4,463,608 A | 8/1984 | Takeuchi et al. | |

(Continued)

FOREIGN PATENT DOCUMENTS

| | | |
|---|---|---|
| EP | 0 221 409 | 5/1987 |
| EP | 0 627 206 | 12/1994 |

(Continued)

OTHER PUBLICATIONS

U.S. Appl. No. 11/433,510 (U.S. Pat. No. 8,858,441), filed May 12, 2006 (Oct. 14, 2014).

(Continued)

*Primary Examiner* — Laura Bouchelle
(74) *Attorney, Agent, or Firm* — Baker Botts L.L.P.

(57) ABSTRACT

Systems and methods for opening a tissue to a target value using microbubbles are disclosed herein. In an embodiment of a method for opening a tissue to a target value using microbubbles, a region of the tissue is targeted for opening, an acoustic parameter corresponding to the target value is determined, and an ultrasound beam is applied to the target region at the acoustic parameter such that the tissue at the target region is opened to the target value with the microbubbles. The acoustic parameter can be selected to control an acoustic cavitation event and, in some embodiments, controlling an acoustic cavitation event can include controlling a location, number and/or magnitude of acoustic cavitation events.

30 Claims, 32 Drawing Sheets

Related U.S. Application Data continuation-in-part of application No. PCT/US2010/049681, filed on Sep. 21, 2010.

(60) Provisional application No. 61/353,611, filed on Jun. 10, 2010, provisional application No. 61/353,631, filed on Jun. 10, 2010, provisional application No. 61/244,311, filed on Sep. 21, 2009.

(51) Int. Cl.
  *A61B 8/08* (2006.01)
  *A61B 5/00* (2006.01)
  *A61B 5/055* (2006.01)

(52) U.S. Cl.
  CPC ............ *A61B 8/0808* (2013.01); *A61B 8/481* (2013.01); *A61B 17/225* (2013.01); *A61B 8/0816* (2013.01); *A61M 2202/0007* (2013.01); *A61M 2205/0244* (2013.01); *A61M 2205/058* (2013.01); *A61M 2210/0693* (2013.01); *A61M 2210/12* (2013.01); *A61M 2250/00* (2013.01)

(56) References Cited

U.S. PATENT DOCUMENTS

| | | |
|---|---|---|
| 4,777,599 A | 10/1988 | Dorogi et al. |
| 4,832,941 A | 5/1989 | Berwing et al. |
| 4,858,613 A | 8/1989 | Fry et al. |
| 4,882,679 A | 11/1989 | Tuy et al. |
| 4,926,675 A | 5/1990 | Schohl et al. |
| 5,038,787 A | 8/1991 | Antich et al. |
| 5,107,837 A | 4/1992 | Ophir et al. |
| 5,178,147 A | 1/1993 | Ophir et al. |
| 5,309,914 A | 5/1994 | Ilnuma |
| 5,433,708 A | 7/1995 | Nichols et al. |
| 5,435,310 A | 7/1995 | Sheehan et al. |
| 5,457,754 A | 10/1995 | Han et al. |
| 5,601,084 A | 2/1997 | Sheehan et al. |
| 5,606,971 A | 3/1997 | Sarvazyan |
| 5,662,113 A | 9/1997 | Liu |
| 5,718,241 A | 2/1998 | Ben-Haim et al. |
| 5,722,411 A | 3/1998 | Suzuki et al. |
| 5,741,522 A | 4/1998 | Violante et al. |
| 5,752,515 A | 5/1998 | Jolesz et al. |
| 5,769,790 A | 6/1998 | Watkins et al. |
| 5,810,731 A | 9/1998 | Sarvazyan et al. |
| 5,840,028 A | 11/1998 | Chubachi et al. |
| 5,928,151 A | 7/1999 | Hossack et al. |
| 6,026,173 A | 2/2000 | Svenson et al. |
| 6,028,066 A | 2/2000 | Unger |
| 6,102,864 A | 8/2000 | Hatfield et al. |
| 6,102,865 A | 8/2000 | Hossack et al. |
| 6,106,465 A | 8/2000 | Napolitano et al. |
| 6,123,669 A | 9/2000 | Kanda et al. |
| 6,152,878 A | 11/2000 | Nachtomy et al. |
| 6,193,951 B1 | 2/2001 | Ottoboni et al. |
| 6,200,266 B1 | 3/2001 | Shokrollahi et al. |
| 6,241,675 B1 | 6/2001 | Smith et al. |
| 6,246,895 B1 | 6/2001 | Plews |
| 6,259,943 B1 | 7/2001 | Cosman et al. |
| 6,270,459 B1 | 8/2001 | Konofagou et al. |
| 6,309,355 B1 | 10/2001 | Cain et al. |
| 6,312,382 B1 | 11/2001 | Mucci et al. |
| 6,352,507 B1 | 3/2002 | Torp et al. |
| 6,413,216 B1 | 7/2002 | Cain et al. |
| 6,425,865 B1 | 7/2002 | Salcudean et al. |
| 6,425,867 B1 | 7/2002 | Vaezy et al. |
| 6,447,450 B1 | 9/2002 | Oldstad |
| 6,488,629 B1 | 12/2002 | Saetre et al. |
| 6,491,636 B2 | 12/2002 | Chenal et al. |
| 6,508,768 B1 | 1/2003 | Hall et al. |
| 6,514,221 B2 | 2/2003 | Hynynen et al. |
| 6,529,770 B1 | 3/2003 | Grimblatov |
| 6,537,217 B1 | 3/2003 | Bjaerum et al. |
| 6,537,221 B2 | 3/2003 | Criton et al. |
| 6,671,541 B2 | 12/2003 | Bishop et al. |
| 6,683,454 B2 | 1/2004 | Rehwald et al. |
| 6,685,641 B2 | 2/2004 | Liu et al. |
| 6,689,060 B2 | 2/2004 | Phelps et al. |
| 6,701,341 B1 | 3/2004 | Wu |
| 6,770,033 B1 | 8/2004 | Fink et al. |
| 6,775,400 B1 | 8/2004 | Zhao et al. |
| 6,875,176 B2 | 4/2005 | Mourad et al. |
| 6,936,151 B1 | 8/2005 | Lock et al. |
| 6,994,673 B2 | 2/2006 | Lysyansky et al. |
| 7,016,719 B2 | 3/2006 | Rudy et al. |
| 7,055,378 B2 | 6/2006 | Su et al. |
| 7,136,518 B2 | 11/2006 | Griffin et al. |
| 7,257,244 B2 | 8/2007 | Miga |
| 7,331,926 B2 | 2/2008 | Varghese et al. |
| 7,344,509 B2 | 3/2008 | Hynynen et al. |
| 7,421,101 B2 | 9/2008 | Georgescu et al. |
| 7,429,249 B1 | 9/2008 | Winder et al. |
| 7,449,306 B2 | 11/2008 | Elson et al. |
| 7,601,122 B2 | 10/2009 | Zagzebski et al. |
| 7,753,847 B2 | 7/2010 | Greenleaf et al. |
| 7,809,426 B2 | 10/2010 | Kim et al. |
| 7,896,821 B1 | 3/2011 | Magnin et al. |
| 8,029,444 B2 | 10/2011 | Pedrizzetti et al. |
| 8,208,709 B2 | 6/2012 | Ding et al. |
| 8,257,338 B2 | 9/2012 | Keenan et al. |
| 9,063,220 B2 | 6/2015 | Yoda et al. |
| 9,358,023 B2 * | 6/2016 | Konofagou .......... A61B 17/225 |
| 2002/0034757 A1 | 3/2002 | Cubicciotti |
| 2002/0038086 A1 | 3/2002 | Hynynen et al. |
| 2002/0039594 A1 | 4/2002 | Unger |
| 2002/0065461 A1 | 5/2002 | Cosman |
| 2002/0095081 A1 | 7/2002 | Vilsmeier |
| 2002/0151792 A1 | 10/2002 | Conston et al. |
| 2002/0169394 A1 | 11/2002 | Eppstein et al. |
| 2002/0169484 A1 | 11/2002 | Mathis et al. |
| 2002/0193784 A1 | 12/2002 | McHale et al. |
| 2003/0040675 A1 | 2/2003 | Sharrock |
| 2003/0097068 A1 | 5/2003 | Hossack et al. |
| 2003/0125621 A1 | 7/2003 | Drukker et al. |
| 2003/0171672 A1 | 9/2003 | Varghese et al. |
| 2003/0174890 A1 | 9/2003 | Yamauchi |
| 2003/0220556 A1 | 11/2003 | Porat et al. |
| 2003/0236466 A1 | 12/2003 | Tarjan et al. |
| 2004/0006266 A1 | 1/2004 | Ustuner et al. |
| 2004/0049134 A1 | 3/2004 | Tosaya et al. |
| 2004/0049232 A1 | 3/2004 | Ideker et al. |
| 2004/0054357 A1 | 3/2004 | O'Donnell |
| 2004/0059220 A1 | 3/2004 | Mourad et al. |
| 2004/0059224 A1 | 3/2004 | Varghese et al. |
| 2004/0092816 A1 | 5/2004 | Ossmann et al. |
| 2004/0097805 A1 | 5/2004 | Verard et al. |
| 2004/0116812 A1 | 6/2004 | Selzer et al. |
| 2004/0122320 A1 | 6/2004 | Murashita |
| 2004/0143189 A1 | 7/2004 | Lysyansky et al. |
| 2004/0167403 A1 | 8/2004 | Nightingale et al. |
| 2004/0172081 A1 | 9/2004 | Wang |
| 2004/0210134 A1 | 10/2004 | Hynynen et al. |
| 2004/0210135 A1 | 10/2004 | Hynynen |
| 2004/0234113 A1 | 11/2004 | Miga |
| 2004/0236219 A1 | 11/2004 | Liu et al. |
| 2004/0249580 A1 | 12/2004 | Pourcelot et al. |
| 2004/0258760 A1 | 12/2004 | Wheatley et al. |
| 2005/0004466 A1 | 1/2005 | Hynenen et al. |
| 2005/0026262 A1 | 2/2005 | Yoshitani et al. |
| 2005/0054930 A1 | 3/2005 | Rickets et al. |
| 2005/0059876 A1 | 3/2005 | Krishnan |
| 2005/0080336 A1 | 4/2005 | Byrd et al. |
| 2005/0080469 A1 | 4/2005 | Larson et al. |
| 2005/0084538 A1 | 4/2005 | Dayton et al. |
| 2005/0124892 A1 | 6/2005 | Weitzel et al. |
| 2005/0175541 A1 | 8/2005 | Lanza et al. |
| 2005/0201942 A1 | 9/2005 | Dugstad et al. |
| 2005/0203395 A1 | 9/2005 | Sui et al. |
| 2005/0203399 A1 | 9/2005 | Vaezy et al. |
| 2005/0259864 A1 | 11/2005 | Dickinson et al. |
| 2005/0267695 A1 | 12/2005 | German |
| 2005/0277824 A1 | 12/2005 | Aubry et al. |
| 2005/0277835 A1 | 12/2005 | Angelsen et al. |

(56) References Cited

U.S. PATENT DOCUMENTS

| | | |
|---|---|---|
| 2006/0034904 A1 | 2/2006 | Weimann |
| 2006/0058651 A1 | 3/2006 | Chiao et al. |
| 2006/0058671 A1 | 3/2006 | Vitek et al. |
| 2006/0058673 A1 | 3/2006 | Aase et al. |
| 2006/0074315 A1 | 4/2006 | Liang et al. |
| 2006/0078501 A1 | 4/2006 | Goertz et al. |
| 2006/0173320 A1 | 8/2006 | Radulescu |
| 2006/0241462 A1 | 10/2006 | Chou et al. |
| 2006/0241529 A1 | 10/2006 | Hynynen et al. |
| 2007/0049824 A1 | 3/2007 | Konofagou et al. |
| 2007/0055179 A1 | 3/2007 | Deem et al. |
| 2007/0059247 A1 | 3/2007 | Lindner et al. |
| 2007/0071683 A1 | 3/2007 | Dayton et al. |
| 2007/0129652 A1 | 6/2007 | Nita |
| 2007/0207194 A1 | 9/2007 | Grayburn et al. |
| 2007/0219447 A1 | 9/2007 | Kanai et al. |
| 2007/0232962 A1 | 10/2007 | Zumeris et al. |
| 2007/0239001 A1 | 10/2007 | Mehi et al. |
| 2007/0276242 A1 | 11/2007 | Konofagou et al. |
| 2007/0276245 A1 | 11/2007 | Konofagou et al. |
| 2007/0276254 A1 | 11/2007 | Konofagou |
| 2008/0089848 A1 | 4/2008 | DiMauro |
| 2008/0194957 A1 | 8/2008 | Hoctor et al. |
| 2008/0200417 A1 | 8/2008 | Semple et al. |
| 2008/0243214 A1 | 10/2008 | Koblish |
| 2008/0260802 A1 | 10/2008 | Sawhney et al. |
| 2008/0269606 A1 | 10/2008 | Matsumura |
| 2008/0269668 A1 | 10/2008 | Keenan et al. |
| 2008/0285819 A1 | 11/2008 | Konofagou et al. |
| 2008/0319355 A1 | 12/2008 | Nita |
| 2008/0319375 A1 | 12/2008 | Hardy |
| 2009/0005711 A1 | 1/2009 | Konofagou et al. |
| 2009/0191244 A1 | 7/2009 | Kheir et al. |
| 2009/0221916 A1 | 9/2009 | Konofagou et al. |
| 2009/0247911 A1 | 10/2009 | Novak et al. |
| 2009/0270790 A1 | 10/2009 | Raghavan |
| 2010/0049036 A1 | 2/2010 | Kimh |
| 2010/0056924 A1 | 3/2010 | Powers |
| 2010/0143241 A1 | 6/2010 | Johnson et al. |
| 2010/0286527 A1 | 11/2010 | Cannon et al. |
| 2011/0028854 A1 | 2/2011 | Addison et al. |
| 2011/0098562 A1 | 4/2011 | Salgo et al. |
| 2011/0177005 A1 | 7/2011 | Rapoport et al. |
| 2011/0208038 A1 | 8/2011 | Konofagou et al. |
| 2011/0295105 A1 | 12/2011 | Konofagou et al. |
| 2011/0313328 A1 | 12/2011 | Nita |
| 2012/0004693 A1 | 1/2012 | Lo et al. |
| 2012/0179073 A1 | 7/2012 | Nita |
| 2013/0038479 A1 | 2/2013 | Eldar et al. |
| 2013/0046229 A1 | 2/2013 | Konofagou et al. |
| 2013/0066211 A1 | 3/2013 | Konofagou et al. |
| 2013/0131495 A1 | 5/2013 | Konofagou et al. |
| 2013/0195313 A1 | 8/2013 | Gauthier et al. |
| 2013/0204166 A1 | 8/2013 | Villanueva et al. |
| 2013/0289398 A1 | 10/2013 | Borden et al. |
| 2013/0304407 A1 | 11/2013 | George et al. |
| 2013/0315491 A1 | 11/2013 | Konofagou et al. |
| 2014/0114216 A1 | 4/2014 | Konofagou et al. |
| 2016/0107002 A1 | 4/2016 | Nita |

FOREIGN PATENT DOCUMENTS

| | | |
|---|---|---|
| WO | WO 1999/037938 | 7/1999 |
| WO | WO 2005/030171 | 4/2005 |
| WO | WO 2007/148279 | 12/2007 |
| WO | WO 2008/015012 | 2/2008 |
| WO | WO 2008/027520 | 3/2008 |
| WO | WO 2008/062342 | 5/2008 |
| WO | WO 2008/131217 | 10/2008 |
| WO | WO 2008/131302 | 10/2008 |
| WO | WO 2008/157422 | 12/2008 |
| WO | WO 2010/030819 A1 | 3/2010 |
| WO | WO 2010/044385 | 4/2010 |
| WO | WO 2010/063951 | 6/2010 |
| WO | WO 2011/028690 | 3/2011 |
| WO | WO 2011/035312 | 3/2011 |

OTHER PUBLICATIONS

U.S. Appl. No. 11/697,573 (US 2007/0276245), filed Apr. 6, 2007 (Nov. 29, 2007).
U.S. Appl. No. 11/697,579 (US 2007/0276242), filed Apr. 6, 2007 (Nov. 29, 2007).
U.S. Appl. No. 11/899,004 (U.S. Pat. No. 8,150,128), filed Aug. 30, 2007 (Apr. 3, 2012).
U.S. Appl. No. 12/077,612 (US 2009/0005711), filed Mar. 19, 2008 (Jan. 1, 2009).
U.S. Appl. No. 12/096,254 (US 2009/0221916), filed Nov. 26, 2008 (Sep. 3, 2009).
U.S. Appl. No. 13/019,029 (U.S. Pat. No. 8,428,687), filed Feb. 1, 2011 (Apr. 23, 2013).
U.S. Appl. No. 13/045,070 (U.S. Pat. No. 9,302,124), filed Mar. 10, 2011 (Apr. 5, 2016).
U.S. Appl. No. 13/353,148 (US 2013/0066211), filed Jan. 18, 2012 (Mar. 14, 2013).
U.S. Appl. No. 13/426,400 (U.S. Pat. No. 9,358,023), filed Mar. 21, 2012 (Jun. 7, 2016).
U.S. Appl. No. 13/529,239 (US 2013/0131495), filed Jun. 21, 2012 (May 23, 2013).
U.S. Appl. No. 13/848,436 (US 2013/0315491), filed Mar. 21, 2013 (Nov. 28, 2013).
U.S. Appl. No. 14/091,010 (US 2014/0114216), filed Nov. 26, 2013 (Apr. 24, 2014).
U.S. Appl. No. 14/300,106 (U.S. Pat. No. 9,247,921), filed Jun. 9, 2014 (Feb. 2, 2016).
U.S. Appl. No. 14/457,023 (US 2015/0045724), filed Aug. 11, 2014 (Feb. 12, 2015).
U.S. Appl. No. 11/433,510, Mar. 30, 2012 Request for Continued Examination (RCE).
U.S. Appl. No. 11/433,510, Mar. 28, 2012 Advisory Action.
U.S. Appl. No. 11/433,510, Dec. 29, 2011 Response to Final Office Action.
U.S. Appl. No. 11/433,510, Sep. 30, 2011 Final Office Action.
U.S. Appl. No. 11/433,510, May 23, 2011 Response to Non-Final Office Action.
U.S. Appl. No. 11/433,510, Jan. 21, 2011 Non-Final Office Action.
U.S. Appl. No. 11/433,510, Oct. 28, 2010 Response to Non-Final Office Action.
U.S. Appl. No. 11/433,510, Apr. 28, 2010 Non-Final Office Action.
U.S. Appl. No. 11/433,510, Apr. 13, 2010 Amendment and Request for Continued Examination (RCE).
U.S. Appl. No. 11/433,510, Nov. 12, 2009 Final Office Action.
U.S. Appl. No. 11/433,510, Aug. 6, 2009 Response to Non-Final Office Action.
U.S. Appl. No. 11/433,510 Mar. 17, 2009 Non-Final Office Action.
U.S. Appl. No. 11/433,510, Jul. 23, 2014 Issue Fee Payment.
U.S. Appl. No. 11/433,510, Apr. 23, 2014 Notice of Allowance.
U.S. Appl. No. 11/433,510, Apr. 7, 2014 Applicant Initiated Interview Summary.
U.S. Appl. No. 11/433,510, Apr. 4, 2014 Response to Non-Final Office Action.
U.S. Appl. No. 11/433,510, Oct. 4, 2013 Non-Final Office Action.
U.S. Appl. No. 11/697,573, Jun. 16, 2014 Non-Final Office Action.
U.S. Appl. No. 11/697,573, Oct. 17, 2013 Final Office Action.
U.S. Appl. No. 11/697,573, Sep. 4, 2013 Response to Non-Final Office Action.
U.S. Appl. No. 11/697,573, May 10, 2013 Non-Final Office Action.
U.S. Appl. No. 11/697,573, Jan. 18, 2013 Amendment and Request for Continued Examination (RCE).
U.S. Appl. No. 11/697,573, Jul. 18, 2012 Final Office Action.
U.S. Appl. No. 11/697,573, Jun. 27, 2012 Response to Non-Final Office Action.
U.S. Appl. No. 11/697,573, Jan. 26, 2012 Non-Final Office Action.
U.S. Appl. No. 11/697,573, Aug. 18, 2011 Amendment and Request for Continued Examination (RCE).

(56) References Cited

OTHER PUBLICATIONS

U.S. Appl. No. 11/697,573, Mar. 18, 2011 Final Office Action.
U.S. Appl. No. 11/697,573, Dec. 22, 2010 Response to Non-Final Office Action.
U.S. Appl. No. 11/697,573, Jun. 23, 2010 Non-Final Office Action.
U.S. Appl. No. 11/697,573, Jan. 12, 2015 Notice of Abandonment.
U.S. Appl. No. 11/697,579, Nov. 28, 2011 Notice of Abandonment.
U.S. Appl. No. 11/697,579, Apr. 29, 2011 Final Office Action.
U.S. Appl. No. 11/697,579, Feb. 7, 2011 Response to Non-Final Office Action.
U.S. Appl. No. 11/697,579, Aug. 6, 2010 Non-Final Office Action.
U.S. Appl. No. 11/697,579, May 17, 2010 Response to Non-Final Office Action.
U.S. Appl. No. 11/697,579, Nov. 17, 2009 Non-Final Office Action.
U.S. Appl. No. 11/697,579, Oct. 15, 2009 Amendment and Request for Continued Examination (RCE).
U.S. Appl. No. 11/697,579, Jul. 15, 2009 Response to Final Office Action.
U.S. Appl. No. 11/697,579, Apr. 15, 2009 Final Office Action.
U.S. Appl. No. 11/697,579, Jan. 16, 2009 Response to Non-Final Office Action.
U.S. Appl. No. 11/697,579, Jul. 18, 2008 Non-Final Office Action.
U.S. Appl. No. 11/899,004, Jan. 3, 2012 Issue Fee payment.
U.S. Appl. No. 11/899,004, Nov. 3, 2011 Decision on Petition.
U.S. Appl. No. 11/899,004, Oct. 4, 2011 Petition and Amendment after Notice of Allowance.
U.S. Appl. No. 11/899,004, Oct. 3, 2011 Notice of Allowance.
U.S. Appl. No. 11/899,004, Sep. 23, 2011 Amendment and Request for Continued Examination (RCE).
U.S. Appl. No. 11/899,004, Sep. 19, 2011 Decision on Petition.
U.S. Appl. No. 11/899,004, Jul. 18, 2011 Notice of Allowance.
U.S. Appl. No. 11/899,004, May 10, 2011 Response to Non-Final Office Action.
U.S. Appl. No. 11/899,004, Feb. 8, 2011 Non-Final Office Action.
U.S. Appl. No. 12/077,612, Mar. 21, 2014 Final Office Action.
U.S. Appl. No. 12/077,612, Jan. 30, 2014 Response to Non-Final Office Action.
U.S. Appl. No. 12/077,612, Jan. 2, 2014 Applicant Initiated Interview Summary.
U.S. Appl. No. 12/077,612, Aug. 30, 2013 Non-Final Office Action.
U.S. Appl. No. 12/077,612, Oct. 26, 2011 Amendment and Request for Continued Examination (RCE).
U.S. Appl. No. 12/077,612, May 26, 2011 Final Office Action.
U.S. Appl. No. 12/077,612, Mar. 23, 2011 Response to Non-Final Office Action.
U.S. Appl. No. 12/077,612, Nov. 16, 2010 Non-Final Office Action.
U.S. Appl. No. 12/077,612, Sep. 22, 2014 Amendment and Request for Continued Examination (RCE).
U.S. Appl. No. 12/077,612, Oct. 29, 2015 Notice of Abandonment.
U.S. Appl. No. 12/077,612, Apr. 9, 2015 Non-Final Office Action.
U.S. Appl. No. 12/096,254, Mar. 21, 2014 Final Office Action.
U.S. Appl. No. 12/096,254, Dec. 23, 2013 Response to Non-Final Office Action.
U.S. Appl. No. 12/096,254, Dec. 17, 2013 Applicant Initiated Interview Summary.
U.S. Appl. No. 12/096,254, Aug. 23, 2013 Non-Final Office Action.
U.S. Appl. No. 12/096,254, Nov. 30, 2012 Amendment and Request for Continued Examination (RCE).
U.S. Appl. No. 12/096,254, May 31, 2012 Final Office Action.
U.S. Appl. No. 12/096,254, Apr. 4, 2012 Response to Non-Final Office Action.
U.S. Appl. No. 12/096,254, Oct. 5, 2011 Non-Final Office Action.
U.S. Appl. No. 12/096,254, Sep. 22, 2014 Amendment and Request for Continued Examination (RCE).
U.S. Appl. No. 12/096,254, Sep. 28, 2015 Notice of Abandonment.
U.S. Appl. No. 12/096,254, Feb. 27, 2015 Non-Final Office Action.
U.S. Appl. No. 13/019,029, Dec. 26, 2012 Notice of Allowance.
U.S. Appl. No. 13/019,029, Mar. 21, 2013 Issue Fee payment.
U.S. Appl. No. 13/045,070, Nov. 7, 2013 Amendment and Request for Continued Examination (RCE).
U.S. Appl. No. 13/045,070, May 9, 2013 Final Office Action.
U.S. Appl. No. 13/045,070, Dec. 21, 2012 Response to Non-Final Office Action.
U.S. Appl. No. 13/045,070, Jun. 22, 2012 Non-Final Office Action.
U.S. Appl. No. 13/045,070, Nov. 17, 2015 Response after Final Action.
U.S. Appl. No. 13/045,070, Jul. 7, 2015 Final Office Action.
U.S. Appl. No. 13/045,070, May 18, 2015 Applicant Initiated Interview Summary.
U.S. Appl. No. 13/045,070, May 15, 2015 Response to Non-Final Office Action.
U.S. Appl. No. 13/045,070, Jan. 16, 2015 Non-Final Office Action.
U.S. Appl. No. 13/045,070, Jan. 7, 2016 Notice of Appeal Filed.
U.S. Appl. No. 13/045,070, Jan. 15, 2016 Applicant Initiated Interview Summary.
U.S. Appl. No. 13/045,070, Jan. 15, 2016 Notice of Allowance.
U.S. Appl. No. 13/045,070, Feb. 24, 2016 Issue Fee Payment.
U.S. Appl. No. 13/353,148, Apr. 24, 2014 Non-Final Office Action.
U.S. Appl. No. 13/353,148, Oct. 17, 2013 Final Office Action.
U.S. Appl. No. 13/353,148, Sep. 11, 2013 Response to Non-Final Office Action.
U.S. Appl. No. 13/353,148, Jun. 20, 2013 Non-Final Office Action.
U.S. Appl. No. 13/353,148, Feb. 26, 2016 Notice of Abandonment.
U.S. Appl. No. 13/353,148, Aug. 12, 2015 Non-Final Office Action.
U.S. Appl. No. 13/353,148, Jul. 6, 2015 Amendment and Request for Continued Examination (RCE).
U.S. Appl. No. 13/353,148, Mar. 3, 2015 Final Office Action.
U.S. Appl. No. 13/353,148, Oct. 24, 2014 Response to Non-Final Office Action.
U.S. Appl. No. 13/353,148, Oct. 14, 2014 Applicant Initiated Interview Summary.
U.S. Appl. No. 13/353,148 Apr. 17, 2014 Amendment and Request for Continued Examination (RCE).
U.S. Appl. No. 13/353,148, Feb. 25, 2014 Applicant Initiated Interview Summary.
U.S. Appl. No. 13/426,400, May 13, 2016 Notice of Allowance.
U.S. Appl. No. 13/426,400, May 5, 2016 Issue Fee Payment.
U.S. Appl. No. 13/426,400, Feb. 5, 2016 Notice of Allowance.
U.S. Appl. No. 13/426,400, Dec. 4, 2015 Applicant Initiated Interview Summary.
U.S. Appl. No. 13/426,400, Dec. 4, 2015 Response to Non-Final Office Action.
U.S. Appl. No. 13/426,400, Jul. 2, 2015 Non-Final Office Action.
U.S. Appl. No. 13/426,400, Mar. 23, 2015 Amendment and Request for Continued Examination (RCE).
U.S. Appl. No. 13/426,400, Dec. 23, 2014 Final Office Action.
U.S. Appl. No. 13/426,400, Oct. 2, 2014 Response to Non-Final Office Action.
U.S. Appl. No. 13/426,400, May 5, 2014 Non-Final Office Action.
U.S. Appl. No. 13/529,239, Jun. 30, 2014 Amendment and Request for Continued Examination (RCE).
U.S. Appl. No. 13/529,239, Dec. 31, 2013 Final Office Action.
U.S. Appl. No. 13/529,239, Dec. 3, 2013 Response to Non-Final Office Action.
U.S. Appl. No. 13/529,239, Nov. 18, 2013 Applicant Initiated Interview Summary.
U.S. Appl. No. 13/529,239, Jul. 5, 2013 Non-Final Office Action.
U.S. Appl. No. 13/529,239, Sep. 3, 2014 Non-Final Office Action.
U.S. Appl. No. 13/529,239, Jun. 4, 2015 Final Office Action.
U.S. Appl. No. 13/529,239, Mar. 5, 2015 Applicant Initiated Interview Summary.
U.S. Appl. No. 13/529,239, Mar. 3, 2015 Response to Non-Final Office Action.
U.S. Appl. No. 13/529,239, May 1, 2014 Applicant Initiated Interview Summary.
U.S. Appl. No. 13/529,239, Jan. 8, 2016 Notice of Abandonment.
U.S. Appl. No. 13/848,436, Aug. 2, 2016 Notice of Allowance.
U.S. Appl. No. 13/848,436, Jun. 21, 2016 Response to Non-Final Office Action.
U.S. Appl. No. 13/848,436, Jan. 21, 2016 Non-Final Office Action.
U.S. Appl. No. 13/848,436, Dec. 21, 2015 Response to Restriction Requirement.

(56) References Cited

OTHER PUBLICATIONS

U.S. Appl. No. 13/848,436, Jul. 22, 2015 Restriction Requirement Filed.
U.S. Appl. No. 14/300,106, Dec. 22, 2015 Issue Fee Payment.
U.S. Appl. No. 14/300,106, Sep. 24, 2015 Notice of Allowance.
U.S. Appl. No. 14/457,023, Jun. 30, 2016 Response to Non-Final Office Action.
U.S. Appl. No. 14/457,023, Mar. 2, 2016 Non-Final Office Action.
"Vial", Retrieved from http://en.wikipedia.org/w/index.php?title=Vial&oldid=603936258 [Downloaded on May 20, 2014].
Abbott, et al., "Astrocyte-Endothelial Interactions At the Blood-Brain Barrier", Nat. Rev. Neurosci., 7(1):41-53 (2006).
Ammi, et al., "Ultrasonic contrast agent shell rupture detected by inertial cavitation and rebound signals", IEEE Transactions, 53(1):126-136 (2006).
Ashikaga, et al., "Transmural Dispersion of Myofiber Mechanics: Implications for Electrical Heterogeneity In Vivo", Journal of the American College of Cardiology, 49(8):909-916 (2007).
Aubry, et al., "Experimental Demonstration of Noninvasive Transskull Adaptive Focusing Based on Prior Computed Tomography Scans", The Journal of the Acoustical Society of America, 113:84 (2003).
Avolio, et al., "Effects of aging on changing arterial compliance and left ventricular load in a northern Chinese urban community", Circulation, 68(1):50-58 (1983).
Azuma, et al., "Bubble Generation by Standing Wave in Water Surrounded by Cranium With Transcranial Ultrasonic Beam", Japanese Journal of Applied Physics, 44:4625-4630 (2005).
Badke, et al., "Effects of Ventricular Pacing on Regional Left Ventricular Performance in the Dog", Am J Physiol Heart Circ Physiol., 238:H858-867 (1980).
Baron, et al., "Simulation of Intracranial Acoustic Fields in Clinical Trials of Sonothrombolysis", Ultrasound Med. Biol., 35(7):1148-1158 (2009).
Baseri, et al., "Multi-Modality Safety Assessment of Blood-Brain Barrier Opening Using Focused Ultrasound and Definity Microbubbles: A Short-Term Study", Ultrasound Med. Biol., 6(9):1445-1459 (2010).
Behrens, et al., "Low-Frequency, Low-Intensity Ultrasound Accelerates Thrombolysis Through the Skull", Ultrasound in Medicine & Biology, 25:269-273 (1999).
Bercoff, et al., "Supersonic Shear Imaging: A New Technique for Soft Tissue Elasticity Mapping", IEEE Transactions on Ultrasonics Ferroelectrics and Frequency Control, 51:396-409 (2004).
Berger, et al., "Single-Beat Noninvasive Imaging of Cardiac Electrophysiology of Ventricular Pre-Excitation", Journal of the American College of Cardiology, 48:2045-2052 (2006).
Bers, "Cardiac Excitation-Contraction Coupling", Nature ,415:198-205 (2002).
Bonnefous, et al, "Time Domain Formulation of Pulse-Doppler Ultrasound and Blood Velocity Estimation by Cross Correlation", Ultrason Imaging, 8(2):73-85 (1986).
Borden et al., "Ultrasound Radiation Force Modulates Ligand Availability on Target Contrast Agents", Mol. Imaging, 5:139-147 (2006).
Brekke, et al., "Tissue Doppler Gated (TDOG) Dynamic Three-Dimensional Ultrasound Imaging of the Fetal Heart", Ultrasound Obstet Gynecol., 24(2):192-198 (2004).
Brooks, et al., "Electrical Imaging of the Heart", IEEE Signal Processing Magazine, 14:24-42 (1997).
Brundin, et al., "Restorative Therapies in Parkinson's Disease", Springer Verlag (2006).
Campbell, et al., "Mechanisms of Transmurally Varying Myocyte Electromechanics in an Integrated Computational Model", Philos Transact A Math Phys Eng Sci., 366:3361-3380 (2008).
Carman, et al., "Adenosine receptor signaling modulates permeability of the blood-brain barrier", The Journal of Neuroscience, 31(37):13272-13280 (2011).
Caskey, et al., "Direct Observations of Ultrasound Microbubble Contrast Agent Interaction With the Microvessel Wall", J. Acoust. Soc. Amer., 122(2):1191-1200 (2007).
Caskey, et al., "Microbubble Oscillation in Tubes With Diameters of 12, 25, and 195 Microns", Appl. Phys. Lett., 88(3):033902-1-033902-3 (2006).
Cavaglia, et al., "Regional Variation in Brain Capillary Density and Vascular Response to Ischemia", Brain Res., 910(1-2):81-93 (2001).
Chan, "Transgenic Nonhuman Primates for Neurodegenerative Diseases", Reproductive Biology and Endocrinology, 2:39 (2004).
Chang, et al., "3-D US Frame Positioning Using Speckle Decorrelation and Image Registration", Ultrasound in Medicine and Biology, pp. 801-812 (2003).
Chen, et al., "The size of blood-brain barrier opening induced by focused ultrasound is dictated by the acoustic pressure", J. Cereb. Blood Flow Metab., 34:1197-1204 (2014).
Chen, et al., "Architectural Acoustics and Noise: Advancements and Best Practices in Instrumentation for Architectural Acoustics and Noise", J. Acoust. Soc. Am.; 164th Meeting: Acoustical Society of America, 132(3, Pt. 2):1977-2018 (Sep. 2012).
Chen, et al., "Engineering Acoustics and ASA Committee on Standards: Sound Intensity Measurements", J. Acoust. Soc. Am.; 164th Meeting: Acoustical Society of America, 132(3, Pt. 2):1984 (Sep. 2012).
Chen, et al., "Estimation of Displacement Vectors and Strain Tensors in Elastography Using Angular Insonifications", IEEE Transactions on Medical Imaging, 23(12):1479-1489 (2004).
Chen, et al., "Optimization of Ultrasound Parameters for Cardiac Gene Delivery of Adenoviral or Plasmid Deoxyribonucleic Acid by Ultrasound-Targeted Microbubble Destruction", J. Amer. Coll. Cardiol., 42(2):301-308 (2003).
Choi, et al., "Feasibility of Transcranial, Localized Drug-Delivery in the Brain of Alzheimer's-Model Mice Using Focused Ultrasound", 2005 IEEE Ultrasonics Symposium, pp. 988-991 (Sep. 18-21, 2005).
Choi, et al., "Microbubble-size dependence of focused ultrasound-induced blood-brain barrier opening in mice in vivo", IEEE transactions on Biomedical Engineering, 57(1):145-154 (2010).
Choi, et al., "Molecules of Various Pharmacologically-Relevant Sizes Can Cross the Ultrasound-Induced Blood-Brain Barrier Opening In Vivo", Ultrasound in Medicine & Biology, 36(1):58-67 (2009).
Choi, et al., "Noninvasive, Transcranial and Localized Opening of the Blood-Brain Barrier Using Focused Ultrasound in Mice", Ultrasound in Medicine & Biology, 33(1):95-104 (2007).
Choi, et al., "Spatio-Temporal Analysis of Molecular Delivery Through the Blood-Brain Barrier Using Focused Ultrasound", Physics in Medicine and Biology, 52:5509-5530, (2007).
Choi, et al., "Delivery of pharmacologically-relevant sized molecules through the ultrasound-induced blood-brain barrier opening in vivo", Neuroscience, Chicago, IL, USA, Oct. 17-21, 2009.
Choi, et al., "Focused Ultrasound-Induced Molecular Delivery Through the Blood-Brain Barrier", Presented at the IEEE Symp. Ultrason. Ferroelect. Freq. Control, New York, NY, pp. 1192-1195 (2007).
Choi, et al., "Noninvasive and Transient Blood-Brain Barrier Opening in the Hippocampus of Alzheimer's Double Transgenic Mice Using Pulsed Focused Ultrasound", Ultrasonic Imaging, pp. 189-200 (2008).
Choi, et al., "Optimization of Blood-Brain Barrier Opening in Mice using Focused Ultrasound", 2006 IEEE Ultrasounics Symposium [online], Jun. 2007.
Chomas, et al., "Threshold of Fragmentation for Ultrasonic Contrast Agents", J. Biomed. Opt., 6(2):141-150 (2001).
Clement, et al., "A Hemisphere Array for Non-Invasive Ultrasound Brain Therapy and Surgery", Phys Med Biol., 45:3707-3719 (2000).
Cobbold, R.S.C., "Foundations of biomedical ultrasound", Biomedical engineering series, Oxford University Press, pp. 422-423(2006).
Connor, "Simulation Methods and Tissue Property Models for Non-Invasive Transcranial Focused Ultrasound Surgery", Ph.D. Thesis (2005).
Connor, et al., "A Unified Model for the Speed of Sound in Cranial Bone Based on Genetic Algorithm Optimization", Physics in Medicine and Biology, 47:3925-3944 (2002).

(56) References Cited

OTHER PUBLICATIONS

Cordeiro, et al., "Transmural Heterogeneity of Calcium Activity and Mechanical Function in the Canine Left Ventricle", Am J Physiol. Heart Circ. Physiol., 286:H1471-1479 (2004).

Coyle, "Arterial Patterns of the Rat Rhinencephalon and Related Structures", Exp. Neurol., 49(3): 671-690 (1975).

Coyle, "Spatial Features of the Rat Hippocampal Vascular System", Exp. Neurol., 58(3): 549-561 (1978).

Coyle, "Vascular Patterns of the Rat Hippocampal Formation", Exp. Neurol., 52(3): 447-458 (1976).

Crum, et al., "Bjerknes Forces on Bubbles in a Stationary Sound Field", The Journal of the Acoustical Society of America, 57(6): 1363-1370 (1975).

Cutnell, et al., (1998). Physics, Fourth Edition. New York. Table of Contents.

Daffertshofer, et al., "Transcranial Low-Frequency Ultrasound-Mediated Thrombolysis in Brain Ischemia: Increased Risk of Hemorrhage With Combined Ultrasound and Tissue Plasminogen Activator: Results of a Phase II Clinical Trial", Stroke, 36:1441-146 (2005).

Damianou, et al., "Dependence of ultrasonic attenuation and absorption in dog soft tissues on temperature and thermal dose", J Acoust Soc Am, 102(1):628-634 (1997).

Datta, et al., "Correlation of Cavitation With Ultrasound Enhancement of Thrombolysis", Ultrasound in Medicine & Biology, 32(8): 1257-1267 (2006).

De Craene, et al., "Temporal diffeomorphic free-form deformation: Application to motion and strain estimation from 3D echocardiography", Medical Image Analysis, 16(2):427-450 (2012).

Declerck, et al., "Left ventricular motion reconstruction from planar tagged MR images: a comparison", Phys Med Biol., 45(6): 1611-1632 (2000).

Deffieux, et al., "Transcranial Focused Ultrasound for Blood-Brain Barrier Opening—Numerical Simulations With In Vitro Validation in Human and Monkey Skulls", Title page and Table of Contents for the AIUM Annual Convention, San Diego, CA, (2010).

Definition of "spatial filter" retrieved from http://ww.onelook.com/ on May 26, 2015.

DeLong, "Primate Models of Movement Disorders of Basal Ganglia Origin", Trends Neurosci., 13(7): 281-285 (1990).

DuBose, et al., "Confusion and Direction in Diagnostic Doppler Sonography", Journal of Diagnostic Medical Sonography, 25(3):173-177 (2009).

Duck, "Physical Properties of Tissue: A Comprehensive Reference Book", Academic Press, London, UK, 1990.

Duerinckx, et al., "In vivo acoustic attenuation in liver: correlations with blood tests and histology", Ultrasound Imaging, 14(5):405-413 (1988).

Durrer, et al., "Total Excitation of the Isolated Human Heart", Circulation, 41:899-912 (1970).

Edwards, et al., "Effects of Ischemia on Left-Ventricular Regional Function in the Conscious Dog", American Journal of Physiology, 240, H413-H420 (1981).

EPO Search Report and Opinion and Office Action for EP0684017.2 dated Dec. 7, 2009 and Mar. 8, 2010.

Epstein-Barasg, et al., "A microcomposite hydrogel for repeated on-demand ultrasound-triggered drug delivery", Biomaterials, 31(19):5208-5217 (2010).

Erpelding, et al., "Bubble-Based Acoustic Radiation Force Using Chirp Insonation to Reduce Standing Wave Effects", Ultrasound in Medicine & Biology, 33(2):263-269 (2007).

European Search Report for EP Application No. 10838238, dated May 6, 2014.

Everbach, et al., "Cavitational Mechanisms in Ultrasound-Accelerated Thrombolysis At 1 Mhz", Ultrasound in Medicine & Biology, 26(7): 1153-1160 (2000).

Faris, et al., "Novel Technique for Cardiac Electromechanical Mapping With Magnetic Resonance Imaging Tagging and an Epicardial Electrode Sock", Ann Biomed Eng., 31:430-440 (2003).

Farook, et al., "Preparation of Microbubble Suspensions by Co-Axial Electrohydrodynamic Atomization", Med. Eng. Phys., 29(7): 749-754 (2007).

Fenster, et al., "Three-dimensional ultrasound imaging", Phys Med Biol, 46(5):R67-R99 (2001).

Feshitan et al., "Microbubble Size Isolation by Differential Centrifugation", Journal of Colloid and Interface Science, 329: 316-324 (2009).

Fiske, et al., "Special Focus Section: Gene Therapy for Parkinson's Disease", Experimental Neurology, 209:28-29 (2008).

Fry, "Transkull Transmission of an Intense Focused Ultrasonic Beam", Ultrasound in Medicine & Biology, 3, p. 179 (1977).

Fry, et al., "A Focused Ultrasound System for Tissue Volume Ablation in Deep Seated Brain Sites", IEEE 1986 Ultrasonics Symposium, pp. 1001-1004 (1986).

Fujii, et al., "A new method for attenuation coefficient measurement in the liver", Journal of Ultrasound Medicine, 21(7):783-788 (2002).

Fung, (1993). Biomechanics—Mechanical Properties of Living Tissues. New York. Table of Contents.

Ganan-Calvo, et al., "Perfectly Monodisperse Microbubbling by Capillary Flow Focusing", Phys. Rev. Lett., 87(27) Pt 1: 274501-1-274501-4 (2001).

Gaud et al., "Acoustic Characterization of Single Ultrasound Contrast Agent Microbubbles", The Journal of the Acoustic Society of America, 124(6): 4091 (2008).

Ghosh, et al., "Cardiac Memory in Patients With Wolff-Parkinson-White Syndrome: Noninvasive Imaging of Activation and Repolarization Before and After Catheter Ablation", Circulation, 118:907-915 (2008).

Giacobini, "Alzheimer Disease, From Molecular Biology to Therapy", Advances in Experimental Medicine and Biology, 429:235-245 (1997).

Ginat, et al., "High-resolution ultrasound elastography of articular cartilage in vitro", Proceedings of the 28th IEEE EMBS Annual International Conference, New York City, USA, pp. 6644-6647 (Aug. 30-Sep. 3, 2006).

Greenstein, et al., "Mechanisms of Excitation-Contraction Coupling in an Integrative Model of the Cardiac Ventricular Myocyte", Biophysical Journal, 90:77-91 (2006).

Greenwald, "Pulse Pressure and Arterial Elasticity", Qjm-an International Journal of Medicine, 95(2): 107-112 (2002).

Gupta, et al., "Changes in Passive Mechanical Stiffness of Myocardial Tissue with Aneurysm Formation", Circulation, 89:2315-2326 (1994).

Gurev, et al., "Distribution of Electromechanical Delay in the Heart: Insights From a Three-Dimensional Electromechanical Model", Biophysical Journal, 99:745-754 (2010).

Gurev, et al., "In Silico Characterization of Ventricular Activation Pattern by Electromechanical Wave Imaging", Supplement to Heart Rhythm., 6:S357 (2009).

Heimdal, et al., "Real-time Strain Rate Imaging of the Left Ventricle by Ultrasound", J Am Soc EchocardioG., 11(11): 1013-1019 (1998).

Henderson, et al., "Series Elasticity of Heart Muscle During Hypoxia", Cardiovascular Research, 5:10-14 (1971).

Housden, et al., "Ultrasonic imaging of 3D displacement vectors using a simulated 2D array and beamsteering", Ultrasonics, 53(2):615-621 (2013).

Hsu, et al., "Noninvasive and targeted gene delivery into the brain using microbubble-facilitated focused ultrasound", PLoS One 8(2): e57682 (Feb. 2013).

Huang, et al. "Watershed Segmentation for Breast Tumor in 2-D Sonography", Ultrasound in Medicine and Biology, pp. 625-632 (2004).

Hynynen et al., "Local and reversible blood-brain barrier disruption by noninvasive focused ultrasound at frequencies suitable for transskull sonications" NeuroImage 24 (2005) 12-20.

Hynynen, et al., "Demonstration of Potential Noninvasive Ultrasound Brain Therapy Through an Intact Skull", Ultrasound in Medicine & Biology, 24(2): 275-283 (1998).

Hynynen, et al., "Noninvasive MR Imaging—Guided Focal Opening of the Blood-Brain Barrier in Rabbits", Radiology, 220(3): 640-646 (2001).

(56) References Cited

OTHER PUBLICATIONS

Hynynen, et al., "Trans-Skull Ultrasound Therapy: The Feasibility of Using Image-Derived Skull Thickness Information to Correct the Phase Distortion", IEEE Transactions on Ultrasonics, Ferroelectrics and Frequency Control, 46(3): 752-755, (1999).

Hynynen, et al., "Focal Disruption of the Blood-Brain Barrier Due to 260-Khz Ultrasound Bursts: A Method for Molecular Imaging and Targeted Drug Delivery", J. Neurosurg., 105(3): 445-454 (2006).

International Preliminary Report on Patentability, dated Apr. 17, 2007 and Written Opinion for PCT/US2005/037669, dated Jun. 13, 2006.

International Preliminary Report on Patentability, dated Apr. 17, 2007 and Written Opinion for PCT/US2005/037670, dated Nov. 22, 2006.

International Preliminary Report on Patentability, dated Jun. 11, 2008 and Written Opinion for PCT/US2006/061809, dated Oct. 4, 2007.

International Preliminary Report on Patentability, dated Nov. 14, 2007 and Written Opinion for PCT/US2006/018454, dated Aug. 9, 2007.

International Search Report and Written Opinion for PCT/US2006/036460, dated Sep. 5, 2007; International Preliminary Report dated Mar. 26, 2008.

International Search Report and Written Opinion for PCT/US2009/056513, dated Oct. 30, 2009.

International Search Report and Written Opinion for PCT/US2009/052563 dated Oct. 8, 2009.

International Search Report and Written Opinion for PCT/US2009/056565 dated Nov. 2, 2009.

International Search Report and Written Opinion for PCT/US2010/049681, dated Dec. 7, 2010.

International Search Report and Written Opinion for PCT/US2010/061742, dated Mar. 1, 2011.

International Search Report and Written Opinion for PCT/US2011/034704, dated Aug. 18, 2011.

International Search Report for PCT/US2007/019149 dated Feb. 29, 2008.

Jagannathan, et al., "High-Intensity Focused Ultrasound Surgery of the Brain: Part 1—A Historical Perspective With Modern Applications", Neurosurgery, 64(2): 201-211 (2009).

Jasaityte, et al., "Current state of three-dimensional myocardial strain estimation using echocardiography", J Am Soc Echocardiogr., 26(1):15-28 (2013).

Jensen, et al., "Calculation of Pressure Fields From Arbitrarily Shaped, Apodized, and Excited Ultrasound Transducers", IEEE Transactions on Ultrasonics, Ferroelectrics and Frequency Control, 39(2): 262-267 (1992).

Kallel, et al., "A Least-Squares Strain Estimator for Elastography", Ultrasonic Imaging, 19:195-208 (1997).

Kanai, et al. "Propagation of Spontaneously Actuated Pulsive Vibration in Human Heart Wall and In Vivo Viscoelasticity Estimation", IEEE Transactions on Ultrasonics, Ferroelectrics, and Frequency Control, 52(11): 1931-1942 (2005).

Kanai, et al., "A New Method for Measuring Small Local Vibrations in the Heart Using Ultrasound", IEEE Transactions on Biomedical Engineering, 40(12): 1233-1242 (1993).

Kanai, et al., "Myocardial Rapid Velocity Distribution", Ultrasound Med Biol., 27(4): 481-498 (2001).

Kanai, et al., "Transcutaneous Measurement of Frequency Dispersion in the Regional Pulse Wave Velocity", 2000 IEEE Ultrasonics Symposium, pp. 1-4 (2000).

Kaufman, et al., "Ultrasound Simulation in Bone", IEEE Transactions on Ultrasonics Ferroelectrics and Frequency Control, 55(6): 1205-1218 (2008).

Kawabata, et al., "Chemo-thermal approach for efficient ultrasonic tumor treatment with phase change nano droplet", IEEE Int. Ultrasonics Symp., Oct. 18-21, 2011 Orlando, Florida, pp. 9-12.

Kim, et al., "Multifunctional microbubbles and nanobubbles for photoacoustic and ultrasound imaging", J Biomed Opt., 15(1): 010510-1-010510-3 (Jan./Feb. 2010).

Kimber, et al., "A Comparison of Unipolar and Bipolar Electrodes During Cardiac Mapping Studies", Pacing Clin Electro., 19:1196-1204 (1996).

Kinoshita, et al., "Noninvasive Localized Delivery of Herceptin to the Mouse Brain by MRI-Guided Focused Ultrasound-Induced Blood-Brain Barrier Disruption", Proceedings of the National Academy of Sciences, 103(31): 11719-11723 (2006).

Kinoshita, et al., "Targeted Delivery of Antibodies Through the Blood-Brain Barrier by MRI-Guided Focused Ultrasound", Biochemical and Biophysical Research Communications, 340:1085-1090 (2006).

Klein, et al., "Interdependency of Local Capillary Density, Blood Flow, and Metabolism in Rat Brains", Amer. J. Physiol., 251(6) Pt 2: H1333-H1340 (1986).

Klempner, et al., "Neutrophil Plasma Membranes I. High-Yield Purification of Human Neutrophil Plasma Membrane Vesicles by Nitrogen Cavitation and Differential Centrifugation", Journal of Cell Biology, 86:21-28 (1980).

Konofagou et al., "Electromechanical Wave Imaging for Noninvasive Mapping of the 3D Electrical Activation Sequence in Canines and Humans In Vivo", Journal of Biomechanics, 45(5):856-864 (2012).

Konofagou, et al. "Elastographic Imaging of the Strain Distribution at the Anterior Cruciate Ligament and ACL-Bone Insertions", Proceedings of the 2005 IEEE 27th Annual International Conference of the Engineering in Medicine and Biology Society, pp. 972-975 (Shanghai, China Sep. 1-4, 2005).

Konofagou, et al., "Ultrasound-Induced Blood-Brain Barrier Opening", Current Pharmaceutical Biotechnology, 13(7): 1332-1345 (2012).

Konofagou, et al., "A New Elastographic Method for Estimation and Imaging of Lateral Strains, Corrected Axial Strains and Poison's Ratios in Tissues", Ultrasound in Medicine and Biology, 24(8):1183-1199 (1998).

Konofagou, et al., "Mechanism and Safety at the Threshold of the Blood-Brain Barrier Opening In Vivo", International Society on Therapeutic Ultrasound (ISTU), Aix-en-Provence, France, Sep. 21-24, 2009.

Konofagou, et al., "Myocardial Elastography—Feasibility Study In Vivo", Ultrasound Med & Biol., 28(4):475-482 (2002).

Konofagou, et al., "Noninvasive Electromechanical Wave Imaging and Conduction Velocity Estimation In Vivo", 2007 IEEE Ultrasonics Symposium, pp. 969-972 (2007).

Konofagou, et al., "Noninvasive electromechanical wave imaging and conduction-relevant velocity estimation in vivo", Ultrasonics, 50(2):208-215 (2010).

Konofagou, et al., "Three-Dimensional Motion Estimation in Elastography", IEEE Proceedings of the Symposium of Ultrasonics, Ferroelectrics and Frequency Control in Sendai, Japan, pp. 1745-1748 (1998).

Korecka, et al., "Cell-Replacement and Gene-Therapy Strategies for Parkinson's and Alzheimers Disease", Regen. Med., 2(4): 425-446 (2007).

Kremkau, et al., "Ultrasonic Attenuation and Propagation Speed in Normal Human Brain", The Journal of the Acoustical Society of America, 70:29 (1981).

Kunz, et al., "The Finite Difference Time Domain Method for Electromagnetics", CRC Press, Boca Raton, USA (1993).

Kvale, et al., "Size Fractionation of Gas-Filled Microspheres by Flotation", Separations Technol., 6(4): 219-226 (1996).

Lai, et al., "Introduction to Continuum Mechanics", (Pergamon Pr). 3rd Ed. (1993).

Lee, et al., "Improving Stereotactic Surgery Using 3-D Reconstruction", IEEE Engineering in Medicine and Biology Magazine, 21:109-116 (2002).

Lee, et al., "Theoretical Quality Assessment of Myocardial Elastography With In Vivo Validation", IEEE Transactions, Ultrasonics, Ferroelectrics and Frequency Control, 54:2233-2245 (2007).

Liu, et al., "Hemorrhage Detection During Focused-Ultrasound Induced Blood-Brain-Barrier Opening by Using Susceptibility-Weighted Magnetic Resonance Imaging", Ultrasound in Med. & Biol., 34(4): 598-606 (2008).

(56) References Cited

OTHER PUBLICATIONS

Liu, et al., "Magnetic Resonance Imaging Enhanced by Superparamagnetic Iron Oxide Particles: Usefulness for Distinguishing Between Focused Ultrasound-Induced Blood-Brain Barrier Disruption and Brain Hemorrhage", J. of Magnetic Resonance Imaging, 29:31-38 (2009).
Lu, et al., "Design and Experiment of 256-Element Ultrasound Phased Array for Noninvasive Focused Ultrasound Surgery", Ultrasonics, 44:e325-e330 (2006).
Luo, et al., "A Fast Normalized Cross-Correlation Method for Motion Estimation", IEEE Transactions, Ultrasonics, Ferroelectrics and Frequency Control, 57(6): 1347-1357 (2010).
Luo, et al., "High-Frame Rate, Full-View Myocardial Elastography With Automated Contour Tracking in Murine Left Ventricles In Vivo", IEEE Transactions, Ultrasonics, Ferroelectrics and Frequency Control, 55(1): 240-248 (2008).
Luo, et al., "Myocardial Elastography At Both High Temporal and Spatial Resolution for the Detection of Infarcts", Ultrasound Med. Biol., 33(8): 1206-1223 (2007).
Luo, et al., "Pulse Wave Imaging of Normal and Aneurysmal Abdominal Aortas In Vivo", IEEE Trans. Med. Imaging, 28(4): 477-486 (2009).
Maleke, et al., "In Vivo Feasibility of Real-Time Monitoring of Focused Ultrasound Surgery (FUS) Using Harmonic Motion Imaging (HMI)", IEEE Trans. Biomed. Eng., 57(1): 7-11 (2010).
Maleke, et al., "Single-Element Focused Ultrasound Transducer Method for Harmonic Motion Imaging", Ultrasonic Imaging, 28(3): 144-158 (2006).
Marquet, et al., "Non-Invasive Transcranial Ultrasound Therapy Based on a 3D CT Scan: Protocol Validation and In Vitro Results", Phys. Med. Biol., 54:2597-2613 (2009).
Mazziotta, et al., "A Probabilistic Atlas of the Human Brain: Theory and Rationale for Its Development the International Consortium for Brain Mapping (ICBM)", Neuroimage, 2:89-101 (1995).
McDannold, et al., "Targeted Disruption of the Blood-Brain Barrier With Focused Ultrasound: Association With Cavitations Activity", Physics in Medicine and Biology, 51:793-808 (2006).
McDannold, et al., "Use of Ultrasound Pulses Combined With Definity for Targeted Blood-Brain Barrier Disruption: A Feasibility Study", Ultrasound in Medicine & Biology, 33(4): 584-590 (2007).
McDannold, et al., "Blood-Brain Barrier Disruption Induced by Focused Ultrasound and Circulating Preformed Microbubbles Appears to be Characterized by the Mechanical Index", Ultrasound Med Biol., 34(5):834-840 (2008).
McDannold, et al., "MRI-Guided Targeted Blood-Brain Barrier Disruption With Focused Ultrasound: Histological Findings in Rabbits", Ultrasound Med. Biol., 31(11): 1527-1537 (2005).
McLaughlin, et al., "Piezoelectric Sensor Determination of Arterial Pulse Wave Velocity", Physiol Meas., 24(3): 693-702 (2003).
McNally, et al., "Computer Vision Elastography: Speckle Adaptive Motion Estimation for Elastography Using Ultrasound Sequences", IEEE Transactions on Medical Imaging, 24(6):755-766 (2005).
Melodelima, et al., "Thermal Ablation by High-Intensity-Focused Ultrasound Using a Toroid Transducer Increases the Coagulated Volume. Results of Animal Experiments", Ultrasound in Medicine & Biology, 35(3): 425-435 (2009).
Mitri, et al., "Chirp Imaging Vibro-Acoustography for Removing the Ultrasound Standing Wave Artifact", IEEE Transactions on Medical Imaging, 24(10): 1249-1255 (2005).
Mychaskiw, et al., "Optison (FS069) Disrupts the Blood-Brain Barrier in Rats", Anesthesia & Analgesia, 91:798 (2000).
Nichols, et al., "Vascular Impedance. In McDonald's: Blood Flow in Arteries: Theoretical, Experimental and Clinical Principles", E. Arnold. London, Oxford University Press, Table of Contents (1998).
Ohtani, et al., "Transmural Ultrasound-Based Visualization of Patterns of Action Potential Wave Propagation in Cardiac Tissue", Annals Biomedical Engineering, 38(10):3112-3123 (2010).
Ophir, et al., "Elastography: A Quantitative Method for Imaging the Elasticity of Biological Tissues", Ultrasonic Imaging, 3(2): 111-134 (1991).

Otani, "Use of ultrasound imaging to map propagating action potential waves in the heart", Computers in Cardiology, 36:617-620 (2009).
Palmeri, et al., "Characterizing acoustic attenuation of homogeneous media using focused impulsive acoustic radiation force", Ultrason Imaging, 28(2):114-128 (2006).
Papadakis, Emmauel P., "Ultrasonic Instruments & Devices", Academic Press, 8 pages (1999).
Pardridge, "Drug Targeting to the Brain", Pharmaceutical Research, 24:1733-1744 (2007).
Pardridge, "The Blood-Brain Barrier: Bottleneck in Brain Drug Development", NeuroRx, 2:3-14 (2005).
Patel, et al., "GDNF Delivery for Parkinson's Disease", ACTA Neurochirurgica—Supplementum, 97(2): 135-154 (2007).
Pernot, et al., "ECG-Gated, Mechanical and Electromechanical Wave Imaging of Cardiovascular Tissues In Vivo", Ultrasound in Medicine & Biology, 33(7):1075-1085 (2007).
Pernot, et al., "Electromechanical Imaging of the Myocardium at Normal and Pathological States", 2005 IEEE Ultrasonics Symposium, pp. 1091-1094 (2005).
Philippens, "Non-Human Primate Models for Parkinson's Disease", Drug Discovery Today: Disease Models, 5:105-111 (2008).
Pichardo, et al., "Multi Frequency Characterization of Speed of Sound for Longitudinal Transmission on Freshly Excised Human Skulls", 9th International Society on Therapeutic Ultrasound, p. 136 (2009.).
Prinzen, et al., "The Time Sequence of Electrical and Mechanical Activation During Spontaneous Beating and Ectopic Stimulation", Eur. Heart J., 13:535-543 (1992).
Provost, et al., "Electromechanical Wave Imaging of Normal and Ischemic Hearts In Vivo", IEEE Trans. Med. Imaging, 29:625-635 (2010).
Provost, et al., "Imaging the electromechanical activity of the heart in vivo", PNAS, 108(21):8565-8570 (2011).
Provost, et al., "Mapping of cardiac electrical activation with electromechanical wave imaging: An in silico-in vivo reciprocity study", Heart Rhythm., 8(5):752-759 (2011).
Qin, et al., "Acoustic Response of Compliable Microvessels Containing Ultrasound Contrast Agents", Phys. Med. Biol., 51:5065-5088 (2006).
Qin, et al., "The Natural Frequency of Nonlinear Oscillation of Ultrasound Contrast Agents in Microvessels", Ultrasound in Med. & Biol., 33(7):1140-1148 (2007).
Ramanathan, et al., "Activation and Repolarization of the Normal Human Heart Under Complete Physiological Conditions", Proceedings of the National Academy of Sciences, 103:6309-6314 (2006).
Ramanathan, et al., "Noninvasive Electrocardiographic Imaging for Cardiac Electrophysiology and Arrhythmia", Nat Med., 10:422-428 (2004).
Raymond, et al., "Ultrasound Enhanced Delivery of Molecular Imaging and Therapeutic Agents in Alzheimer's Disease Mouse Models", PLoS One, 3(5):e2175 (2008).
Rice, et al., "Approximate Model of Cooperative Activation and Crossbridge Cycling in Cardiac Muscle Using Ordinary Differential Equations", Biophys. J., 95:2368-2390 (2008).
Rockenstein, et al., "Transgenic Animal Models of Neurodegenerative Diseases and Their Application to Treatment Development", Adv. Drug Del. Rev., 59(11):1093-1102 (2007).
Rogers, et al., "Age-Associated Changes in Regional Aortic Pulse Wave Velocity", J Am Coll Cardiol., 38(4):1123-1129 (2001).
Roth, "Influence of a Perfusing Bath on the Foot of the Cardiac Action Potential", Circulation Research, 86:E19-E22 (2000).
Sabraoui, et al., "Feedback Loop Process to Control Acoustic Cavitation", Ultrasonics Sonochemistry, 18(2):589-594 (2011).
Samuel, et al., "An Ex Vivo Study of the Correlation Between Acoustic Emission and Microvascular Damage", Ultrasound Med. Biol., 35(9):1574-1586 (2009).
Sanberg, et al., "Brief Communication: Neural Transplants Disrupt the Blood-Brain Barrier and Allow Peripherally Acting Drugs to Exert a Centrally Mediated Behavioral Effect", Experimental Neurology, 102:149-152 (1988).
Sandrin, et al., "Time-Resolved Pulsed Elastography with Ultrafast Ultrasonic Imaging", Ultrason. Imaging, 21(4): 259-72 (1999).

(56) References Cited

OTHER PUBLICATIONS

Sarvazyan, et al., "Shear Wave Elasticity Imaging: A New Ultrasonic Technology of Medical Diagnostics", Ultrasound Med Biol., 24(9): 1419-1435 (1998).
Sassaroli, et al., "Cavitation Threshold of Microbubbles in Gel Tunnels by Focused Ultrasound", Ultrasound in Med. & Biol., 33(10):1651-1660 (2007).
Sassaroli, et al., "Forced Linear Oscillations of Microbubbles in Blood Capillaries", J. Acoust. Soc. Am., 115(6):3235-3243 (2004).
Sassaroli, et al., "Resonance Frequency of Microbubbles in Small Blood Vessels: a Numerical Study", Phys. Med. Biol., 50:5293-5305 (2005).
Schenk, et al., "Immunization With Amyloid-Beta Attenuates Alzheimer-Disease-Like Pathology in the PDAPP Mouse", Nature, 400:173-177 (1999).
Scher, et al., "The Pathway of Ventricular Depolarization in the Dog", Circ Res., 4:461-469 (1956).
Schilling, et al., "Simultaneous Endocardial Mapping in the Human Left Ventricle Using a Noncontact Catheter: Comparison of Contact and Reconstructed Electrograms During Sinus Rhythm", Circulation, 98:887-98 (1998).
Sengupta, et al., "Electromechanical Activation Sequence in Normal Heart", Heart Fail Clin., 4:303-314 (2008).
Shehata, et al., "Myocardial Tissue Tagging With Cardiovascular Magnetic Resonance", Journal of Cardiovascular Magnetic Resonance, 11:55 (2009).
Sheikov, et al., "Brain Arterioles Show More Active Vesicular Transport of Blood-Borne Tracer Molecules Than Capillaries and Venules After Focused Ultrasound-Evoked Opening of the Blood-Brain Barrier", Ultrasound Med. Biol., 32(9): 1399-1409 (2006).
Sheikov, et al., "Cellular Mechanisms of the Blood-Brain Barrier Opening Induced by Ultrasound in Presence of Microbubbles", Ultrasound Med. Biol., 30(7): 979-989 (2004).
Sheikov, et al., "Effect of Focused Ultrasound Applied With an Ultrasound Contrast Agent on the Tight Junctional Integrity of the Brain Microvascular Endothelium", Ultrasound Med. Biol., 34(7): 1093-1104 (2008).
Shinna, et al., "Realtime tissue elasticity imaging using the combined autocorrelation method", J. Med. Ultrasonics, 29(autumn):119-128 (2002).
Siegel, et al., "Neurotrophic Factors in Alzheimer's and Parkinson's Disease Brain", Brain Research Reviews, 33:199-227 (2000).
Silva, "Nanotechnology Approaches to Crossing the Blood-Brain Barrier and Drug Delivery to the CNS", BMC Neruosci., 9(Suppl 3): S4 (2008).
Sinkus, et al., "High-Resolution Tensor MR Elastography for Breast Tumour Detection", Phys Med Biol., 45(6): 1649-1664 (2000).
Sirsi, et al., "Effect of Microbubble Size on Fundamental Mode High Frequency Ultrasound Imaging in Mice", Ultrasound in Med. & Bio., 36(6): 935-948 (2010).
Spach, et al., "Extracellular Discontinuities in Cardiac Muscle—Evidence for Capillary Effects on the Action Potential Foot", Circulation Research, 83:1144-1164 (1998).
Stewart, et al., "Blood-Eye Barriers in the Rat: Correlation of Ultrastructure With Function", J. Comp. Neurol., 340(4): 566-576 (1994).
Stieger, et al., "Enhancement of Vascular Permeability With Low-Frequency Contrast-Enhanced Ultrasound in the Chorioallantoic Membrane Model", Radiology, 243(1): 112-121 (2007).
Styner, et al., "Automatic Brain Segmentation in Rhesus Monkeys", 2007 Medical Imaging, Proc. of SPIE, 6512:65122L-1-65122L-8 (2007).
Sutherland, "Color Doppler Myocardial Imaging—Potential Applications in Acquired and Congenital Heart-Disease", Acta Paediatr., 84:40-48 (1995).
Sykova, et al., "Diffusion in Brain Extracellular Space", Physiol. Rev., 88(4): 1277-1340 (2008).
Talu, et al., "Tailoring the Size Distribution of Ultrasound Contrast Agents: Possible Method for Improving Sensitivity in Molecular Imaging" Mol. Imag., 6(6): 384-392 (2007).

Tang, et al., "Standing-Wave Suppression for Transcranial Ultrasound by Random Modulation", IEEE transactions on Biomedical Engineering , 57(1):203-205 (2010).
Tanter, et al., "Focusing and Steering Through Absorbing and Aberrating Layers: Application to Ultrasonic Propagation Through the Skull", The Journal of the Acoustical Society of America, 103:2403-2410 (1998).
Tanter, et al., "Ultrafast Compound Imaging for 2-D Motion Vector Estimation: Application to Transient Elastography", IEEE Trans Ultrason Ferroelectr Freq Control, 49(10): 1363-74 (2002).
Tavarozzi, et al., "Magnetocardiography: Current Status and Perspectives Part II: Clinical Applications", Ital Heart J., 3:151-165 (2002).
Techavipoo, et al., "Temperature dependence of ultrasonic propagation speed and attenuation in excised canine liver tissue measured using transmitted and reflected pulses", The Journal of Acoustical Society of America, 115(6):2859-2865 (2004).
Treat, et al., "Targeted Delivery of Doxorubicin to the Rat Brain at Therapeutic Levels Using MRI-Guided Focused Ultrasound", Int. J. Cancer, 121(4): 901-907 (2007).
Tung, et al., "Feasibility of Noninvasive Cavitation-Guided Blood-Brain Barrier Opening Using Focused Ultrasound and Microbubbles in Nonhuman Primates", Applied Physics Letters, 98(16):163704 (2001).
Tung, et al., "Identifying the Inertial Cavitation Threshold and Skull Effects in a Vessel Phantom Using Focused Ultrasound and Microbubbles", Ultrasound in Medicine & Biology, 36(5): 840-852 (2010).
Tung, et al., "Identifying the Inertial Cavitation Threshold in a Vessel Phantom Using Focused Ultrasound and Microbubbles", The Journal of the Acoustical Society of America, 124:2486 (2008).
Tung, et al., "Noninvasive In Vivo Cavitation Threshold Detection During Blood-Brain Barrier Opening Using Focused Ultrasound and the Contrast Agent and Definity", Joint 159th Meeting of the Acoustic Society of America, (Apr. 19, 2010).
Tuszynski, et al., "A Phase 1 Clinical Trial of Nerve Growth Factor Gene Therapy for Alzheimer Disease", Nature Medicine, 11:551-555 (2005).
Tuszynski, et al., "Nerve Growth Factor Gene Therapy in Alzheimer Disease", Alzheimer Disease & Associated Disorders, 21:179-189 (2007).
Unger, E.C. et al., "Therapeutic Applications of Lipid-Coated Microbubbles", Advanced Drug Delivery Reviews, 56(9):1291-1314 (2004).
Vappou, et al., "Quantitative Viscoelastic Parameters Measured by Harmonic Motion Imaging", Phys. Med. Biol., 54:3579-3595 (2009).
Walker, et al., "A Fundamental Limit on Delay Estimation Using Partially Correlated Speckle Signals", IEEE Transactions, Ultrasonics, Ferroelectrics and Frequency Control, 42(2): 301-308 (1995).
Walker, et al., "A Fundamental Limit on the Performance of Correlation Based Phase Correction and Flow Estimation Techniques", IEEE Transactions, Ultrasonics, Ferroelectrics and Frequency Control, 41(5): 644-654 (1994).
Wang et al., "Qualitative and Quantitative Analysis of the Molecular Delivery Through the Ultrasound-Enhanced Blood-Brain Barrier Opening in the Murine Brain," presented at the IEEE Symp. Ultrason. Ferroelectr. Freq. Control, Beijing, China, 2008.
Wang, et al., "A Composite Imaging Technique for High Frame-Rate and Full-View Cardiovascular Ultrasound and Elasticity Imaging", IEEE Transactions, Ultrasonics, Ferroelectrics and Frequency Control, 55(10): 2221-2233 (2008).
Wang, et al., "A Composite Imaging Technique for High Frame-Rate and Full-View Cardiovascular Ultrasound and Elasticity Imaging", IEEE International Ultrasonics Symposium, New York, NY, Oct. 28-31, 2007.
Wang, et al., "Increased Aortic Stiffness Assessed by Pulse Wave Velocity in Apolipoprotein E-Deficient Mice", Am J Physiol Heart Circ Physiol., 278(2): H428-34 (2000).
Wenk, "A Primate Model of Alzheimer's Disease", Behavioural Brain Research, 57:117-122 (1993).
White, et al., "Longitudinal and Shear Mode Ultrasound Propagation in Human Skull Bone", Ultrasound in Medicine & Biology, 32:1085-1096 (2006).

(56) References Cited

OTHER PUBLICATIONS

Wyman, et al., "Mapping Propagation of Mechanical Activation in the Paced Heart With MRI Tagging", Am J Physiol Heart Circ Physiol, 276:H881-891 (1999).
Xu, et al., "Controllable Gas-Liquid Phase Flow Patterns and Monodisperse Microbubbles in a Microfluidic T-Junction Device", Appl. Phys. Lett., 88(13): 133506-1-133506-3 (2006).
Yin, et al., "A Numerical Study of Transcranial Focused Ultrasound Beam Propagation at Low Frequency", Physics in Medicine and Biology, 50:1821-1836 (2005).
Yuh, et. al. "Delivery of Systemic Chemotherapeutic Agent to Tumors by Using Focused Ultrasound: Study in a Murine Model", Radiology, 234(2): 431-437 (2005).
Zerhouni, et al., "Human Heart: Tagging with MR Imaging—A Method for Noninvasive Assessment of Myocardial Motion", Radiology, 169(1): 59-63 (1988).
Zhang, et al., "Noninvasive Three-Dimensional Electrocardiographic Imaging of Ventricular Activation Sequence", Am J Physiol Heart Circ Physiol., 289:H2724-32 (2005).
Zheng, et al. "High Resolution Ultrasound Elastomicroscopy Imaging of Soft Tissues: System Development and Feasibility; Ultrasound Elastomicroscopy", Physics in Medicine and Biology, 49(17):3925-3938 (2004).
Zheng, et al., "Ultrasonic measurement of depth-dependent transient behaviors of articular cartilage under compression", Journal of Biomechanics, 38:1830-1837 (2005).
Zheng, et al., "Ultrasound-Driven Microbubble Oscillation and Translation Within Small Phantom Vessels", Ultrasound Med. Biol., 33(12): 1978-1987 (2007).
Zlokovic, "The Blood-Brain Barrier in Health and Chronic Neurodegenerative Disorders", Neuron, 57(2): 178-201 (2008).
Zwanenburg, et al., "Timing of Cardiac Contraction in Humans Mapped by High-Temporal-Resolution MRI Tagging: Early Onset and Late Peak of Shortening in Lateral Wall", Am J Physiol Heart Circ Physiol., 286:H1872-1880 (2004).
U.S. Appl. No. 14/476,543 (US 2015/0065871), filed Sep. 3, 2014 (Mar. 5, 2015).
U.S. Appl. No. 14/949,000 (US 2016/0074678), filed Nov. 23, 2015 (Mar. 17, 2016).
Alam et al., "An Adaptive Strain Estimator for Elastography", IEEE Transactions on Ultrasonics, Ferroelectrics, and Frequency Control, vol. 45, No. 2, Mar. 1998, pp. 461-472.
Amin et al., "Therapy planning and monitoring of tissue ablation by high intensity focused ultrasound (HIFU) using imaging and simulation", Conf Proc IEEE Eng Med Biol Soc.2008,4471.
International Search Report and Written Opinion dated Jul. 17, 2012 in International Application No. PCT/US12/34136.
International Search Report and Written Opinion dated Oct. 18, 2012 in International Application No. PCT/US12/35685.
Liu et al., "Opening of the Blood-Brain Barrier by Low-Frequency (28-kHz) Ultrasound: A Novel Pinhole-Assisted Mechanical Scanning Device", Ultrasound in Med & Biol., vol. 36, Issue 2, Feb. 2010, pp. 325-335.
Long et al., "An integrated system for therapy planning of high intensity focused ultrasound", Electro/Information Technology, 2008. EIT 2008. IEEE International Conference on May 18-20, 2008, pp. 461-464.
Spalazzi et al., "Elastographic Imaging of Strain Distribution within the Anterior Cruciate Ligament and at the AGL-Bone Insertions", IEEE Ultrasonics Symposium, Sep. 2005, pp. 1755-1758.
Vaezy et al., "Real-time visualization of high-intensity focused ultrasound treatment using ultrasound imaging", Ultrasound Med Biol., Jan. 2001, 27(1), pp. 33-42.
Zheng et al., "A Targeting Method Based on Acoustic Backscatter for Treatment Planning in Tissue Ablation Using Focused Ultrasound", IEEE Trans on Biomed Eng. vol. 57, No. 1, Jan. 2010, pp. 71-79.
Ziadloo et al., "Real-time 3D image-guided HIFU therapy", Conf Proc IEEE Eng Med Biol Soc.2008,4459-62.
U.S. Appl. No. 13/848,436, Nov. 1, 2016 Issue Fee Payment.
U.S. Appl. No. 14/091,010, Sep. 12, 2016 Non-Final Office Action.
U.S. Appl. No. 14/457,023, Sep. 9, 2016 Final Office Action.
U.S. Appl. No. 14/476,543, Sep. 22, 2016 Non-Final Office Action.
Extended European Search Report dated Jan. 23, 2017 in EP Application No. 10818027.
U.S. Appl. No. 14/449,820 (US 2014/0343424), filed Aug. 1, 2014 (Nov. 20, 2014).
U.S. Appl. No. 14/682,980 (US 2015/0289840), filed Apr. 9, 2015 (Oct. 15, 2015).
U.S. Appl. No. 14/695,674 (US 2015/0297188), filed Apr. 24, 2015 (Oct. 22, 2015).
U.S. Appl. No. 15/048,761 (US 2016/0249880), filed Feb. 19, 2016 (Sep. 1, 2016).
U.S. Appl. No. 15/368,366 (US 2017/0148163), filed Dec. 2, 2016 (May 25, 2017).
U.S. Appl. No. 14/091,010, Jul. 3, 2018 Final Office Action.
U.S. Appl. No. 14/091,010, Mar. 13, 2017 Response to Non-Final Office Action.
U.S. Appl. No. 14/091,010, Apr. 20, 2017 Final Office Action.
U.S. Appl. No. 14/091,010, Oct. 18, 2017 Amendment and Request for Continued Examination (RCE).
U.S. Appl. No. 14/091,010, Dec. 1, 2017 Non-Final Office Action.
U.S. Appl. No. 14/091,010, Jun. 1, 2018 Response to Non-Final Office Action.
U.S. Appl. No. 14/449,820, Jul. 23, 2018 Final Office Action.
U.S. Appl. No. 14/449,820, Nov. 29, 2017 Response to Non-Final Office Action.
U.S. Appl. No. 14/449,820, Mar. 2, 2017 Non-Final Office Action.
U.S. Appl. No. 14/457,023, Mar. 9, 2017 Amendment and Request for Continued Examination (RCE).
U.S. Appl. No. 14/457,023, Jun. 23, 2017 Non-Final Office Action.
U.S. Appl. No. 14/457,023, Dec. 26, 2017 Response to Non-Final Office Action.
U.S. Appl. No. 14/457,023, May 2, 2018 Final Office Action.
U.S. Appl. No. 14/476,543, Jul. 17, 2017 Final Office Action.
U.S. Appl. No. 14/476,543, Mar. 22, 2017 Response to Non-Final Office Action.
U.S. Appl. No. 14/476,543, Jan. 17, 2018 Amendment and Request for Continued Examination (RCE).
U.S. Appl. No. 14/476,543, Mar. 22, 2018 Notice of Allowance.
U.S. Appl. No. 14/476,543, Jun. 22, 2018 Issue Fee Payment.
U.S. Appl. No. 14/682,980, Apr. 26, 2018 Advisory Action.
U.S. Appl. No. 14/682,980, Feb. 12, 2018 Notice of Appeal Filed.
U.S. Appl. No. 14/682,980, Jan. 10, 2018 Response after Final Action.
U.S. Appl. No. 14/682,980, Aug. 10, 2017 Final Office Action.
U.S. Appl. No. 14/682,980, May 1, 2017 Response to Non-Final Office Action.
U.S. Appl. No. 14/682,980, Dec. 1, 2016 Non-Final Office Action.
U.S. Appl. No. 14/695,674, Mar. 15, 2018 Final Office Action.
U.S. Appl. No. 14/695,674, Feb. 2, 2018 Response to Non-Final Office Action.
U.S. Appl. No. 14/695,674, Nov. 3, 2017 Non-Final Office Action.
U.S. Appl. No. 14/949,000, Jul. 28, 2017 Final Office Action.
U.S. Appl. No. 14/949,000, Jan. 29, 2018 Amendment and Request for Continued Examination (RCE).
U.S. Appl. No. 14/949,000, Feb. 28, 2018 Non-Final Office Action.
Sheeran et al., "Formulation and Acoustic Studies of a New Phase-Shift Agent for Diagnostic and Therapeutic Ultrasound," Langmuir, 27(17):10412-10420 (2011).

* cited by examiner

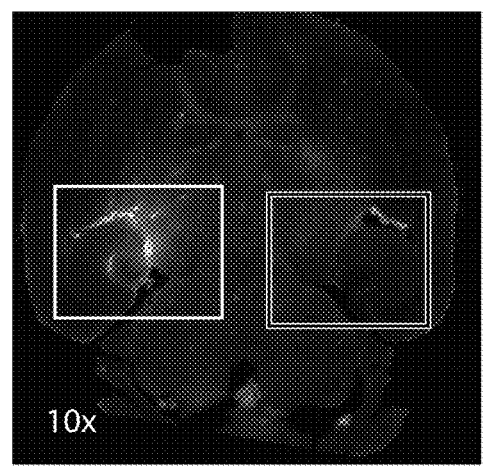
FIG. 6A
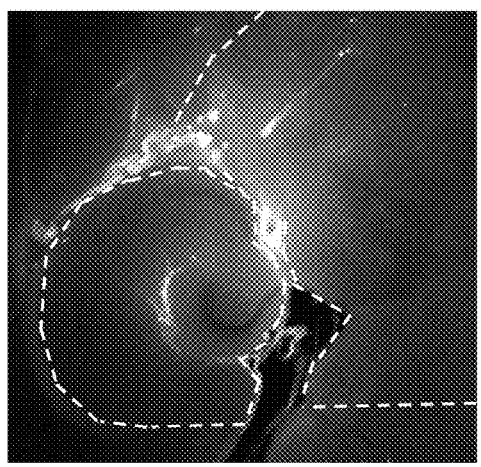    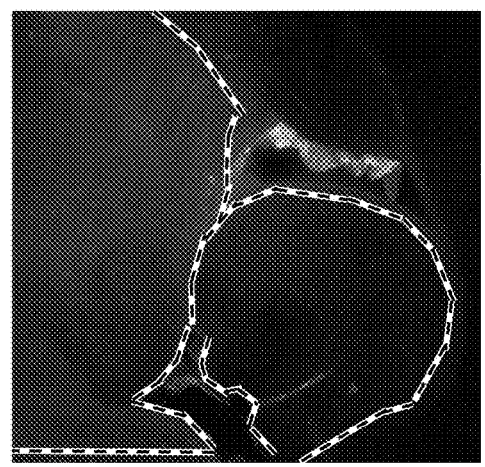
FIG. 6B    FIG. 6C

Left ROI 0.033 ms
(50 cycles)

Right ROI 0.033 ms
(50 cycles)

Left ROI 0.1 ms
(152 cycles)

Right ROI 0.1 ms
(152 cycles)

Left ROI 20 ms
(30400 cycles)

Right ROI 20 ms
(30400 cycles)

Left ROI 30 ms
(45600 cycles)

Right ROI 30 ms
(45600 cycles)

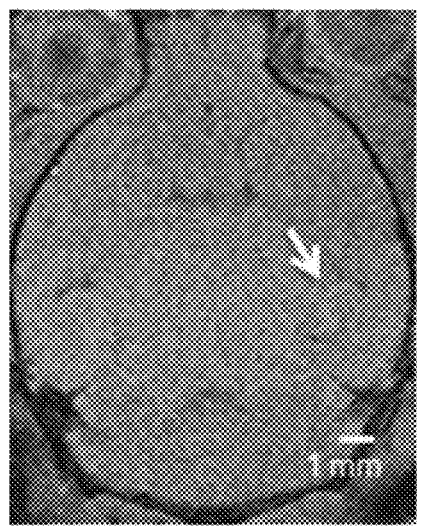 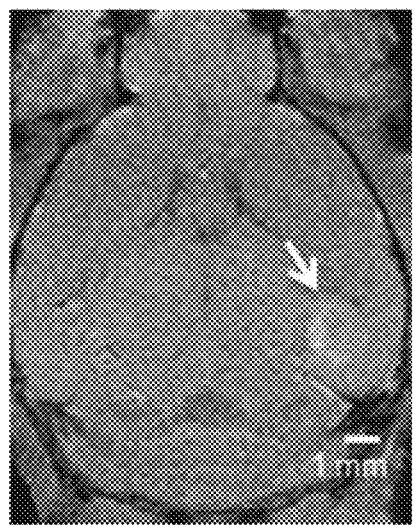
FIG. 22A    FIG. 22B
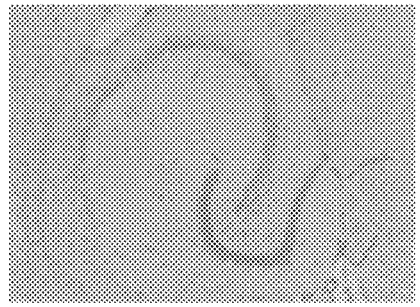 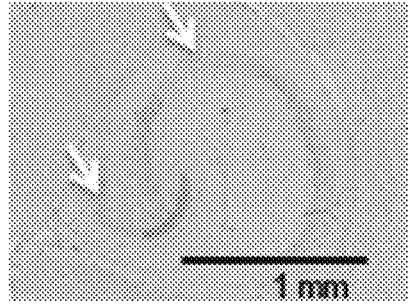
FIG. 22C    FIG. 22D

SYSTEMS AND METHODS FOR OPENING OF A TISSUE BARRIER

CROSS REFERENCE TO RELATED APPLICATIONS

This application is a continuation of U.S. patent application Ser. No. 13/426,400 entitled "Systems And Methods For Opening Of A Tissue Barrier," filed on Mar. 21, 2012, which is a continuation-in-part of International Patent Application No. PCT/US2010/049681, filed on Sep. 21, 2010, which is incorporated by reference in its entirety herein and from which priority is claimed. This application claims priority to U.S. Provisional Application No. 61/244,311 entitled "Improved Opening of Tissue Barrier," filed on Sep. 21, 2009, 61/353,611 entitled "Systems and Methods for Opening a Tissue Utilizing Certain Sonication Pulse Values," filed on Jun. 10, 2010, and 61/353,631 entitled "Brain Drug Delivery Using Focused Ultrasound and Microbubbles," filed Jun. 10, 2010, each of which is incorporated by reference in its entirety herein and from which priority is claimed. This application is also related to U.S. patent application Ser. No. 12/077,612, filed Mar. 19, 2008, and International Patent Application No. PCT/US09/056565, filed Sep. 10, 2009, each of which is incorporated by reference in its entirety herein.

STATEMENT REGARDING FEDERALLY-SPONSORED RESEARCH

This invention was made with government support under EB009041 and EY018505 awarded by the National Institutes of Health and 0644713 awarded by the National Science Foundation. The government has certain rights in the invention.

TECHNICAL FIELD

The present application relates to systems and methods for opening a tissue utilizing acoustic parameters in conjunction with microbubbles.

BACKGROUND

Recent advances in molecular engineering and neuroscience have led to an increasing number of biomarkers and therapeutic agents for the monitoring and treatment of neurological disorders. Many of these agents have proven in vitro specificity or neurological potency, but their in vivo efficacy remains limited by their inability to reach their target due to the blood-brain barrier. This interface regulates the exchange of molecules across the cerebral capillaries through passive, transport, and metabolic barriers, resulting in the exclusion of nearly all agents larger than 400 Da from the brain's extracellular space. Biomarkers and therapeutic agents, such as inhibitors to enzymes (~1 kDa) and antibodies (30 to 300 kDa), are thus rendered ineffective because they do not reach their intended targets.

SUMMARY

Systems and methods for opening a tissue to a target value are disclosed herein. Systems and methods for drug delivery across tissues, e.g., across the blood brain barrier (BBB), are also disclosed herein.

In an embodiment of a method for opening a tissue to a target value using microbubbles, a region of the tissue is targeted for opening, an acoustic parameter corresponding to the target value is determined and an ultrasound beam is applied to the target region at the acoustic parameter such that the tissue at the target region is opened to the target value with the microbubbles. The method can further include positioning microbubbles in proximity to the targeted region and, in some embodiments, positioning the microbubbles can include performing an injection of the microbubbles such that the microbubbles are positioned proximate to the targeted region. The method can further include determining a number of injections and/or a duration of an injection corresponding to the target value. In some embodiments, the injection can be a systemic injection, a bolus injection and/or a slow diffusion injection. The acoustic parameter can be selected to control an acoustic cavitation event and, in some embodiments, controlling an acoustic cavitation event can include controlling a location, number and/or magnitude of acoustic cavitation events. The acoustic parameter can be a pulse length, a pulse repetition frequency, a burst length, a burst repetition frequency, an ultrasound frequency, a pressure range, and/or a duration corresponding to the target value. In some embodiments, the pressure range can correspond to the resonance frequency of the microbubbles proximate to the targeted region.

The method can include determining a concentration range of microbubbles corresponding to the target value and applying an ultrasound beam to move the microbubbles into vessels of the tissue. In some embodiments, the microbubbles can have a size range of 1 to 10 microns, and in other embodiments can have a size range of 1 to 2 microns, 4 to 5 microns, or 6 to 8 microns. The microbubbles can be acoustically activated and/or molecule-carrying. The molecule-carrying microbubbles can carry or be coated with medicinal molecules and/or a contrast agent and/or a biomarker and/or a liposome. Medicinal molecules and/or contrast agents can also be separately positioned in proximity to the targeted region.

The method can further include imaging the targeted region, to form an image of the opened tissue. In some embodiments imaging the targeted region includes applying an ultrasound beam to the targeted region, while in other embodiments imaging the targeted region includes utilizing a magnetic resonance imaging device and/or a fluorescence imaging device to image the targeted region.

An embodiment of a system for opening a tissue to a target value using a solution of microbubbles having a size range corresponding to the target value includes a targeting assembly for targeting a region of the tissue, an introducer for delivering the solution to a location proximate to the targeted region and a transducer, coupled to the targeting assembly, for applying an ultrasound beam to the targeted region at an acoustic parameter corresponding to the target value thereby opening the tissue with the microbubbles to the target value. The acoustic parameter can be selected to control an acoustic cavitation event.

The system can further include an imaging device for capturing image data of the opened tissue of the targeted region, and a processor, operatively coupled to the imaging device, for processing the image data to form an image therefrom. In some embodiments the imaging device includes a transducer for applying an ultrasound beam to the targeted region, while in other embodiments the imaging device includes a magnetic resonance imaging device and/or a fluorescence imaging device to image the targeted region.

BRIEF DESCRIPTION OF THE DRAWINGS

The accompanying drawings, which are incorporated and constitute part of this disclosure, illustrate some embodiments of the disclosed subject matter.

FIG. 6A illustrates a fluorescence image at ten times magnification of a mouse brain after application of tissue opening techniques in accordance with an exemplary embodiment of the disclosed subject matter.

FIGS. 6B-6C illustrate fluorescence images at four times magnification of a mouse brain after application of tissue opening techniques in accordance with an exemplary embodiment of the disclosed subject matter.

FIG. 16F is a diagram showing further details of the disclosed subject matter.

FIGS. 22A-22D illustrate images of a mouse brain subjected to sonication in accordance with an exemplary embodiment of the disclosed subject matter.

Throughout the figures and specification the same reference numerals are used to indicate similar features and/or structures.

DETAILED DESCRIPTION

Figure 1:
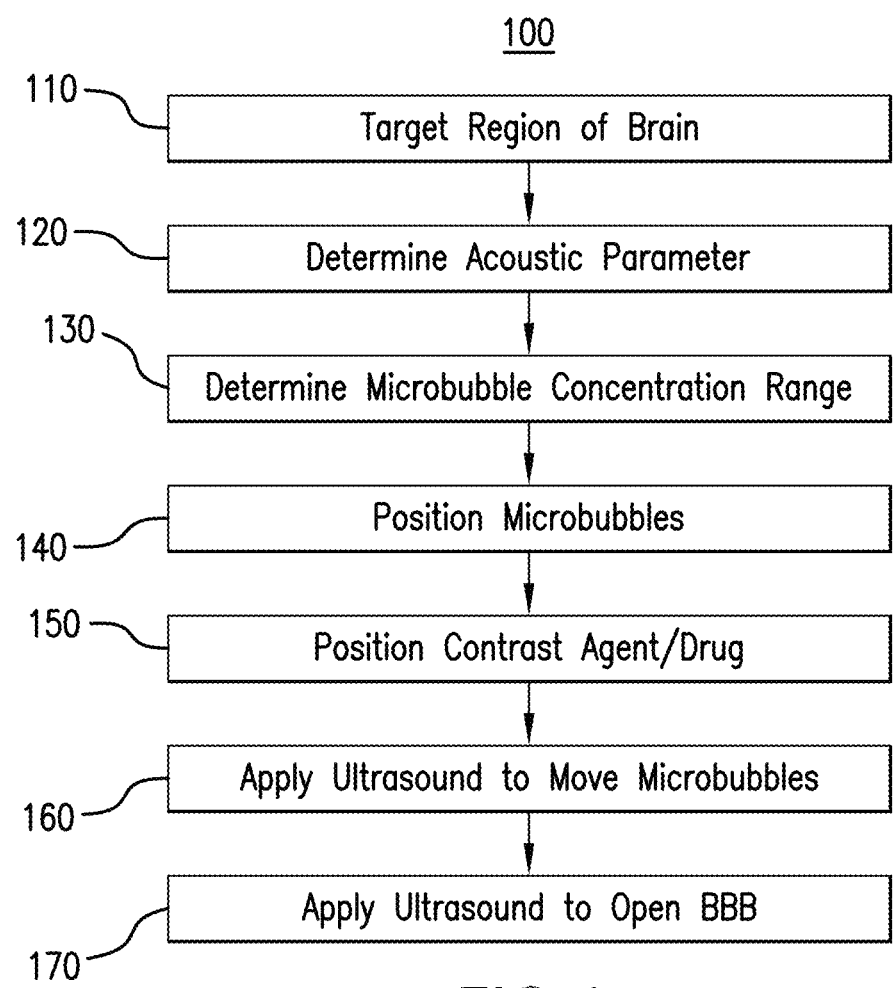
FIG. 1 illustrates a method for opening a blood-brain barrier in a brain of a subject to a target value in accordance with an exemplary embodiment of the disclosed subject matter.

The systems and methods described herein are useful for opening a tissue utilizing microbubbles and focused ultrasound at certain acoustic parameters. Although the description provides as an the example opening the blood-brain barrier, the systems and methods herein are useful for opening other tissues, such as muscular tissue, liver tissue or tumorous tissue, among others.

The subjected matter disclosed herein are methods and systems for determining the acoustic parameters for opening a tissue with the assistance of microbubbles to allow for the passage of certain molecules over selected areas. Accordingly, the techniques described herein make use of selected acoustic parameters chosen to produce a desired opening effect in a tissue when subjected to focus ultrasound utilizing microbubbles of selected sizes and in selected concentrations. The techniques described herein for determining the acoustic parameters for opening a tissue can also be employed in conjunction with other ultrasound techniques, e.g., diagnostic techniques, where opening of a tissue should be avoided. The techniques described herein can be used to determine the acoustic parameters that can be avoided in order to prevent unwanted tissue opening when utilizing such other techniques that, for example, use microbubbles. The techniques described herein provide for reversible opening of a tissue, e.g., the BBB.

In focused ultrasound (FUS), acoustic waves propagate several centimeters through water or tissue and converge onto a focal region while its surroundings remain relatively unaffected. Noninvasive and localized drug delivery systems have emerged from advances in FUS and microbubble technologies. For example, techniques such as blood-brain barrier (BBB) disruption for the treatment of neurological diseases, delivery of nanoparticles to tumors, gene therapy for treating heart conditions, and enhancement of renal ultrafiltration have all shown promise due to their ability to increase uptake of luminal molecules into the interstitial space.

The mechanistic event underlying the tissue opening in such examples is the reaction of microbubbles to ultrasonic pulses, which can result in an array of behaviors known as acoustic cavitation. In stable cavitation, the microbubble expands and contracts with the acoustic pressure rarefaction and compression over several cycles, and such action can result in the displacement of the vessel diameter through dilation and contraction. In inertial cavitation, the bubble can expand to several factors greater than its equilibrium radius and subsequently collapse due to the inertia of the surrounding media, thus also inducing an alteration of the vascular physiology. The type and magnitude of each cavitation activity, including reversibility of the opening, can be dictated by, among other things, the microbubble composition and distribution, the ultrasonic pulse shape and sequence, and the in vivo environment in which the bubbles circulate. Control of molecular delivery using FUS can therefore be facilitated by selecting microbubbles and the acoustic environment conditions that they interact with.

Generally, changing ultrasonic parameters has been associated with a tradeoff between efficacy (e.g., high dose, homogeneous distribution, and consistency) and safety (e.g., erythrocyte extravasations and neuronal damage). The acoustic pressure can have a large influence on the type and magnitude of acoustic cavitation activity. Thus, increasing the pressure increases the likelihood and extent of BBB opening, but also is associated with neurovascular and neuronal damage. At acoustic pressures near the threshold of BBB disruption, histological assessments reveal no detectable damage (e.g., erythrocyte extravasations and/or neuronal damage) but at such low pressures there is also a reduction in molecular delivery. Lowering the transmitted center frequency of the ultrasound can result in a decrease of the acoustic pressure threshold.

The pulse repetition frequency (PRF) can affect the ability of microbubbles to reperfuse the vasculature since each pulse can destroy microbubbles. Further, it has been thought that a long pulse length (PL) was a necessary characteristic of an ultrasonic pulse for inducing BBB disruption, for example PLs of 10 or 20 ms (15200 and 30400 cycles at 1.5 MHz) and such long PLs have been associated with inhomogeneity of drug delivery. However, in accordance with an embodiment herein, it is shown that BBB disruption is feasible at a low pressure (less than 1 MPa) using a PL of 33 μs (50 cycles at 1.5 MHz). Utilizing such a low PL and pressure, an improved distribution of the delivered agent was observed, but an associated decrease in concentration of molecules delivered was also observed. As further shown in an embodiment herein, pulse sequences based on the use of a PL of 2.3 μs (3.5 cycles at 1.5 MHz) can enhance the dose and distribution of delivery without compromising safety.

An acoustic parameter design can be formed on the basis that BBB disruption is dependent on the number, magnitude and/or location of cavitation events occurring throughout the cerebral microvasculature. Further, acoustic cavitation activity within the microvasculature can be modified by taking into account concepts of microbubble persistence, fragmentation, and microvascular replenishment. In one embodiment, a series of pulses can be grouped into a burst, with a sufficient duration between bursts to allow for microbubble replenishment in the microvasculature before arrival of the subsequent acoustic pulses. Grouping pluses into bursts can increase the persistence and mobility of the microbubbles, which can result in a single bubble generating cavitation activity at multiple sites along the cerebral microvasculature. Thus, in some embodiments, short PLs used in a burst sequence can enhance the dose and distribution of molecular delivery without attendant damage to the microvasculature. In the same or other embodiments, the number of injections and duration of each injection of bubbles can be altered to enhance the microbubble persistence, for example.

FIG. 1 illustrates a method 100 for opening a tissue to a target value, e.g., a measure of increased ability of the tissue to pass molecules through. The target value can be expressed in terms of an increase in the size of vessels in the tissue, as an area of the tissue that has been opened, or in terms of a rate at which molecules pass through, e.g., a permeability, or as a combination of any of these measures. The method 100 involves targeting 110 a region of the tissue for opening, determining 120 at least one acoustic parameter corresponding to the target value, positioning 140 microbubbles in proximity to the targeted region, and applying 170 an ultrasound beam at the acoustic parameter to the targeted region such that the tissue is opened with the assistance of the microbubbles to the target value. In some embodiments, positioning 140 the microbubbles can include performing an injection of the microbubbles such that the microbubbles are positioned proximate to the targeted region. The method 100 can further include determining a number of injections and/or a duration of an injection corresponding to the target value. In some embodiments, the injection 140 can be a systemic injection, a bolus injection and/or a slow diffusion injection.

As illustrated in FIG. 1, in one exemplary embodiment, the method 100 can further include of determining 130 a concentration range of microbubbles corresponding to the target value and the positioning 140 of the microbubbles can also include positioning the microbubbles of the concentration range that corresponds to the target value. The method 100 can also include positioning 150 a contrast agent and/or medicinal molecule (e.g., a drug) in proximity to the target region.

In one exemplary embodiment, method 100 can include applying 160 an ultrasound beam to move the microbubbles into vessels of the tissue. This application 160 of the ultrasound beam can be the same, or a different, than the application 170 that is used to open the tissue. Further, the application 160 of the ultrasound beam can be at the same, or at a different, acoustic parameter than that determined 120 for the purposes of opening the tissue.

The acoustic parameter to be determined 120 as corresponding to the target value can be selected to control one or more acoustic cavitation events. The acoustic parameter(s) can be selected such that the location, number and/or magnitude of acoustic cavitation events can be controlled in the targeted tissue. In some embodiments, the acoustic parameter can be at least one of the pulse length, the pulse repetition frequency, the burst length, or the burst repetition frequency, or a combination thereof. In other embodiments, the acoustic parameters that are determined 120 can be the pressure range, the frequency, and the duration of the application 170 of ultrasound.

In some embodiments, the target value of the tissue can be selected based on the size of the molecule that is to pass through the tissue, e.g., the BBB, or based on the size, e.g., area, of the region that is to be exposed to the molecule, or a combination of the two. Thus, in some embodiments, the acoustic parameters can be determined 120 such that the tissue is subject to a certain number of acoustic cavitations at selected locations and of selected magnitudes, which can result in a selected number of molecules of a given size passing through the tissue at selected locations. In one exemplary embodiment, the target value can be such that molecules up to the megaDalton size range are able to pass through the BBB, e.g., 2 MDa molecules.

In one embodiment, the target value can be measured in terms of the normalized optical density (NOD) of a contrast agent such as a dextran, e.g., Texas-Red® fluorescent dye and a molecular weight of 3 kiloDaltons (kDa), using the equation NOD=$F_{L-ROI}$-$F_{R-ROI}$, where $F_{L-ROI}$ is the sum of the pixel values in left region of interest (ROI) of the brain and $R_{L-ROI}$ is the sum of the pixel values in the right ROI of the brain, and where the ultrasound was applied 170 to the left ROI.

In some embodiments, the acoustic parameter can be determined 120 by finding the lowest acoustic parameter value for which the tissue will open to the target value, where the target value is considered to be the minimum amount of opening. In one example involving murine brains, the acoustic parameters to be determined 120 were the PRF and the PL. In accordance with an exemplary experiment detailed below, a PRF value of 1 Hz was experimentally determined 120 to be the lowest PRF for which the BBB of a mouse subject was observed to open based on an observed NOD of approximately $2\times10^7$. A PL value of 0.033 ms was experimentally determined 120 to be the lowest PL for which the BBB was observed to open based on an observed NOD of approximately $0.5\times10^7$. In other embodiments, a PL of 3 cycles (less than 2.5 µs) was experimentally determined 120 to open the BBB in mice, in an experiment conducted in accordance with an exemplary embodiment described below.

In some embodiments, the acoustic parameter can be determined 120 by finding the lowest reliable acoustic parameter value which will reliably open the tissue to the target value. In an example involving murine brains where the target value was considered the minimum NOD for which BBB opening was observed, the acoustic parameters to be determined 120 were the PRF and the PL. In accordance with an exemplary experiment detailed below, a PRF value of 5 Hz was experimentally determined 120 to be the lowest PRF for which the BBB of a mouse subject was observed to reliably open based on an observed NOD of approximately $2\times10^7$. A PL value of 0.2 ms was experimentally determined 120 to be the lowest PL for which the BBB was observed to reliably open based on an observed NOD of approximately $0.5\times10^7$.

In yet other embodiments, the acoustic parameter can be determined 120 by finding the acoustic parameter value above which no further significant increase in opening of the tissue is achieved. In an example involving murine brains where the target value was considered to be the NOD above which no further increase in BBB opening was observed, the acoustic parameters to be determined 120 were the PRF and the PL. In accordance with an exemplary experiment detailed below, a PRF value of 5 Hz was experimentally determined 120 to be the PRF for which no further significant increase in the opening of the BBB of a mouse subject was observed and such opening corresponded to an NOD of approximately $2.5\times10^7$. A PL value of 10 ms was experimentally determined 120 to be the lowest PL for which no further significant increase in the opening of the BBB of a mouse subject was observed and such opening corresponded to an observed NOD of approximately $3\times10^7$.

In the same or other embodiment involving murine brains, the acoustic parameters to be determined 120 can be the burst repetition frequency (BRF) and burst length (BL), where each burst can represent a cluster of pulses. A BRF of 10 Hz was experimentally determined 120 to open the BBB of a mouse subject, where the PRF was set at 100 kHz, and a BRF of 5 Hz was experimentally determined 120 to produce the maximal BBB opening at the same frequency. A BL of 100 pulses was experimentally determined 120 to open the BBB where the PRF was set at 100 kHz and the BRF was set at 5 Hz.

In some embodiments determining 130 a concentration range of microbubbles corresponding to the target value can include determining the minimum microbubble concentration range that will open the tissue to the target value. In an example involving murine brains, a microbubble concentration of 0.01 µl/g was experimentally determined 130 to be the minimum concentration needed to open the BBB. In same or another embodiment, the appropriate concentration of microbubbles can be determined 130 based on the nature of the subject, e.g., a human or a mouse, based on the size of the target region, e.g., the surface area of the BBB that one wishes to open, and based on the vessel size in the target region, e.g., 4-8 µm, or a combination of these factors. In the example of opening a BBB area on the order of millimeters, a concentration range of $10^7$ to $10^9$ bubbles/mL can be appropriate. In one exemplary embodiment, the total concentration for both size ranges of bubbles, e.g., 1-2 and 4-5 µm, was kept constant at approximately $8.5\times10^8$ number of bubbles per mL. In order to ensure accuracy of concentration, the bubbles were generated at an initial yield larger than the desired concentration and then diluted in PBS one minute before intravenous injection into the mouse.

In one exemplary embodiment, the bubble concentration can be chosen to be the same across different size distributions as opposed to the volume fraction, because it can be assumed that BBB opening occurs discretely, e.g., the sites of molecular leakage highly correlated with the instantaneous locations of the bubbles at the time of sonication. This implies that BBB opening sites are punctuated along the length of the capillaries. In the case where the volume fraction was kept the same for both sets of bubbles, it is deemed that the imaging protocol used would have the required sensitivity to detect minute increases in fluorescence.

As detailed in commonly assigned International Patent Pub. WO 2010/030819, which is incorporated by reference in its entirety herein, in some embodiments the appropriate size range of microbubbles can be determined by comparing the bubble size to the cerebral vasculature size and selecting a bubble size that is small enough to perfuse the vessels while at the same time large enough to induce sufficient mechanical stress on the vessel walls, such that the vessels are opened to the target value.

Figure 2:
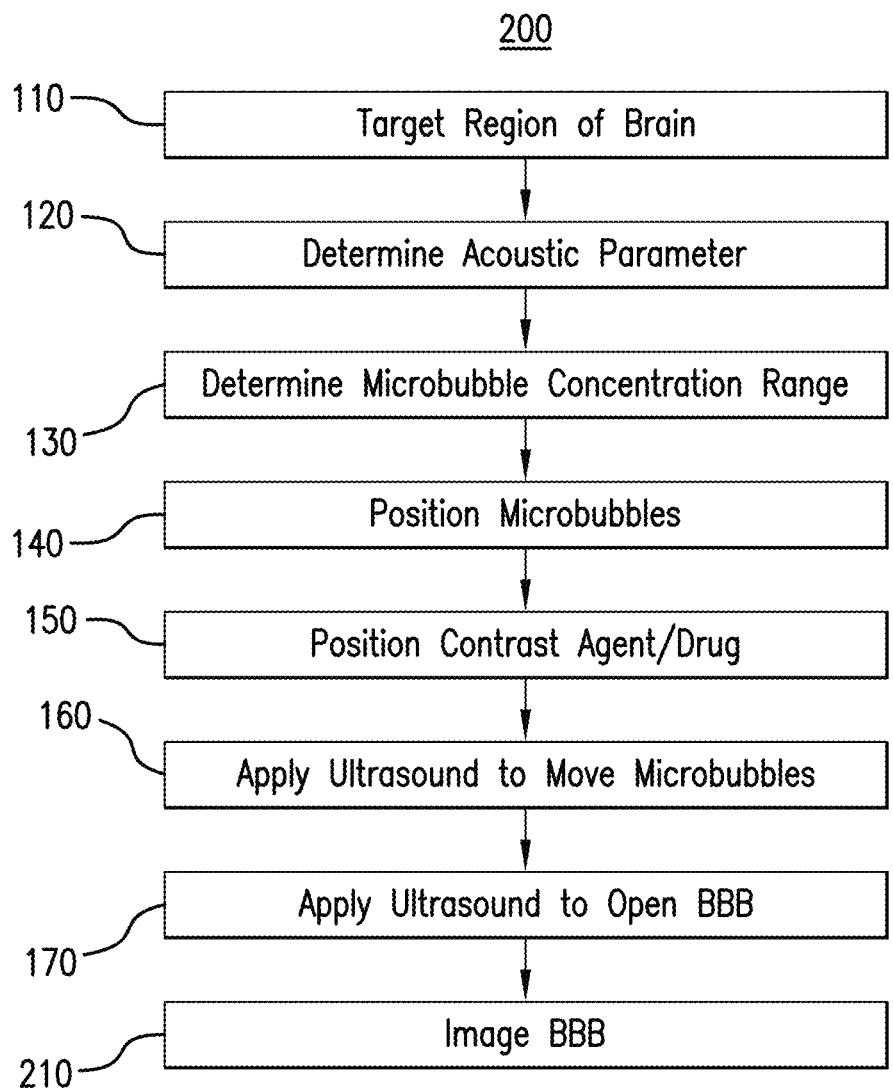
FIG. 2 illustrates a method for imaging the opening of a blood-brain barrier in a brain of a subject to a target value in accordance with an exemplary embodiment of the disclosed subject matter.

FIG. 2 illustrates a method 200 in accordance with the disclosed subject matter for imaging the opening of a tissue. The method 200 includes the same basic techniques for opening the tissue to a target value: targeting 110 a region of the tissue for opening, determining 120 at least one acoustic parameter corresponding to the target value, positioning 140 microbubbles of a known size range in proximity to the targeted region, and applying 170 an ultrasound beam at the acoustic parameter to the targeted region such that the tissue is opened with the assistance of the microbubbles to the target value. The method 200 further includes imaging 210 the opened tissue. In some embodiments, imaging 210 the opened tissue can be the same as the application 170 of an ultrasound beam to open the tissue. In another embodiment, imaging 210 can include utilizing an MRI device to image the opening of the tissue.

Figure 3A:
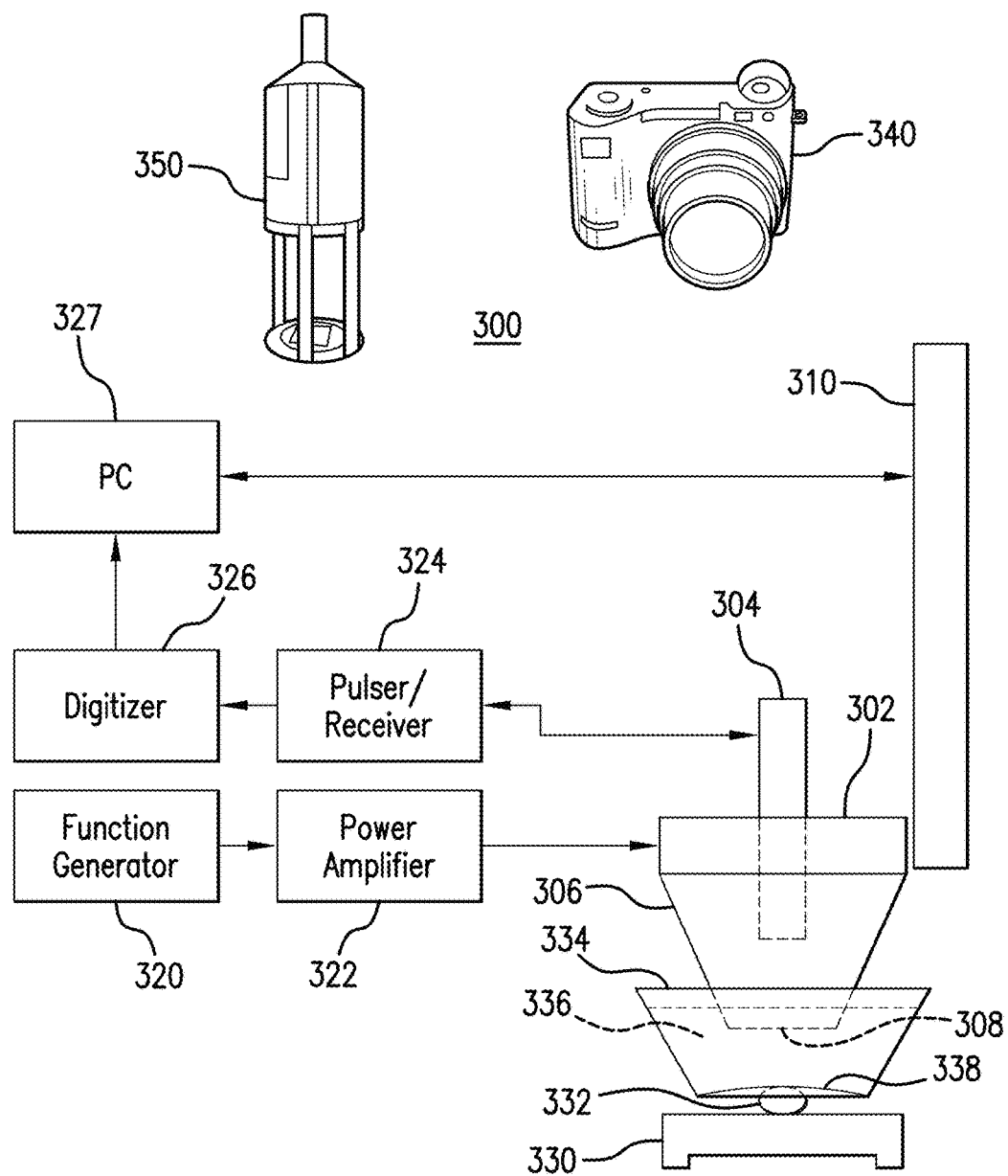
FIG. 3A illustrates a system for opening and/or imaging the opening of a blood-brain barrier in a brain of a subject to a target value in accordance with an exemplary embodiment of the disclosed subject matter.

FIG. 3A illustrates a system 300 for opening a tissue to a target value. System 300 has many of the same features as the system described in U.S. Patent Pub. No. 2009/0005711 and International Patent Pub. No. WO 2010/030819, commonly assigned patent applications, each of which is incorporated by reference in its entirety herein. Ultrasound waves are generated by a focused ultrasound transducer (FUS) 302, which can be a single-element circular-aperture FUS transducer. In one exemplary embodiment the FUS transducer 302 can be a single-element, spherical segment FUS transducer with center frequency of 1.525 MHz, a focal depth of 90 mm, an outer radius of 30 mm, and an inner radius of 11.2 mm (Riverside Research Institute, New York, N.Y., USA). The FUS transducer can be provided with hole in its center for receipt of an imaging transducer 304, which can be a single-element diagnostic transducer having a center frequency of 7.5 MHz with a focal length of 60 mm (Riverside Research Institute, New York, N.Y., USA). The FUS transducer 302 and the diagnostic transducer 304 can be positioned so that the foci of the two transducers are properly aligned, e.g., overlap.

Further illustrated in FIG. 3A, an exemplary system 300 can include a cone 306 filled with degassed and distilled water and mounted on system 300. The cone 306 can, for example, be manufactured from a clear plastic, such as polyurethane. The water is contained in the cone 306 by capping it with a material considered substantially "transparent" to the ultrasound beam, such as an ultrathin polyurethane membrane 308 (Trojan; Church & Dwight Co., Princeton, N.J., USA).

The transducer assembly, which can include the FUS transducer 302 and the diagnostic transducer 304, can be mounted to a computer-controlled 3-D positioning system 310 (Velmex Inc., Lachine, QC, Canada), including motors VXM-1 and VXM-2 used in the exemplary embodiment. It is understood that other positioning systems can be incorporated for positioning the transducer assembly with respect to the targeted tissue.

In the same or another exemplary embodiment, the FUS transducer 302 can be driven by a function generator 320, e.g., function generator HP33150A, manufactured by Agilent Technologies, Palo Alto, Calif., USA, through an amplifier 322, such as a 50-dB power amplifier 3100L (ENI, Inc., Rochester, N.Y., USA). The diagnostic transducer 304 can be driven by a pulser-receiver system 342, for example a pulser-receiver 5052PR (Panametrics, Waltham, Mass., USA), connected to a digitizer 326, e.g., digitizer CS14200 (Gage Applied Technologies, Inc., Lachine, QC, Canada). It is understood that the above-described components can be modified or replaced with other components, as is known in the art, for producing the ultrasound beams described herein. Computer 328 typically includes a processor, such as a CPU (not shown), and can be any appropriate personal computer or distributed computer system including a server and a client. For example, a computer useful for this system is a Dell Precision 380 personal computer. It is understood that any personal computer, laptop, or other processor that can load software and communicate with the various components discussed herein can be used. A memory unit (not shown), such as a disk drive, flash memory, volatile memory, etc., can be used to store software for positioning and operating the transducer assembly, image data, a user interface software, and any other software which can be loaded onto the CPU.

Figure 3B:
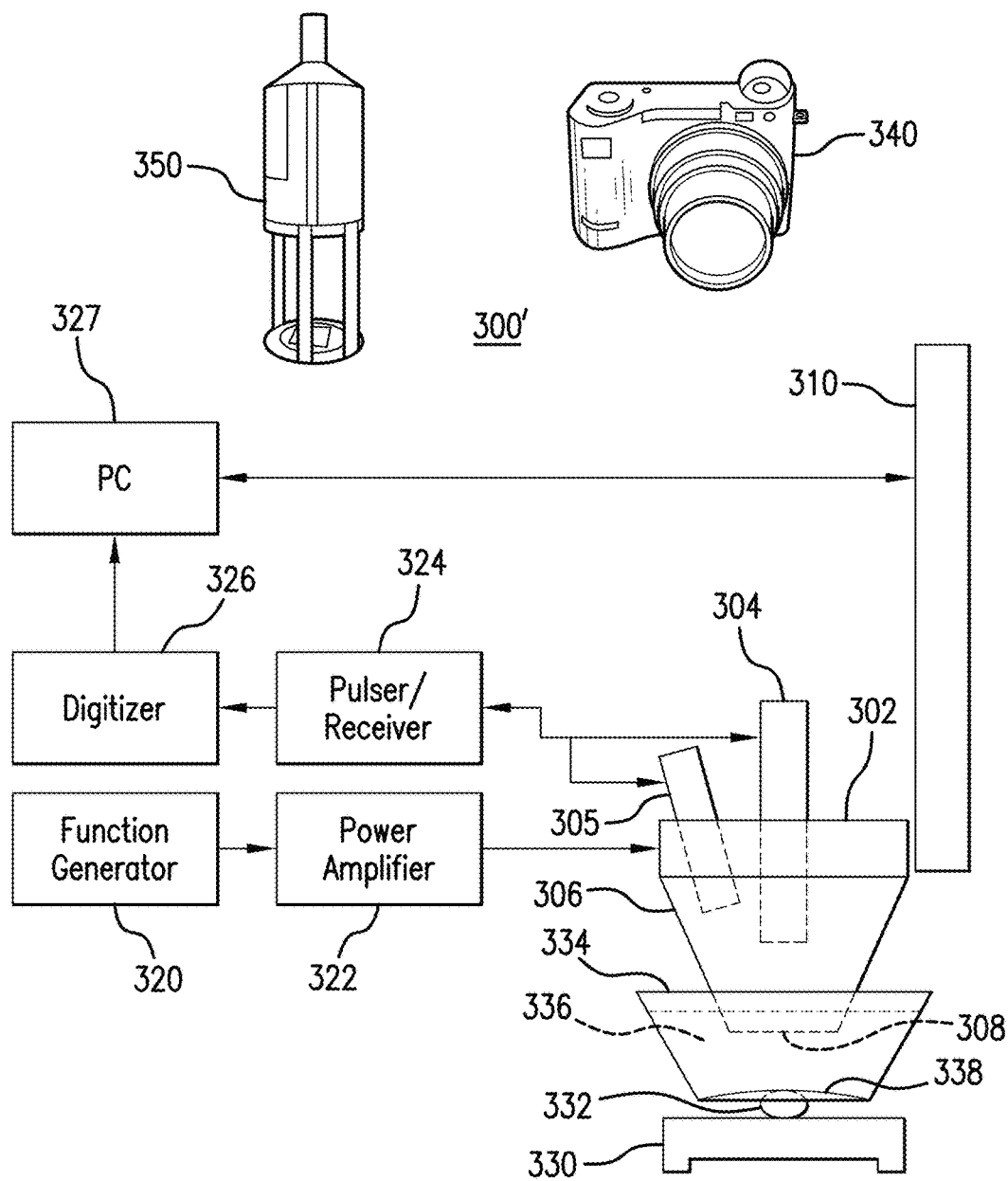
FIG. 3B illustrates another system for opening and/or imaging the opening of a blood-brain barrier in a brain of a subject to a target value in accordance with an exemplary embodiment of the disclosed subject matter.

In another exemplary embodiment illustrated in FIG. 3B, system 300' can include a transducer assembly having an array of a plurality of single-element FUS transducers 304 and 305 which can be targeted to different regions of the tissue of the subject. Each FUS transducer 304, 305 in the array can be fired individually, thereby permitting opening of the BBB in several locations without repositioning the transducer assembly.

Prior to sonication and in order to verify undistorted propagation through the skull, a scan, such as a 3-D raster-scan (lateral step size: 0.2 mm; axial step size: 1.0 mm), of the beam of the FUS transducer 302, can optionally be performed in a large water tank containing degassed water with a needle hydrophone having a needle diameter on the order of about 0.2 mm (Precision Acoustics Ltd., Dorchester, Dorset, UK). In this manner the pressure amplitudes and three-dimensional beam dimensions of the FUS transducer 302 can be measured. The pressure amplitudes can be measured by calculating the peak-rarefactional pressure values and accounting for an pressure attenuation due to transcranial propagation, e.g., an 18% pressure attenuation. The dimensions of the beam provided by the FUS transmitter 302 can have a lateral and axial full-width at half-maximum (FWHM) intensity of approximately 1.32 and 13.0 mm, respectively, and in some embodiments can be approximately equal to the dimensions of the beam after propagation through the skull.

System 300 also includes a liquid container 334 containing an appropriate liquid 336, e.g., degassed and distilled water, which is sealed at the bottom with a membrane 338, which can be a polyurethane membrane that is acoustically and transparent, e.g., plastic wrap. The system 300 can also include an optical imaging device 340, such as a digital camera, for imaging the skull of the subject 332 and a MRI device 350 for imaging the brain of the subject 332.

System 300 also includes a platform 330 for the subject. In one exemplary embodiment, the platform 330 for the subject can be a polyurethane bed for a smaller subject 332, such as a mouse. In this configuration, the membrane 338 can be placed over the subject 332. In other embodiments, the platform 330 can be a hospital bed or surgical table, in which a larger subject 332 (such as a human subject) can be laid prone or supine and the transducer assembly positioned on top of the region of the skull targeted.

Figure 4A:
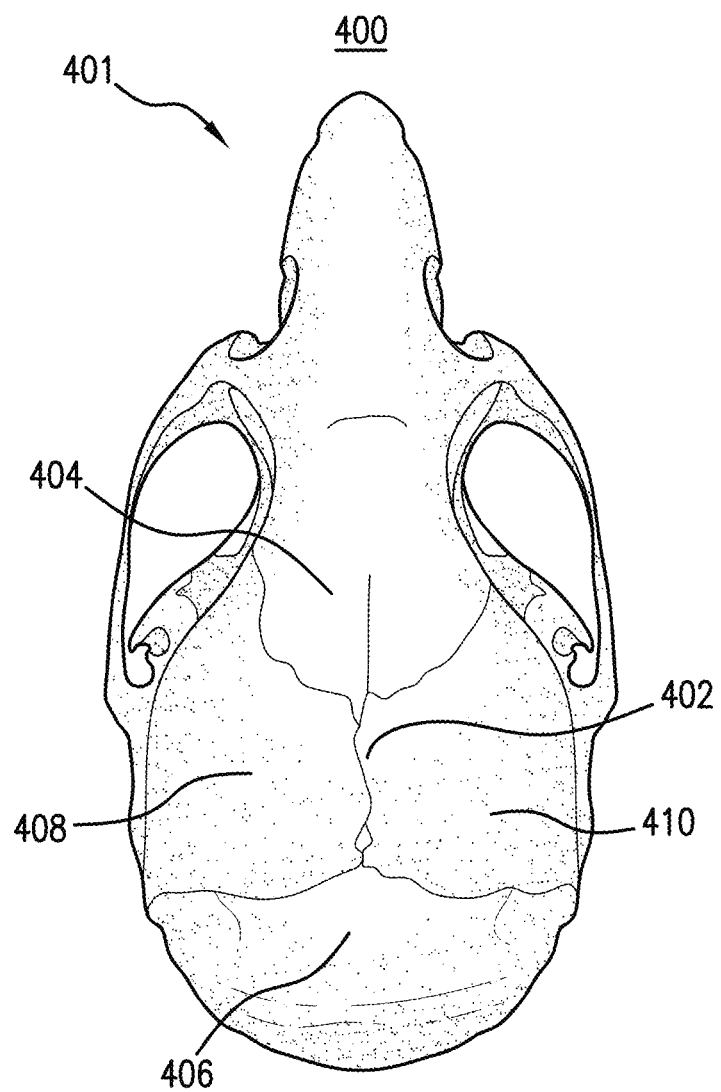
FIGS. 4A-4E illustrate a targeting system for locating a target region of the brain of a subject in accordance with an exemplary embodiment of the disclosed subject matter.

Additional components of the system 300 include a targeting system 400, coupled to the FUS transducer 302, for locating the focus of the FUS transducer 302 in the brain of the subject 332. The targeting system 400 can be coupled by any known method that permits the targeting system 400 to aid in properly targeting the FUS transducer 302 to the region of interest for opening of the target tissue, e.g., acoustic and/or optical coupling. FIGS. 4A-4D illustrate a targeting system 400 for use with an embodiment where the subject 332 is a mouse. FIG. 4A illustrates mouse skull 401, where the skull's sutures can be seen through the skin and used as anatomic landmarks for targeting purposes. As illustrated in FIG. 4A, the landmarks of mouse skull 401 include the sagittal suture 402, the frontal bone 404, the interparietal bone 406, the left parietal bone 408, and the right parietal bone 410.

Figure 4B:
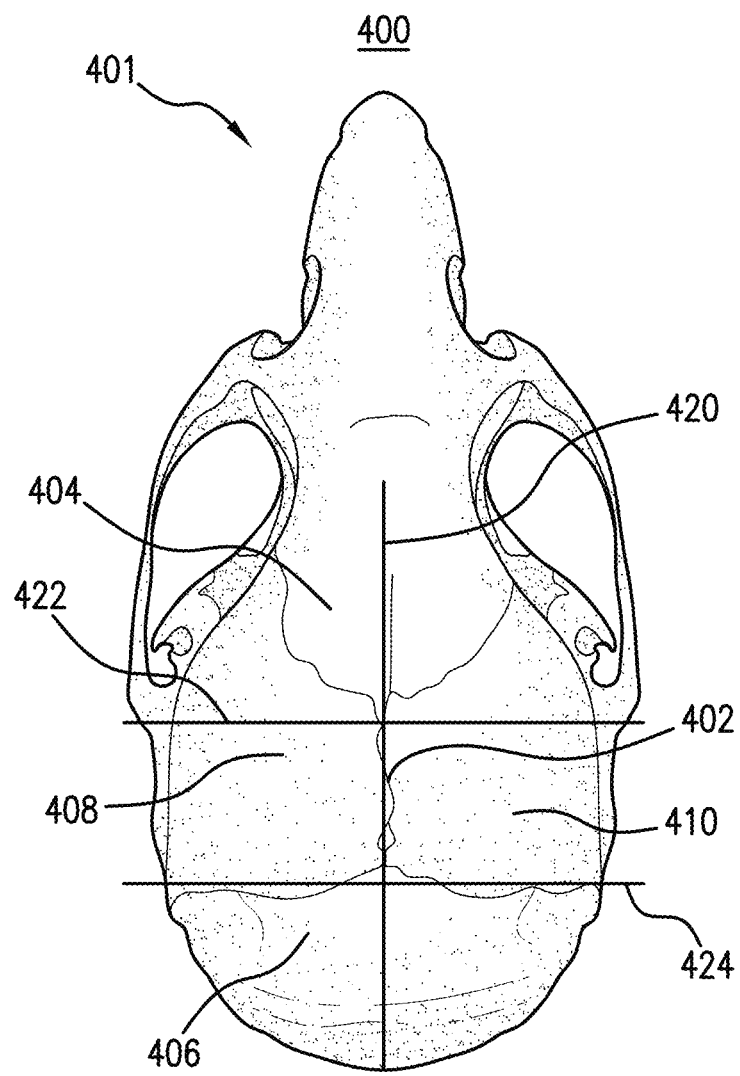

FIG. 4B illustrates the placement of targeting system 400 on skull 401 in accordance with an exemplary embodiment. The targeting system 400 can include a plurality of members 420, 422, 424, such as thin metal bars, e.g., 0.3 mm thin metal bars, fabricated from an acoustically reflective material, e.g., paper clips. The metal bars 420, 422, 424 can be placed on several landmarks of the skull of the subject to create a layout, or grid. As illustrated in FIG. 4B, a grid consisting of three equally spaced 0.3-mm thin F2 metal bars 420, 422, 424 were placed in the water bath 334 on top of the skull 401 and in alignment with these landmarks, e.g., bone sutures. The first bar 420 was aligned parallel and along the sagittal suture 402, and the second bar 424 was attached perpendicularly to the first bar and in alignment with the suture between the parietal 408 and interparietal bone 406. The third bar 422 was placed 4 mm away from and parallel to the second bar 424.

Figure 4C:
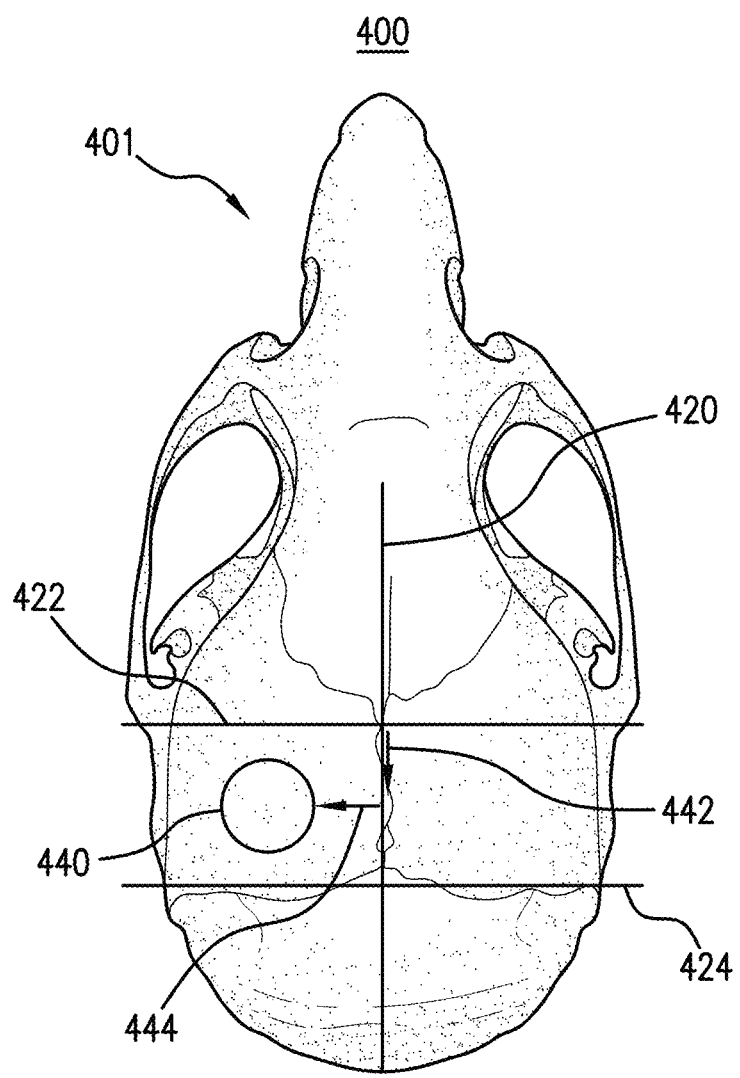

FIG. 4C illustrates the location of a brain structure 440 to be targeted, here the hippocampus, relative to the landmarks noted above. The location of the hippocampi are assumed relative to the sutures based on the mouse brain and known skull anatomy. In this exemplary embodiment, using the grid positioning system 400, the location of one of the hippocampi (indicated by circle 440) was reproducibly targeted when assumed to be at mid-distance (arrow 442) between the parallel bars 422, 424 and 2 mm away from the center bar 420 (arrow 444).

To locate the desired brain structure 440 an image, such as a lateral 2-D raster scan, of the grid configuration can be made using the diagnostic transducer 304. The focus of the FUS transducer 302 can then be positioned to precisely target the desired brain structure 440. In another exemplary embodiment, the targeting system can include other imaging devices, such as a digital camera 340. For example, a digital camera 340 can be used to photograph the head of the subject 332. The relevant landmarks can be identified in the photograph, and the focus of the FUS transducer 302 targeted to a location relative to the landmarks. In addition, other MM targeting equipment, as is known in the art, can be used for targeting the desired brain structure 440 or other targeted tissue structure.

Figure 4D:
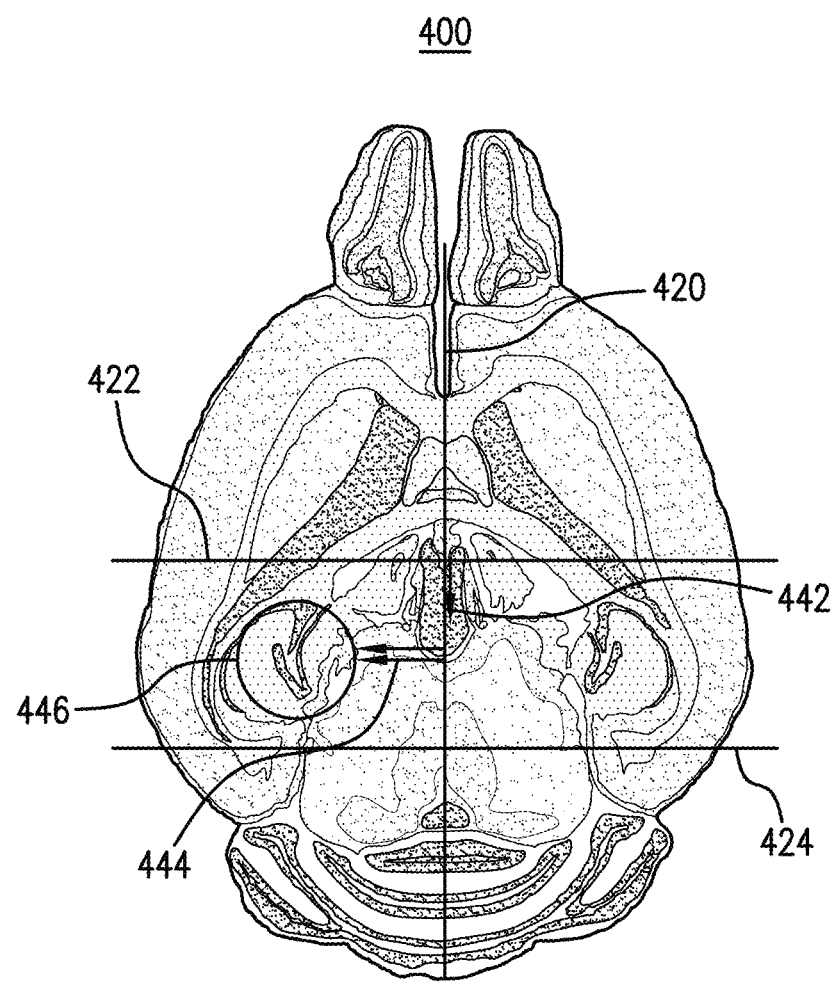
Figure 4E:
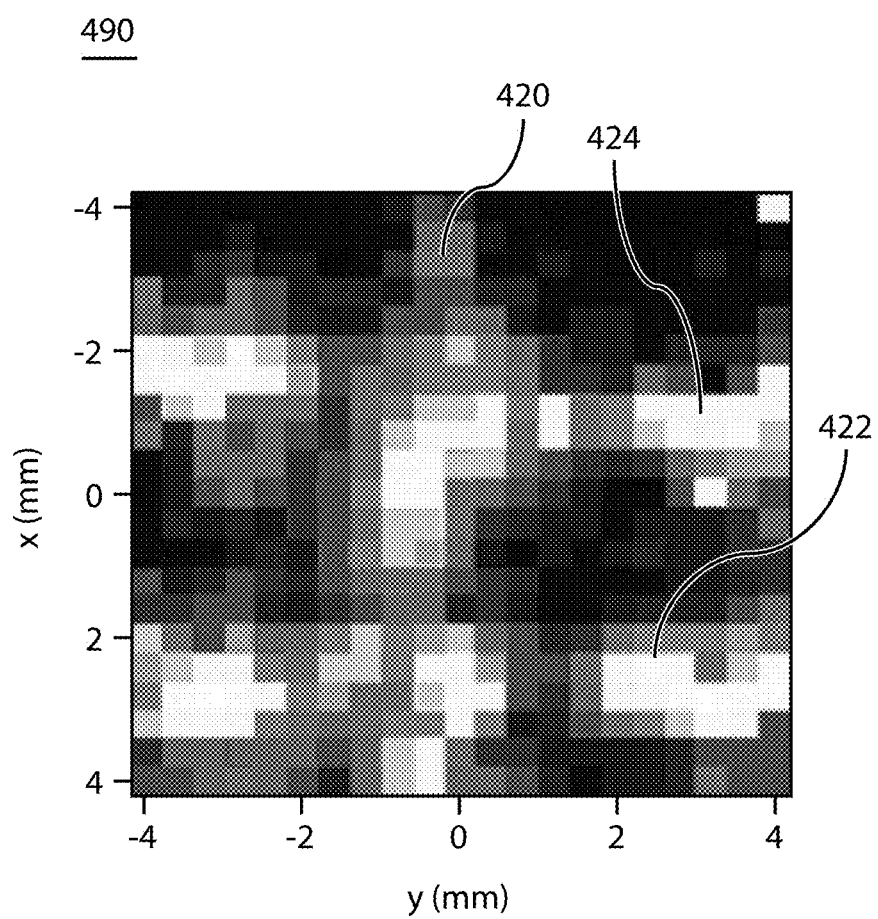

FIG. 4D illustrates the actual location of the hippocampus 446 as indicated in the histology slice. FIG. 4E illustrates a lateral 2-D raster-scan 490 of the grid 400 using the diagnostic transducer 304. The location of the hippocampus can be identified relative to this grid. The focus of the FUS transducer 302 was placed 3 mm beneath the top of the skull by measuring distance with the diagnostic transducer 304. Using the grid positioning system 400 and depth calculations, precise, accurate and reproducible targeting of the hippocampus or other brain structures can be performed. In one exemplary embodiment, the grid positioning system 400 allowed for sonication of the same location with good accuracy across different mice. This allowed for not only good reproducibility across different mice, but also a good comparison of BBB opening effects in different regions 440 within the sonicated area.

An exemplary method 100 for opening the BBB will be described in connection with the above-referenced figures. The subject 332 is positioned on a platform 330. Subject 332 can be positioned in a prone position, and can be anesthetized for the sonication procedure. The degassed and distilled water bath 334 is suspended over the subject's 332 head. Ultrasound gel can be used to reduce any remaining impedance mismatches between the thin plastic layer 338 and the subject's 332 skin. The transducer assembly can be placed in the water bath 334 with its beam axis perpendicular to the surface of the skull 401.

The focus of the transducer is positioned inside the subject's 332 brain. The focus can be targeted 110 to a region of the brain 440, such as the desired brain tissue, e.g., the hippocampus 446, or to the vasculature of the brain, e.g., arteries, ventricles, arterioles, and capillaries of the brain, or to other target tissue regions at different locations in the subject 332. The targeted region 440 of the brain can be located 110 utilizing the targeting system as discussed above.

Example 1

Figure 5:
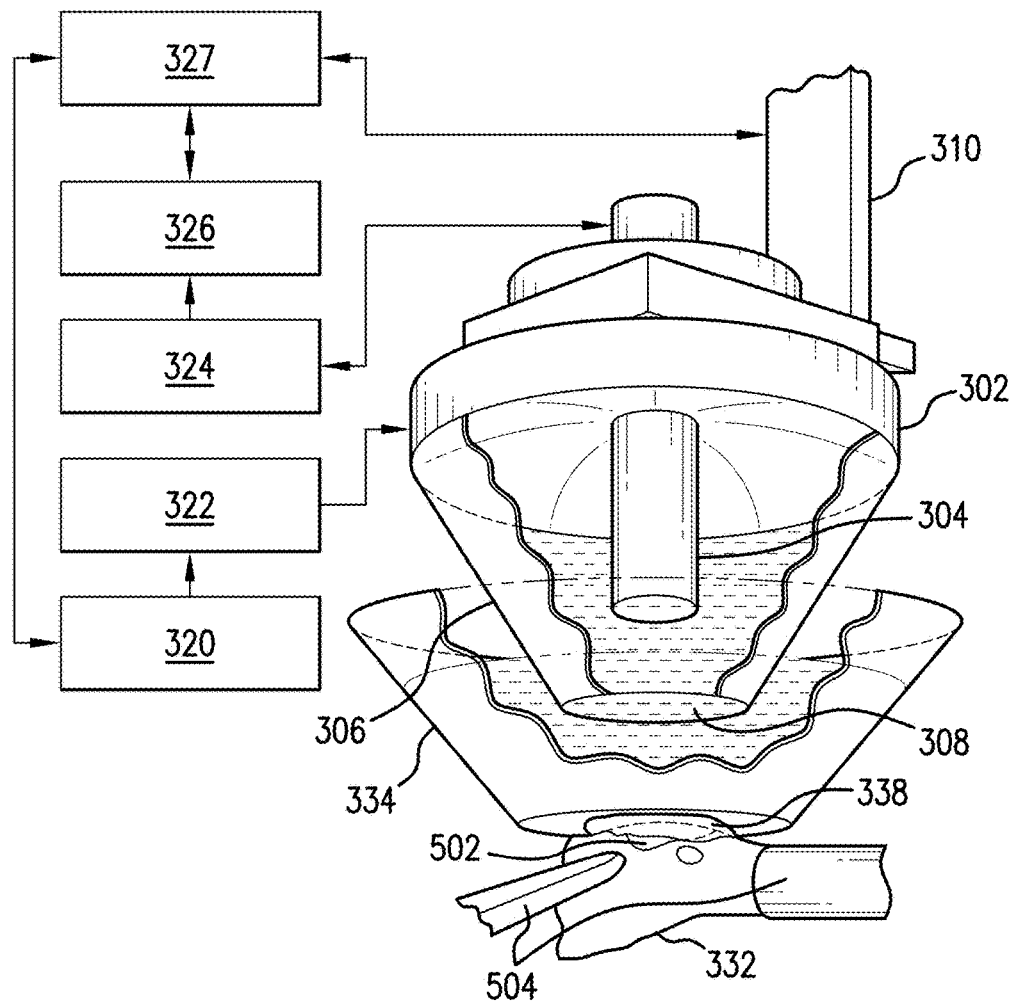
FIG. 5 illustrates a system for opening the blood-brain barrier used in connection with an experiment on mice in accordance with an exemplary embodiment of the disclosed subject matter.
Figure 7:
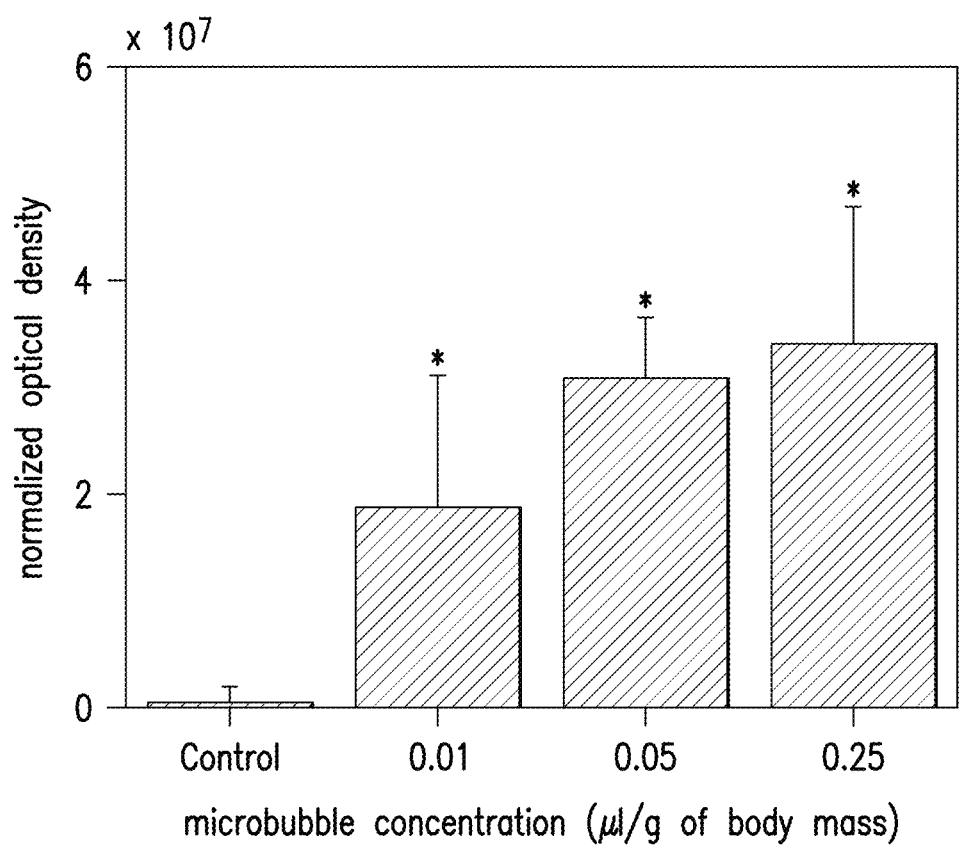
FIG. 7 is a graph illustrating the effects of varying the microbubble concentration in accordance with an exemplary embodiment of the disclosed subject matter.

FIG. 5 illustrates a system 300 used in an experiment, approved by the Columbia University Institutional Animal Care and Use Committee, on seventy-nine wild-type mice (strain: C57BL/6, mass: 28.0±4.5 g, sex: male; Harlan, Indianapolis, Ind., USA) which were studied in accordance with the techniques described herein. As illustrated in FIG. 7, the system 300 can include a FUS transducer 302, a pulse-echo diagnostic transducer 304, a cone 306, a latex membrane 308, a 3-D positioning system 310 all operatively connected to a function generator 320, a power amplifier 322, a pulse-receiver system 324, a digitizer 326 and a computer 327. The cone 306 can be inserted into a water container 334 which is sealed at the bottom by a polyurethane membrane 338 and placed on the shaved skull 502 of the mouse subject 332. The mouse subject 332 is held in place using a stereotaxic apparatus 504.

In the experiment, the mice were anesthetized using 1.25-2.50% isoflurane (SurgiVet, Smiths Medical PM, Inc., Wisconsin, USA) throughout both the BBB opening and transcardial perfusion procedures. After being anesthetized, each mouse 332 was placed prone with its head immobilized by the stereotaxic apparatus 504 (David Kopf Instruments, Tujunga, Calif., USA). The hair on the skull was removed using an electric trimmer and a depiatory cream. A degassed water-filled container 334 sealed at the bottom with thin, acoustically and optically transparent, Saran™ Wrap 338 (Saran™; SC Johnson, Racine, Wis., USA) was placed on top of the mouse head 602 while ultrasound coupling gel was used to eliminate any remaining impedance mismatch between the two surfaces. The FUS transducer 302 was then submerged in the water of the container 334 with its beam axis perpendicular to the surface of the skull 332.

The focus of the transducer was positioned inside the mouse brain using a grid-positioning method that utilized the pulse-echo diagnostic transducer 304, as discussed above. The grid was constructed from three 0.30 mm thin metal bars (i.e., paper clips) with two of the bars parallel to one another and separated by 4.00 mm. At the center of the parallel bars, and perpendicular to the two, was soldered the third bar. The grid was placed in the water bath 334, on top of the skull, and in alignment with sutures visible through the skin. The center bar was aligned along the sagittal suture and one of the parallel bars with the lambdoid suture. A lateral two-dimensional raster-scan of the grid using the diagnostic transducer was made and the transducer's beam axis was positioned 2.25 and 2.00 mm away from the sagittal and lambdoid suture, respectively. Finally, the focal point was placed 3.00 mm beneath the top of the skull so that the acoustic wave propagated through the left parietal bone and overlapped with the left hippocampus and a small portion of the lateral region of the thalamus. The right hippocampus was not targeted and was used as the control. The grid positioning method was sufficiently precise to have the FUS beam consistently overlap the hippocampus of the murine brain.

The tissue opening procedure 100 involved injection 140, 150 a 25 μl bolus of Definity® microbubbles (1-10 μm) and a dextran contrast agent (Texas-Red® fluorescent dye with a molecular weight of 3 kDa) into the tail vein 1 minute after the start of sonication 170, with the injection taking place over a 30 second period. Sonication was performed for 11 minutes total using pulsed FUS at a set pressure of 0.51 MPa peak-rarefactional at a single location (e.g., the hippocampus).

After the 11 minutes of sonication 170, the dextran was allowed to circulate and accumulate in the mouse brain for 10 minutes, after which a transcardial perfusion with phosphate buffer saline (138 mM sodium chloride, 10 mM phosphate, pH 7.4) and 60 ml of 4% paraformaldehyde was performed. The brain was extracted from the skull and then post-fixed in the paraformaldehyde overnight. Following the aforementioned procedures, the brain was prepared for frozen sections. The frozen sectioning protocol provided an efficient means of analyzing fluorescence in order to determine the threshold for BBB opening. In preparation of frozen sectioning, the brain was cryoprotected by soaking it in 30% sucrose overnight. The brain was then embedded in a cutting temperature compound (Sakura Tissue-Tek O.C.T. Compound; Torrance, Calif., USA), frozen in a square mold, and then sectioned using a cryostat into nine sections of 100 μm slices in the horizontal orientation.

Bright field and fluorescent images of the frozen sections were acquired using an inverted light and fluorescence microscope (IX-81; Olympus, Melville, N.Y., USA) at 4× magnification and with a motorized stage-scanner. Images of the paraffin sections were acquired using an upright light and fluorescence microscope (BX61; Olympus, Melville, N.Y., USA) at 4× and 10× magnification. The Texas Red-tagged dextrans were excited at 568±24 nm while emissions were filtered for 610±40 nm.

As noted above, the nine horizontal sections were chosen at defined cross-sections of the hippocampus. FIG. 6A illustrates a horizontal section at 10× magnification, with the left and right ROIs shown in the left and right boxes. FIG. 6B shows the left ROI, which was subjected to sonication procedures, as detailed above, and FIG. 6C shows the right ROI, which was the control. In order to process the image, the regions of interest (ROIs) for each of the nine sections were outlined using Adobe® Photoshop® CS2 (San Jose, Calif., USA), as illustrated FIGS. 6B-6C. The outlines were then loaded into MATLAB® (Natick, Mass., USA) and used to isolate the hippocampus in the fluorescent images. The images were normalized by dividing both the left and right images by the spatially averaged right (control) image of the hippocampus, thus calculating $F_{L\text{-}HIP}$. The threshold for an image was were the pixel value was greater than 2 standard deviations of $F_{L\text{-}HIP}$; images exceeding the threshold were excluded from the calculations. The normalized optical density (NOD) was then calculated for each section, using the equation $NOD=F_{L\text{-}ROI}-F_{R\text{-}ROI}$, where $F_{L\text{-}ROI}$ is the sum of the pixel values in left ROI of the brain and $R_{L\text{-}ROI}$ is the sum of the pixel values in the right ROI of the brain. The NOD for the brain was calculated by averaging the NOD of across all nine sections. The resulting averaged NOD was then used to determine whether, to what extent, the BBB had opened.

FIG. 7 is a graph illustrating the effects of varying the microbubble concentration in an exemplary embodiment where the FUS pressure was 0.46 MPa, the microbubbles used where Definity® bubbles, the PRF was 10 Hz and the PL was 20 ms. The asterisks (*) indicates a significant difference in NOD from the control. As can be seen in FIG. 7, there was a significant NOD increase for all concentrations test and further there was not a significant difference between the tested concentrations, indicating that with Definity microbubbles a concentration of 0.01 μl/g of body mass is both sufficient to open the BBB in mice and also reliable for doing the same.

Figure 8A:
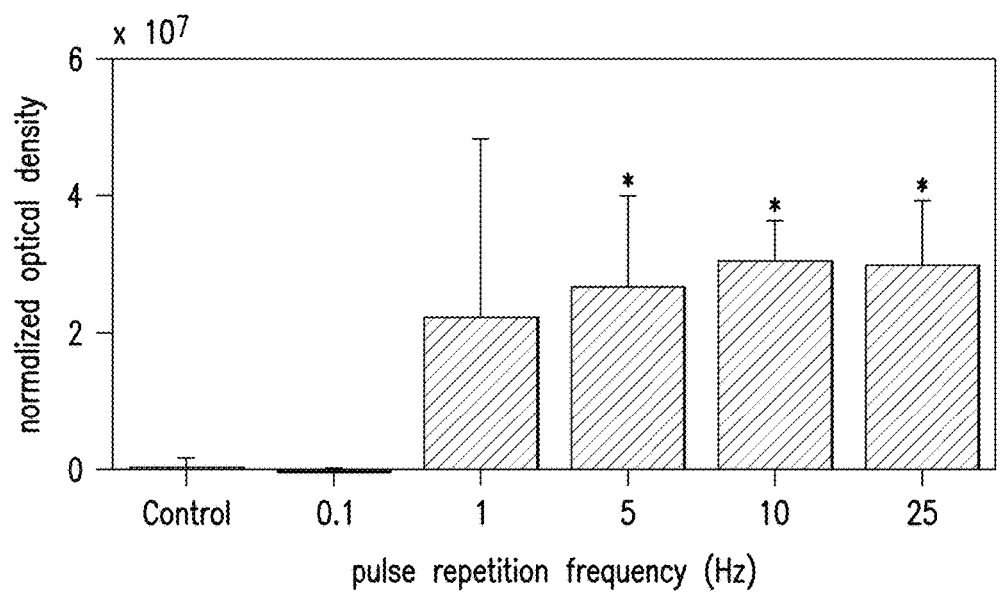
FIG. 8A is a graph illustrating the effects of varying the pulse repetition frequency in accordance with an exemplary embodiment of the disclosed subject matter.
Figure 8B:
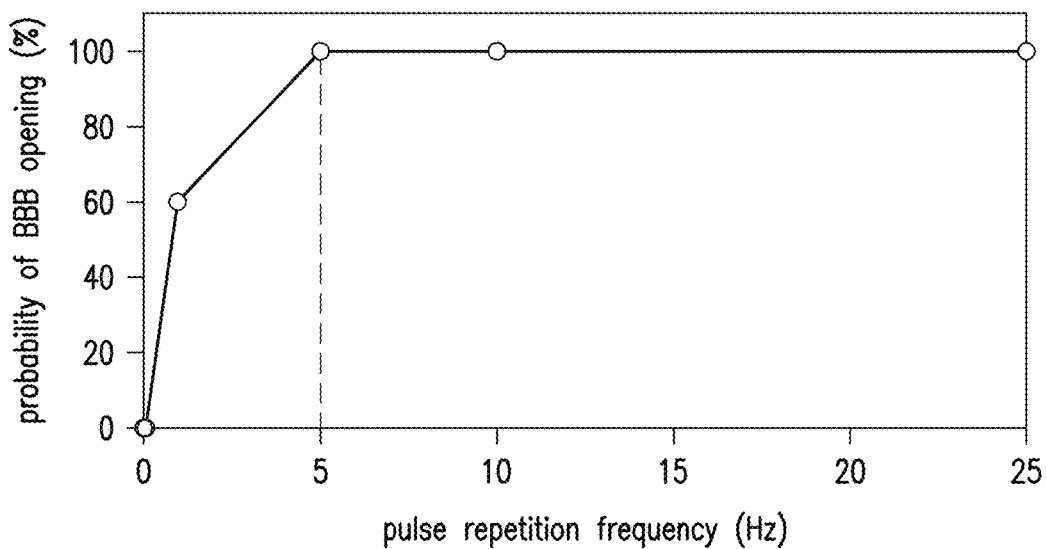
FIG. 8B is a graph illustrating the probability of blood-brain barrier opening as a function of varying the pulse repetition frequency in accordance with an exemplary embodiment of the disclosed subject matter.

FIG. 8A is a graph illustrating the effects of varying the PRF in an exemplary embodiment where the FUS pressure was 0.46 MPa, the microbubbles used were Definity® bubbles, the microbubble concentration was set at 0.05 μl/g of body mass, and the PL was 20 ms. The asterisks (*) indicates a significant difference in NOD from the control. As illustrated in FIG. 8A, at least one pulse is needed to open the BBB in a mouse brain prepared in accordance with the procedures set forth above. Further, the lowest PRF that was observed to open the BBB was 1 Hz, while the lowest PRF that was observed to reliably open the BBB was 5 Hz. FIG. 8B further illustrates these findings, showing the PRF as a function of the probability of BBB opening. As illustrated in FIG. 8B, at 5 Hz and above there is a 100% probability of the BBB opening in the mice subjects prepared in accordance with the exemplary procedures set forth above. FIG. 8A also illustrates that no additional benefits are gained from using a PRF greater than 5 Hz.

Figure 9A:
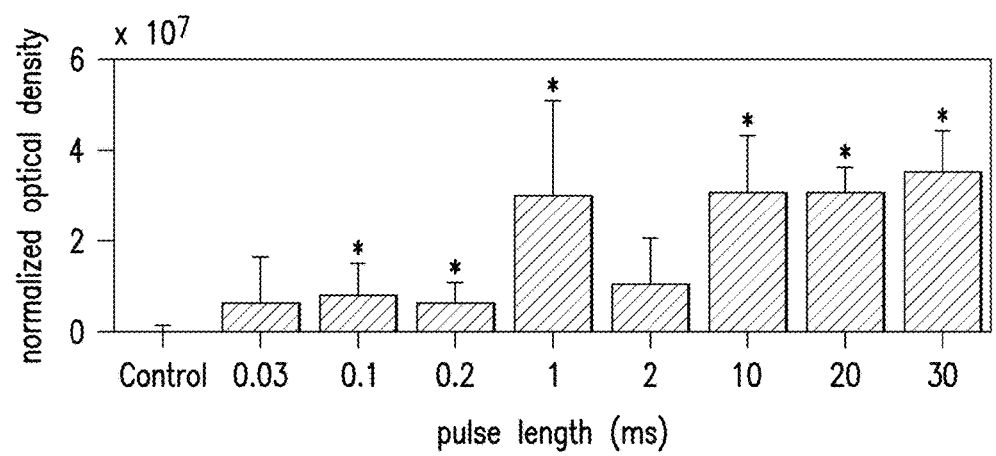
FIG. 9A is a graph illustrating the effects of varying the pulse length in accordance with an exemplary embodiment of the disclosed subject matter.
Figure 9B:
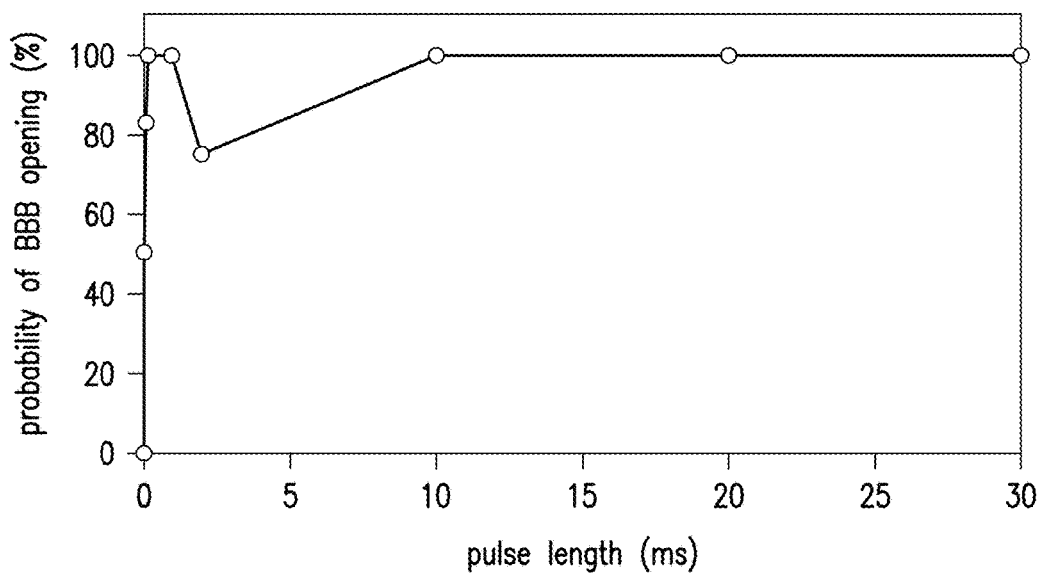
FIGS. 9B-9C are graphs illustrating the probability of blood-brain barrier opening as a function of varying the pulse length in accordance with an exemplary embodiment of the disclosed subject matter.
Figure 9C:
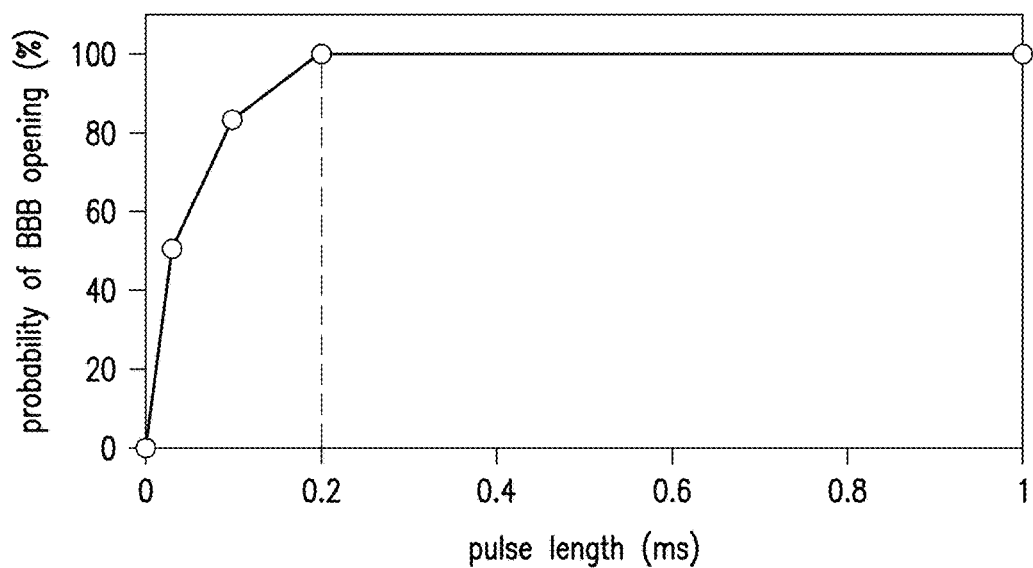

FIG. 9A is a graph illustrating the effects of varying the PL in an exemplary embodiment where the FUS pressure was 0.46 MPa, the microbubbles used were Definity® bubbles, the microbubble concentration was set at 0.05 μl/g of body mass, and the PRF was 10 Hz. The asterisks (*) indicates a significant difference in NOD from the control. As illustrated in FIG. 9A, lowest PL which resulted in BBB opening was 0.033 ms, while 0.2 ms was the lowest PL which produced reliable BBB opening in mice prepared in accordance with the above-detailed exemplary procedures. The results illustrated in FIG. 9A demonstrate that, contrary to prior understanding, pulse lengths shorter than 10 ms can reliably open the BBB for FUS applications utilizing pressures less than 0.5 MPa. FIG. 9A also illustrates that no additional benefits are gained from using a PL greater than 10 ms. FIGS. 9B and 9C illustrate the PL as a function of the probability of BBB opening, with FIG. 9B showing the data across all PLs tested in the exemplary experiment discussed herein and FIG. 9C illustrating the shortest PLs tested. As illustrated in FIG. 9C, a PL of as short as 0.1 ms has been shown to reliably open the BBB of mice prepared in accordance with the exemplary procedures described herein, which is contrary to prior understanding of the necessary PL for FUS applications employing pressures less than 0.5 MPa.

Figure 10A:
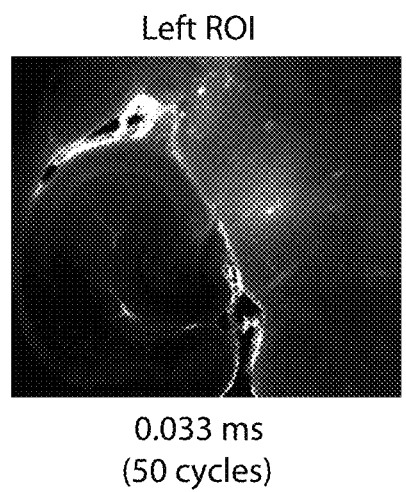
FIGS. 10A-10H illustrate histological images of a mouse brain after focused ultrasound sonication with a varying pulse length in accordance with an exemplary embodiment of the disclosed subject matter.
Figure 10B:
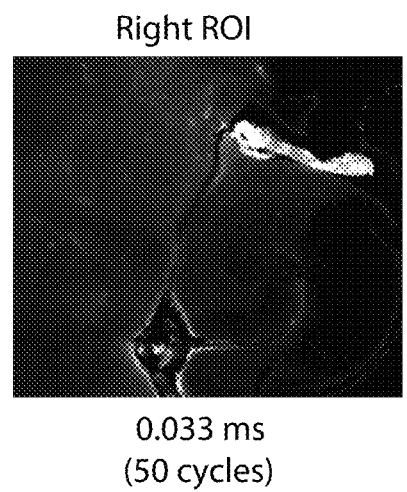
Figure 10C:
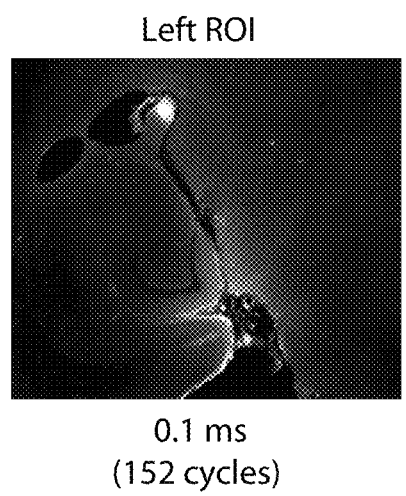
Figure 10D:
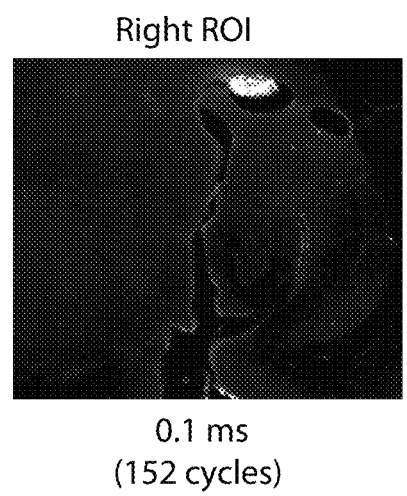
Figure 10E:
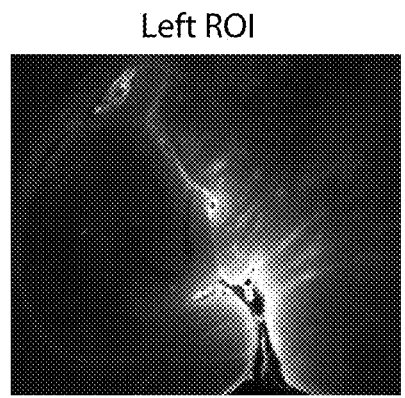
Figure 10F:
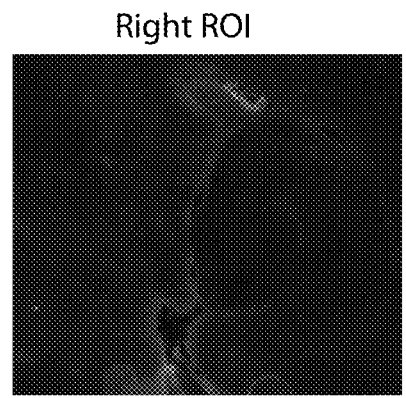
Figure 10G:
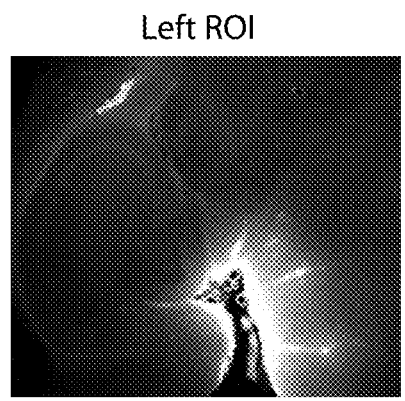
Figure 10H:
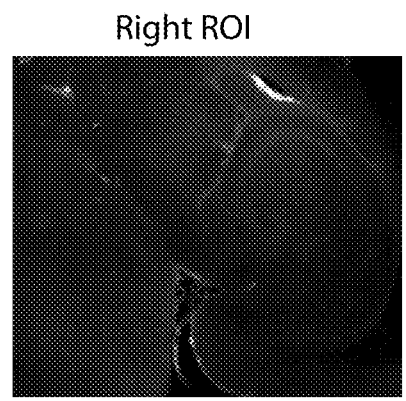

FIGS. 10A-10H are images of murine brains prepared in accordance with the above-detailed exemplary procedures and illustrate the results of varying the PL from 0.033 ms (50 cycles) to 30 ms (45600 cycles). FIGS. 10A and 10B illustrate the left sonicated ROI and right control ROI, respectively, at a PL of 0.033 ms (50 cycles). FIGS. 10C and 10D illustrate the left sonicated ROI and right control ROI, respectively, at a PL of 0.1 ms (152 cycles). FIGS. 10E and 10F illustrate the left sonicated ROI and right control ROI, respectively, at a PL of 20 ms (30400 cycles). FIGS. 10G and 10H illustrate the left sonicated ROI and right control ROI, respectively, at a PL of 30 ms (45600 cycles).

Figure 11:
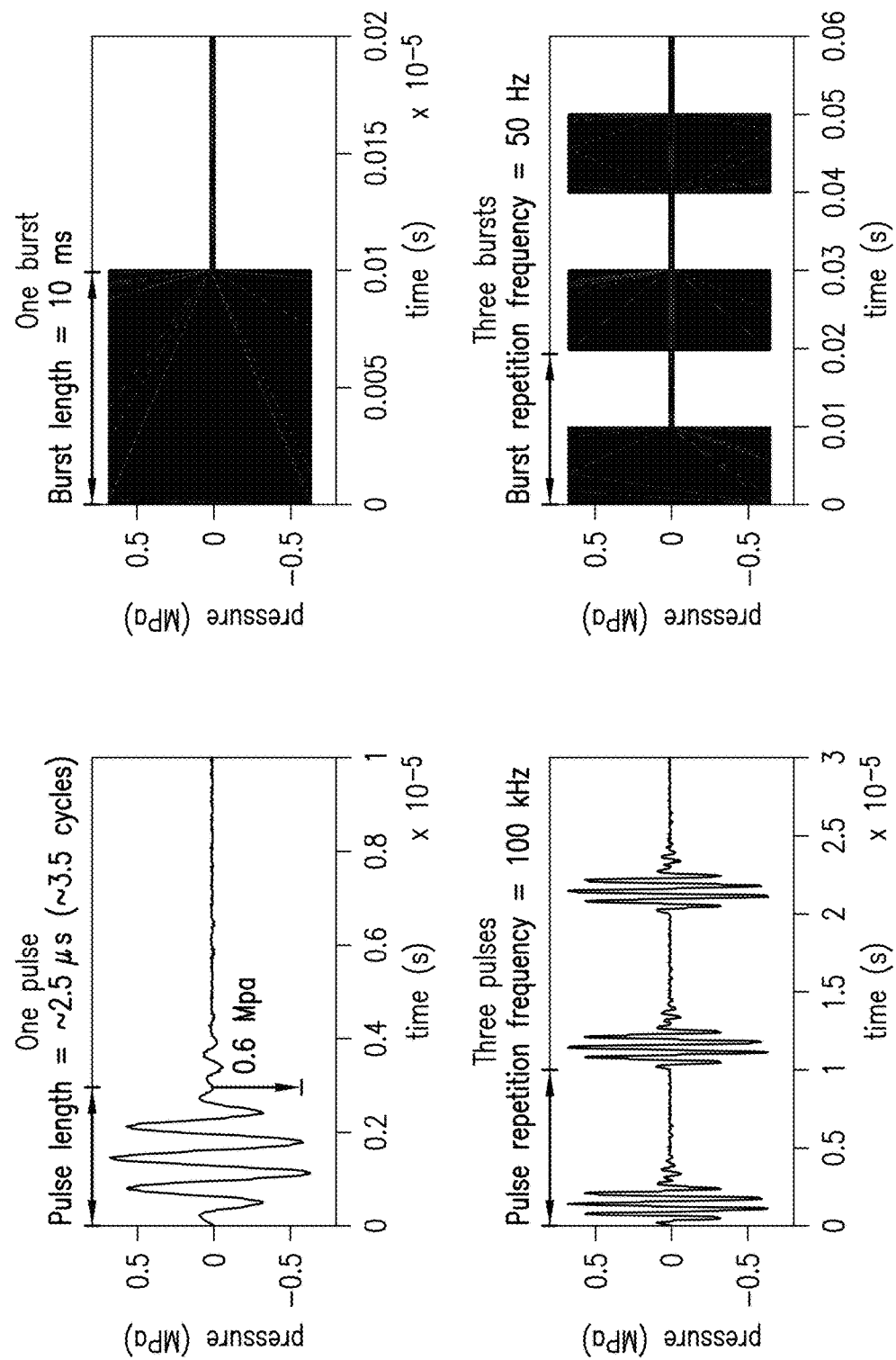
FIG. 11 illustrates an exemplary pulse and burst sequence in accordance with an exemplary embodiment of the disclosed subject matter.

FIG. 11 illustrates an exemplary pulse and burst sequence, where each burst is composed set of pulses operating at a certain pulse rate frequency (PRF). For example and as illustrated in FIG. 11, one pulse can have a PL of 2.5 μs (approximately 3.5 cycles) at a pressure of 0.6 MPa. As illustrated, the pulses can be repeated at a PRF of, for example, 100 kHz. The pulsing can be continued for a period of time, e.g., 10 ms, which comprises a single burst of a certain length (BL). Finally, the bursts can be repeated at a certain rate, for example 50 Hz, which is the BRF.

Figure 12A:
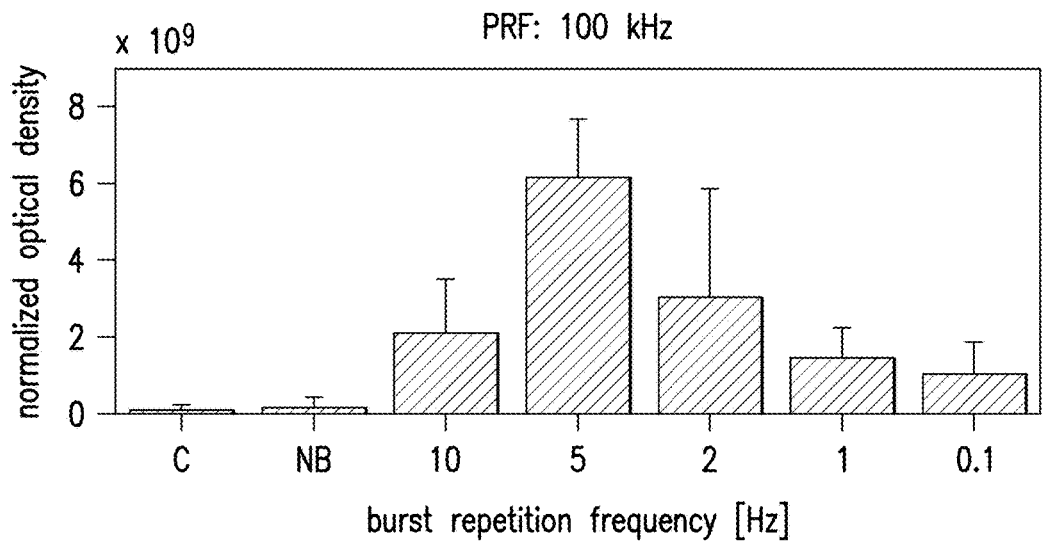
FIGS. 12A-12C are graphs illustrating the effects of varying the burst repetition frequency for three different pulse repetition frequencies in accordance with an exemplary embodiment of the disclosed subject matter.
Figure 12B:
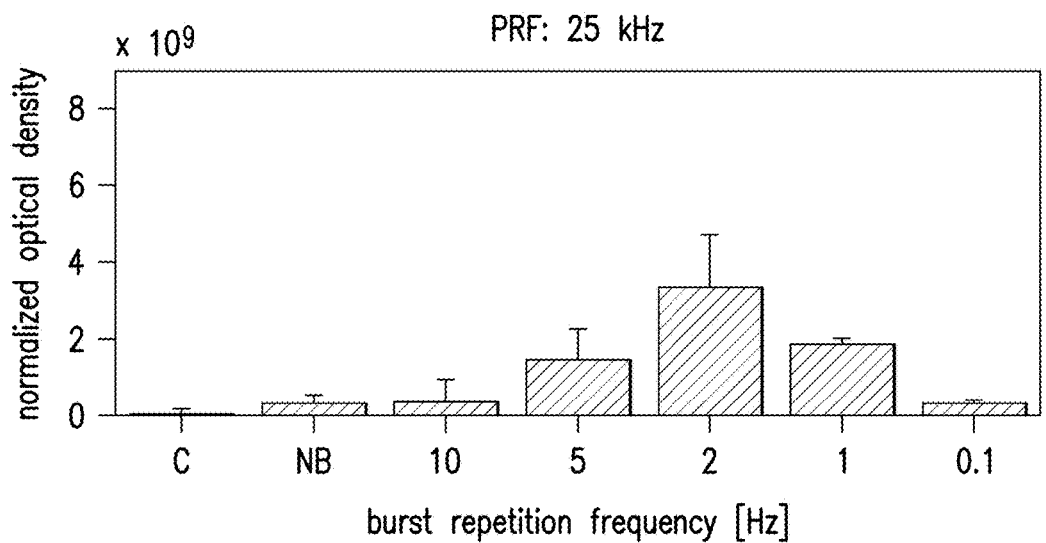
Figure 12C:
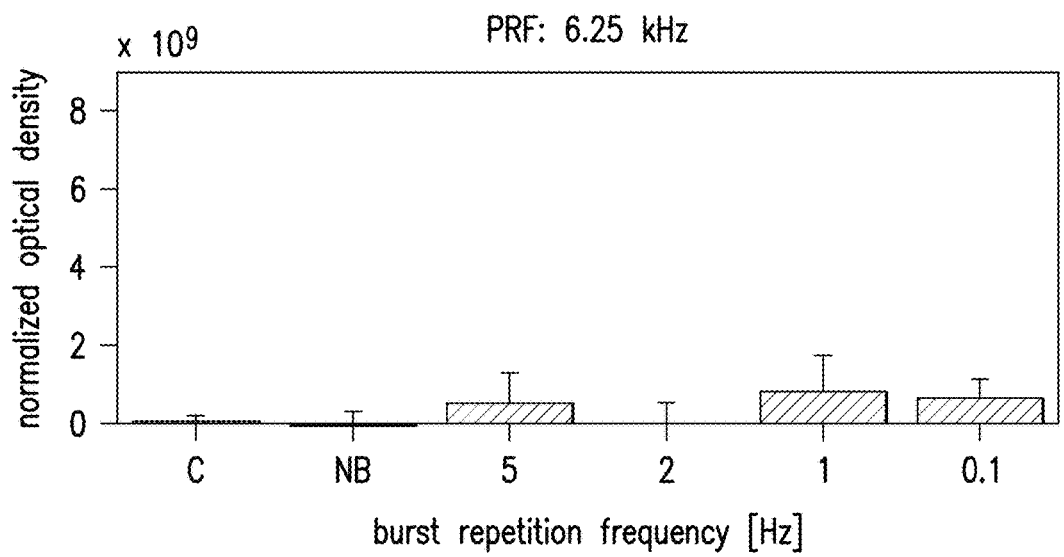

FIGS. 12A-12C illustrate the NOD as a function of the BRF for three different PRFs, for an exemplary experiment involving mice preformed in accordance with the above-detailed procedures. FIG. 12A is a graph illustrating the effects of varying the BRF, in an exemplary embodiment where the FUS pressure was 0.46 MPa, the microbubbles used were Definity® bubbles, the microbubble concentration was set at 0.05 μl/g of body mass, the sonication duration was 11 minutes, the BL was 1000 pulses, and the PRF was set at 100 kHz. FIG. 12B is a graph illustrating the effects of varying the BRF, in an exemplary embodiment having the same parameters as noted for FIG. 12A, except at a PRF of 25 kHz. FIG. 12B is a graph illustrating the effects of varying the BRF, in an exemplary embodiment having the same parameters as noted for FIG. 12A, except at a PRF of 6.25 kHz.

Figure 12D:
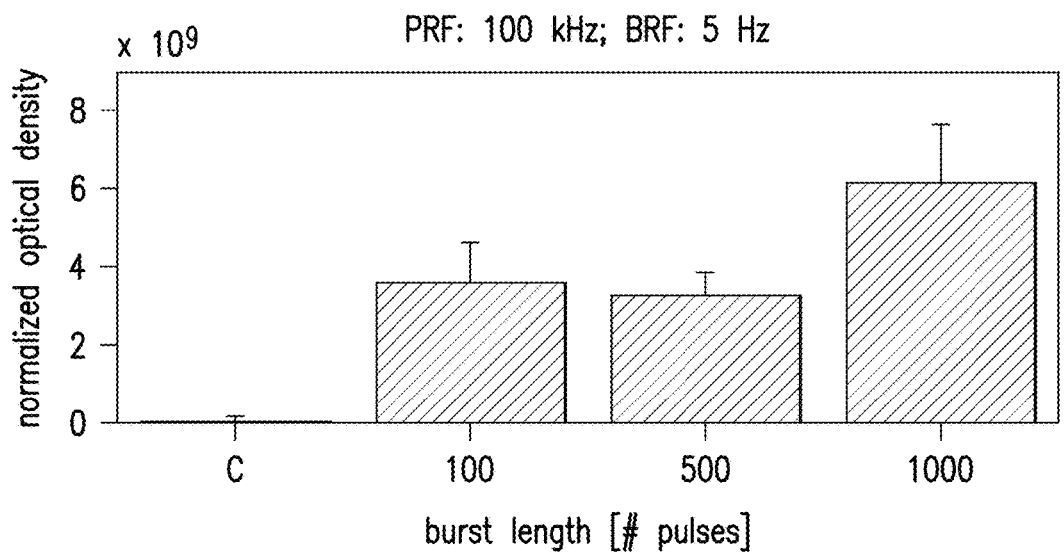
FIG. 12D is a graph illustrating the effects of varying the burst length for a certain pulse repetition frequency and burst length in accordance with an exemplary embodiment of the disclosed subject matter.

FIG. 12D is a graph illustrating the effects of varying the BL, in an exemplary embodiment where the FUS pressure was 0.46 MPa, the microbubbles used were Definity® bubbles, the microbubble concentration was set at 0.05 μl/g of body mass, the sonication duration was 11 minutes, the BRF was 5 Hz, and the PRF was 100 kHz.

Figure 13A:
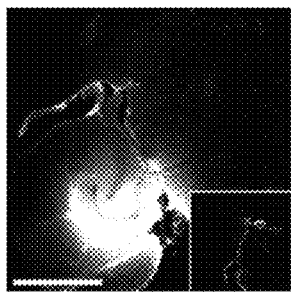
FIGS. 13A-13I illustrate images of a mouse brain subjected to sonication in accordance with an exemplary embodiment of the disclosed subject matter.
Figure 13B:
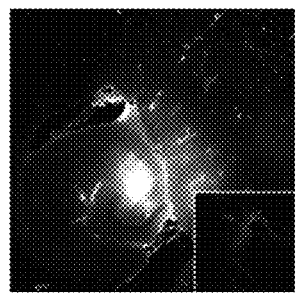
Figure 13C:
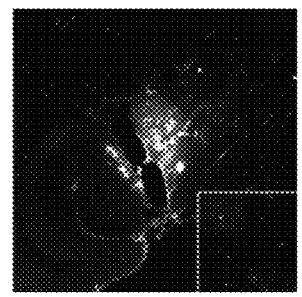
Figure 13D:
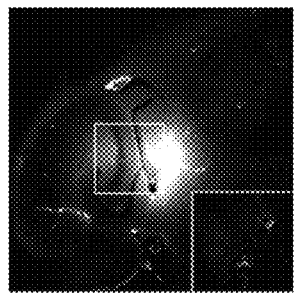
Figure 13E:
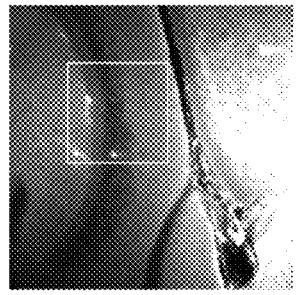
Figure 13F:
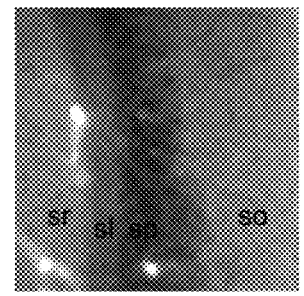
Figure 13G:
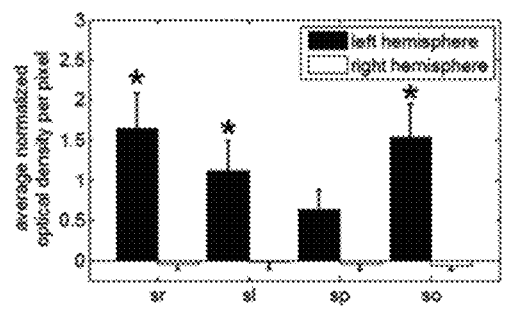
Figure 13H:
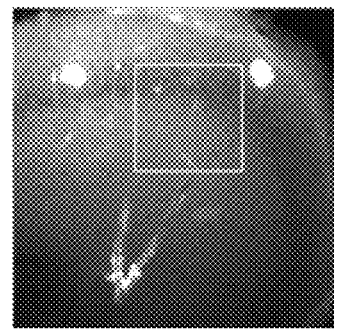
Figure 13I:
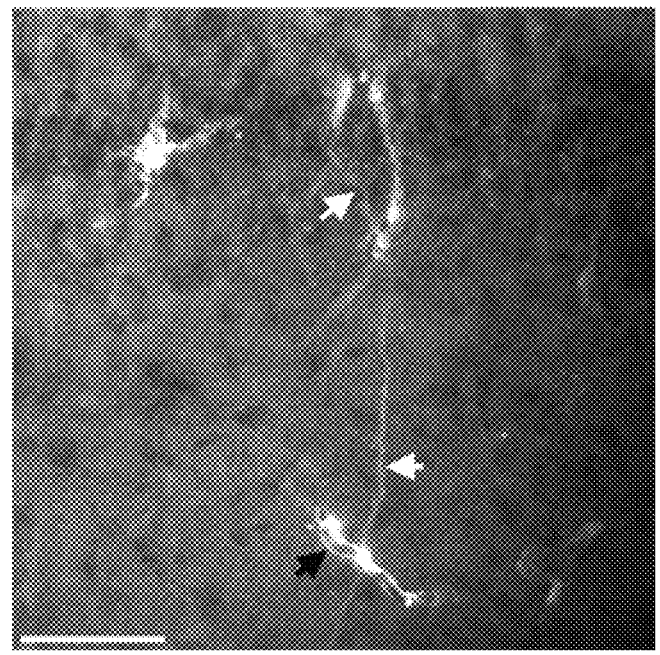

FIGS. 13A-13I illustrate certain aspects of a mouse brain, prepared in accordance with the exemplary methods described herein. Fluorescence images depicting delivery of dextrans at distinct molecular weights, spatially homogenous delivery, and outlines of neuronal axons are shown. The left ROI of the brain was sonicated in the presence of microbubbles and fluorescently-tagged (FIGS. 13A and 13D-13H) 3-, (FIG. 13B) 10-, and (FIG. 13C) 70-kDa dextrans. Diffuse fluorescence regions can be observed for all dextrans, whereas spots of high fluorescence are only observed with the 70-kDa dextran. Pulsing in bursts using a 3.5-cycle pulse length allowed for a homogeneous and diffuse spatial distribution of 3-kDa dextran to the target ROI, shown in FIGS. 13D-13F. FIG. 13F is a zoomed image of the white square in FIG. 13E, which is subsequently a zoomed image of the white square in FIG. 13D. As shown in the graph of FIG. 13G, subregions within the hippocampus displayed difference in NOD. FIGS. 13H and 13I show that, in some brains, the morphology of neurons and vessels can be observed to have increased fluorescence over high levels of diffuse fluorescence. FIG. 13I is a zoomed image of FIG. 13H using confocal microscopy. As shown, axons (white arrows) and a capillary (black arrow) are observed. The bars in FIGS. 13A and 13I depict 1 mm and 50 μm, respectively. An asterisk indicates an increase in left hemispheric NOD per pixel ($P<0.05$) relative to the stratum pyramidale. The bar in FIG. 13A depicts 1 mm. sr, stratum radiatum; sl: stratum lucidum; sp: stratum pyramidale; so: stratum orien.

Table 1 below illustrates the results of another experiment preformed on ninety-nine male mice (strain: C57Bl6; 24.71±1.77 g) in accordance with the exemplary methods described herein and the procedures of the Columbia University Institutional Animal Care and Use Committee. Table 1 illustrates eighteen different experimental conditions, varying the microbubble concentration (μL/g of body mass), the PRF (Hz), and the PL (ms). The results are shown in terms of the NOD (mean±s.d.×$10^9$) and the number of mice with delivered dextran. The first entry corresponds to a sham mouse, where no ultrasound was applied; in the second entry the microbubbles and dextran were administered 1 minute before a 30-second sonication; and in the final entry the microbubbles were injected over a 180 second period. In the remaining entries the mice were intravenously injected with a solution of dextran and microbubble 1 minute after the start of an 11-minute sonication. All sonications were performed with an 1.525 MHz acoustic beam and at a peak-rarefactional pressure of 0.46 MPa.

TABLE 1

| Microbubble concentration (μL/g of body mass) | Pulse repetition frequency (Hz) | Pulse length (ms) | NOD × 1e9 (mean ± std. dev.) | Number of mice with delivered dextran |
|---|---|---|---|---|
| 0.05[a] | — | — | 0.01 ± 0.23 | 0/5 |
| 0.05[b] | 10 | 20 | 4.91 ± 0.94 | 5/5 |
| 0.05 | 10 | 20 | 4.45 ± 2.08 | 5/5 |
| 0.01 | 10 | 20 | 2.89 ± 1.99 | 5/5 |
| 0.25 | 10 | 20 | 5.34 ± 2.12 | 5/5 |
| 0.05 | 0.1 | 20 | −0.17 ± 0.17 | 0/5 |
| 0.05 | 1 | 20 | 3.77 ± 4.52 | 3/5 |
| 0.05 | 5 | 20 | 4.21 ± 2.05 | 5/5 |
| 0.05 | 25 | 20 | 4.58 ± 1.40 | 5/5 |
| 0.05 | 10 | 0.03 | 0.78 ± 1.41 | 2/5 |
| 0.05 | 10 | 0.1 | 1.20 ± 1.05 | 5/6 |
| 0.05 | 10 | 0.2 | 0.98 ± 0.67 | 5/5 |
| 0.05 | 10 | 1 | 4.07 ± 3.71 | 5/5 |
| 0.05 | 10 | 2 | 1.84 ± 1.44 | 4/5 |
| 0.05 | 10 | 10 | 4.76 ± 2.03 | 5/5 |
| 0.05 | 10 | 30 | 5.77 ± 1.73 | 5/5 |
| 0.05 | 5 | 0.2 | 2.02 ± 1.38 | 5/5 |
| 0.05[c] | 5 | 0.2 | 1.58 ± 1.37 | 5/5 |

[a]Sham mouse. No ultrasound was applied.
[b]Microbubble and dextran were administered 1 minute before a 30-second sonication.
[c]Microbubbles were injected over 180 seconds.

Table 2 below illustrates the results of another experiment preformed on ninety-five C57Bl6 male mice in accordance with the exemplary methods described herein and the procedures of the Columbia University Institutional Animal Care and Use Committee. Table 2 illustrates eighteen different experimental conditions, varying the PRF (kHz), BRF (Hz), the BL (# of pulses) and the peak-rarefactional pressure. The results are shown in terms of the NOD (mean±s.d.×$10^9$) and the number of mice with an incidence of NOD increase, calculated as detailed above. Those entries marked with an asterisk (*) correspond to sham mice, where no ultrasound was applied and those entries marked with a double asterisk (**) correspond to parameters where pulses were emitted continuously and without bursts. For all entries the sonication was for 11 minutes at a center frequency of 1.5 MHz, in the presence of systemically administered Definity® microbubbles (0.05 μl/g of body mass) and fluorescently-tagged dextran (molecular weight: 3 kDa, fluorescent tag: Texas Red®) and the PL was 3.5 cycles (2.3 μs).

TABLE 2

| Pulse repetition frequency (kHz) | Burst repetition frequency (Hz) | Burst length (# of pulses) | Peak-rarefactional pressure | NOD × 1e9 (mean ± std. dev.) | Incidence of NOD increase |
|---|---|---|---|---|---|
| *— | *— | *— | 0 | 0.02 ± 0.19 | 0/3 |
| 100 | **— | **— | 0.51 | 0.21 ± 0.32 | 1/3 |
| 100 | 10 | 1000 | 0.51 | 2.01 ± 1.44 | 3/3 |
| 100 | 5 | 1000 | 0.51 | 6.14 ± 1.45 | 3/3 |
| 100 | 2 | 1000 | 0.51 | 3.08 ± 2.76 | 3/3 |
| 100 | 1 | 1000 | 0.51 | 1.45 ± 0.73 | 3/3 |
| 100 | 0.1 | 1000 | 0.51 | 0.99 ± 0.85 | 2/3 |
| 25 | **— | **— | 0.51 | 0.30 ± 0.20 | 1/3 |
| 25 | 10 | 1000 | 0.51 | 1.31 ± 1.35 | 2/3 |
| 25 | 5 | 1000 | 0.51 | 1.48 ± 0.77 | 3/3 |
| 25 | 2 | 1000 | 0.51 | 3.34 ± 1.35 | 3/3 |
| 25 | 1 | 1000 | 0.51 | 1.92 ± 0.10 | 3/3 |
| 25 | 0.1 | 1000 | 0.51 | 0.35 ± 0.10 | 2/3 |
| 6.25 | **— | **— | 0.51 | −0.11 ± 0.35 | 1/3 |
| 6.25 | 5 | 1000 | 0.51 | 0.56 ± 0.95 | 2/3 |
| 6.25 | 2 | 1000 | 0.51 | −0.16 ± 0.67 | 1/3 |
| 6.25 | 1 | 1000 | 0.51 | 0.78 ± 0.85 | 2/3 |
| 6.25 | 0.1 | 1000 | 0.51 | 0.68 ± 0.47 | 2/3 |
| 100 | 5 | 1000 | 0.37 | 0.60 ± 0.48 | 2/3 |
| 100 | 5 | 1000 | 0.25 | 0.10 ± 0.16 | 1/3 |

TABLE 2-continued

| Pulse repetition frequency (kHz) | Burst repetition frequency (Hz) | Burst length (# of pulses) | Peak-rarefactional pressure | NOD × 1e9 (mean ± std. dev.) | Incidence of NOD increase |
|---|---|---|---|---|---|
| 100 | 5 | 1000 | 0.13 | 0.10 ± 0.21 | 1/3 |
| 100 | 5 | 500 | 0.51 | 3.30 ± 0.58 | 3/3 |
| 100 | 5 | 100 | 0.51 | 3.60 ± 0.95 | 3/3 |
| 100 | 5 | 50 | 0.51 | 2.20 ± 0.54 | 3/3 |
| 100 | 5 | 10 | 0.51 | 2.14 ± 1.33 | 3/3 |
| 100 | 5 | 5 | 0.51 | 0.13 ± 0.17 | 1/3 |
| 100 | 5 | 1 | 0.51 | 0.01 ± 0.11 | 0/3 |

*Sham mice where no ultrasound was applied.
**Parameters where pulses were emitted continuously and without bursts.

As illustrated in Table 2, emission of a continuous train of pulses at 0.51 MPa and a PRF of 6.25, 25, and 100 kHz produced no significant increase in NOD, which is a measure of the relative increase in fluorescence in the left (target) ROI relative to the right (control) ROI. Under each condition, only 1 out of 3 mice had an increase in NOD, and in these instances, the fluorescence was faint and distributed along or near large vessels. Select intervals were evaluated by grouping 1000 pulses into bursts and emitting them at a BRF of 0.1, 1, 2, 5, or 10 Hz, which corresponded to a burst repetition period (BRP) of 10, 1, 0.5, 0.2, and 0.1 s, respectively. At a 100-kHz PRF, significant increases in NOD were observed at 1 and 5 Hz, while no increase was observed at 0.1, 2, and 10 Hz. At a 25-kHz PRF, significant increases were observed at 1, 2, and 5 Hz, while no increase was observed at 0.1 and 10 Hz. At a 6.25-kHz PRF no significant increase was observed at any of the BRFs evaluated although some mice had observable increases in fluorescence. In general and as illustrated in Table 2, the NOD increased with the interval between bursts and then decreased beyond a particular duration. Also, both the level and incidence of NOD decreased with the PRF. The maximum average NOD increase was observed with a 100-kHz PRF and a 5-Hz BRF.

Table 2 further illustrates the dependence of acoustic peak-rarefactional pressure on BBB disruption was evaluated in a sham (0 MPa) and pressures of 0.13, 0.25, 0.37, and 0.51 MPa. A significant increase in NOD was only observed at 0.51 MPa. Although 0.37 MPa had no significant increase in NOD, 2 out of 3 mice had detectable levels of fluorescence. Therefore, the pressure threshold for BBB disruption for a 3.5-cycle pulse was between 0.25 and 0.51 MPa. The effect of BL was evaluated from 1 to 1000 pulses. A single pulse was insufficient in disrupting the BBB. The lowest pressure show feasible in disrupting the BBB was at 5 pulses and was observed in 1 out of 3 mice. A significant increase in NOD was observed from 50 pulses and higher. In general, increasing the number of pulses increased the likelihood and magnitude of NOD increase.

In an experiment using a 100-kHz PRF, a 5-Hz BRF, a 0.51 MPa pressure and a 1000 pulse BL, the relevance of the pulse-sequence to pharmacologically-sized agents was evaluated with dextrans at molecular weights of 3-, 10-, and 70-kDa. Significant increases in NOD were observed using 3 and 70 kDa dextrans. The 10-kDa dextran was successfully delivered in all 3 mice, but the increase was not as significant (P=0.06). The 3-kDa agent was distributed most homogeneously and across a larger area than the other two molecular weights. The distribution of 10-kDa was diffuse as well, but did not extend spatially as far as the 3-kDa dextran. The 70-kDa dextran had heterogeneous spots of high levels of fluorescence on top of diffusely distributed fluorescence. In certain instances, when high concentrations of 3-kDa dextran were diffusely delivered to the target ROI, the morphology of neurons and/or glial cells can be seen.

For example and as illustrated in FIGS. 13H and 13I, at a PRF of 100 kHz, a BL of 1000 pulses, and a BRF of 2 Hz, a neuronal axon with an approximately 1 μm diameter can be observed extending from its cellular body and attached to a capillary, which had a diameter for approximately 4.5 μm.

Example 2

In another exemplary experiment, the efficacy of the FUS method described herein is shown by accomplishing two objectives after BBB opening: 1) diffusion of brain-derived neurotrophic factor (BDNF) across the BBB and containment of BDNF within the targeted region, i.e., the hippocampus and 2) associated activation of the BDNF receptor and its downstream signaling molecules in neurons, illustrating bioactivity of the functional BDNF upon delivery.

To visualize the passage of BDNF across the BBB, the fluorescent dye Alexa Fluor 594 was conjugated to BDNF prior to the experiments. The fluorescent tag is expected to not modify the transport properties of BDNF given its relatively small molecular weight (~0.3 kDa) compared to the BDNF's (27 kDa). Following successive application of FUS sonication (for example as shown in FIGS. 4C and 5), microbubble injection, and intravenous injection of BDNF, the mice (n=3) were sacrificed 20-30 min post-sonication for histological analysis 1) to allow for the BDNF to accumulate in the BBB-opened region and facilitate detection of the compound (higher fluorescent intensity) at the sonicated areas; 2) to allow the compound to circulate through the microvasculature before being cleared by the venous system, since circulating BDNF has a half-life of less than 10 min; and 3) to allow for the downstream signaling cascade to be activated. The activation of the BDNF receptor, TrkB, can occur within seconds of BDNF delivery.

Animals

A total of seven C57Bl6 male mice were used for this study (17.6-23.0 g, Harlan Laboratories). The animals were anesthetized with a mixture of oxygen (0.8 L/min at 1.0 Bar, 21° C.) and 1.5-2.0% vaporized isoflurane (Aerrane, Baxter Healthcare) using an anesthesia vaporizer (SurgiVet, Smiths Group). The mouse's vital signs were monitored continuously and isoflurane was adjusted throughout the experiment as needed. The Columbia University Institutional Animal Care and Use Committee (IACUC) gave approval for the mouse studies.

The total number of mice used in the BDNF study was seven (n=7) as follows: three mice were injected with BDNF, sonicated and sacrificed after 20-30 min for both IHC & fluorescence analysis, one mouse was injected with BDNF, sonicated and sacrificed but died after 3 min (IHC and fluorescence analysis were also performed but discounted in the statistical analysis) and three controls were sonicated and sacrificed after 20-30 min (No BDNF) for IHC analysis. Three types of "controls" were used to show the effect of sonication on the BDNF permeation through the blood-brain barrier and subsequent activation of the downstream signaling cascade as follows:

a) to demonstrate the difference between the left (sonicated) hippocampus and the right (non-sonicated) hippocampus in four mice (three mice sacrificed after 20-30 min, one died after 3 min) following BDNF injection and sonication;

b) to demonstrate no difference between the left (sonicated) hippocampus and the right (non-sonicated) hippocampus in three control mice following only sonication (no BDNF) so as to rule out the effect of sonication alone on signaling cascade activation; and c) to obtain negative controls for the IHC analysis in all studied mice, where no primary antibody was added to the sections.

The statistical analysis was based on the three BDNF-injected mice that were sacrificed after 20-30 min, and did not include the 3-min mouse case. The results for the case of 3-min BDNF-injected mouse are also presented for comparison in terms of the downstream signaling activation and its time dependence in order to support previous reports on the temporal sequence of signaling cascades downstream of BDNF. The BDNF was injected into the femoral vein 10-min after sonication while the mice were still anesthetized. There was at least 3 min (1 mouse) and 20-30 min (3 mice) of circulation before PBS transcardial perfusion was started.

Neurotrophic Factors

Brain-Derived Neurotrophic Factor (BDNF)

The Brain-Derived Neurotrophic Factor (BDNF) conjugated to Alexa Fluor® 594 dye was used (Invitrogen Corp, Carlsbad, Calif., USA). BDNF Human Recombinant was produced in *Escherichia Coli* and is a homodimer, non-glycosylated, polypeptide chain containing 2×119 amino acids with a total molecular mass of 27 kDa. According to the supplier, it was purified by proprietary chromatographic techniques and the sequence of the first five N-terminal amino acids was determined and found to be Met-His-Ser-Asp-Pro. Biological activity was determined by evaluating ED50 (50 ng/ml), calculated by the dose-dependent induction of ACHE (acetylcholine esterase) in rat basal forebrain primary septal culture. The compound (6.0 mg) was custom conjugated to Alexa Fluor® 594 dye (~1:1 molar ratio) and provided in a fine lyophilized powder. The vials were stored under −18° C. until use.

Glial-Derived Neurotrophic Factor (GDNF) and Neurturin (NTN)

A total of 12 mice received FUS followed by GDNF (40-90 mg/kg in 0.15 ml PBS, n=10), as well as NTN (20 mg/kg in 0.2 ml PBS, n=2) injections. Two mice were used for the NTN study. Both GDNF and NTN were conjugated with Alexa Fluor® 488 fluorescent dye. Four sites within a 1 mm square in the caudate were sonicated at a frequency of 1.5 MHz, with a pulse length of 15,000 cycles (n=3) and 30,000 cycles (n=8), at varying pressures. Detailed acoustic parameters were shown in Table 3.

TABLE 3

FUS parameters used in the case of GDNF and NTN

| Compound | GDNF | | | | | | | | | NTN |
|---|---|---|---|---|---|---|---|---|---|---|
| PL (cycles) | 15,000 | | | 30,000 | | | | | | 30,000 |
| P-N pressure | 0.30 | 0.45 | 0.60 | 0.30 | 0.45 | | 0.60 | | | 0.60 |
| Circulation time | 45 | 180 | 180 | 60 | 60 | 6. | 4 | 3 | 6 | 6 | 30 |

In the case of 6.5 minutes circulation time, blood was drawn after 45 seconds to confirm the circulation and fluorescence of the protein. Brain, liver, kidney, and testes were extracted and fixed for frozen section. Organs were then frozen into blocks and sectioned at 100 μm to potentially locate GDNF.

Ultrasound

A single-element spherical segment FUS transducer (center frequency: 1.525 MHz; focal depth: 90 mm) was driven by a function generator (Agilent Technologies) through a 50-dB power amplifier (ENI) to generate therapeutic ultrasound waves. A pulse-echo transducer (center frequency: 7.5 MHz; focal length 60 mm) was positioned through a center hole of the FUS transducer so that the foci of the two transducers were aligned. It was driven by a pulser-receiver system (Panametrics) connected to a digitizer (Gage Applied Technologies) and was used for imaging. A cone filled with degassed and distilled water and capped with an acoustically transparent polyurethane membrane was mounted on the transducer system (FIG. 5). The transducers were attached to a computer-controlled 3D positioning system (Velmex). The FUS transducer's pressure amplitude reported in this Example was previously measured with a needle hydrophone (needle diameter: 0.2 mm; Precision Acoustics) in degassed water while accounting for 18.1% attenuation by the mouse skull. The dimensions of the beam were measured to have a lateral and axial full-width at half-maximum (FWHM) intensity of approximately 1.32 and 13.0 mm, respectively.

Targeting Procedure

The head of each anesthetized mouse was immobilized using a stereotaxic apparatus. The fur on top of the head was removed with an electric razor and a depilatory cream. After applying ultrasound gel, a water bath with its bottom made of an acoustically and optically transparent membrane was placed on top of the head and gel. A grid positioning method to target the mouse hippocampus was then used as previously described. In brief, a metallic grid was placed in alignment with the mouse skull's sutures, which were visible through the intact scalp of the mouse after hair removal. The left hippocampus was localized by identifying the sagittal suture and then moving 2.5 mm to the left of that suture and subsequently 3 mm in depth from the top of the skull. The grid was removed immediately after targeting was completed and prior to FUS application as to prevent interference with the sonication. Four target sonication locations were identified relative to the sutures. The first target overlapped the medial portion of the hippocampus, the lateral portion of the thalamus, and the posterior cerebral artery (PCA). The transducer was then moved 1 mm anterior and 1 mm lateral for the second target and then 1 mm posterior for the third. The fourth and final target was 1 mm medial and 1 mm anterior. In the end, four different locations were targeted at the corner of a 1 mm×1 mm square.

Sonication Protocol

BDNF

Definity® microbubbles (diameter: 1.1-3.3 μm, vial concentration: 1.2×10¹⁰ bubbles/mL; Lantheus Medical Imaging) were composed of octafluoropropane gas encapsulated in a lipid shell were diluted (1:20) in phosphate-buffered saline (PBS) and then administered into the tail vein (final administered concentration: 50 μl/kg of body mass). This dosage is exemplary, however, it is recognized that different bubble concentrations can be used in accordance with the disclosed subject matter. For example, a clinical dose, which can be about five times lower, can be used in accordance with the disclosed subject matter. One minute after injection, pulsed-wave FUS (peak-rarefactional pressure: 0.46 MPa; pulse repetition frequency: 10 Hz; pulse length: 20 ms) was applied. Each of the four target locations was sonicated twice, resulting in a total of 8 sets of 30 s sonication with a 30 s delay between each set.

GDNF and NTN

The sonication parameters are provided in Table 3. All other parameters used were the same as in the case of BDNF.

Administration, Perfusion, and Sectioning

A bolus injection of BDNF compound via the femoral vein was followed 10 minutes after sonication (40-90 mg/kg of mouse body mass in 0.2 ml PBS). Except for one animal that died 3 minutes after injection and was perfused immediately, the rest of the animals were sacrificed 20-30 minutes after the injection to allow for adequate circulation. The animals were transcardially perfused with phosphate buffered saline (4-5 min.) and 4% paraformaldehyde (7-8 min) at a flow rate of 6.8 ml/min. Next, the skulls were removed and immersion-fixed for 24 hours before extracting the brains. Extracted brains were fixed again in 4% paraformaldehyde for 24 hours, and transferred to 10% (30 min), 20% (60 min), and 30% (24 hr) sucrose solution for cryoprotection. Brain samples were then embedded in an Optimal Cutting Temperature (OCT) medium and were frozen using dry ice and isopentane. Frozen blocks were sectioned horizontally at 10-150 μm thickness for fluorescent imaging and at 5-10 μm thickness for immunohistochemistry. Slices covering the entire hippocampus were selected, placed on a slide, and stored in −18° C. freezer for later analysis. In each case, the right hippocampus is not sonicated and therefore serves as the control to the left hippocampus, which is sonicated.

Immunohistochemistry

Immunohistochemistry was performed only in the case of BDNF. Five primary antibodies were used: two against phosphorylated TrkB receptor (p-Y816 rabbit polyclonal [ab75173] and p-Y515, rabbit polyclonal [ab51187]) purchased from Abcam Inc. (Cambridge, Mass.), and three against phosphorylated Akt (p-S473 rabbit monoclonal [#4060]), phosphorylated MAPK (p-T202/T204 rabbit monoclonal [#4370]), and phosphorylated CREB (p-S133 rabbit monoclonal [#9198]), all purchased from Cell Signaling Technology (Danvers, Mass.). Slides containing thin frozen sections (5-10 μm) were dried and placed in a citrate buffer (pH 6.0) for antigen retrieval using a microwave. Slides were allowed to cool for 20 minutes prior to a PBS rinse (3×5 min) and then incubated in 0.3% hydrogen peroxide in PBS (five min) to block endogenous peroxidase activity. Slides were washed again in PBS (3×5 min) and blocked in 10% normal goat serum with 0.1% BSA for 20 minutes. After blocking solution was removed, the primary antibodies were diluted in DAKO antibody diluent solution (1:50-1:300) and incubated for 60 minutes at room temperature. Slides were washed in PBS for five min and incubated with biotinylated secondary antibody (goat anti-rabbit 1:200; Vector Laboratories, Burlingame, Calif.) for 30 minutes at room temperature. Slides were washed again in PBS (3×5 min) and VECTASTAIN® ABC reagent was added to the sections for 30 minutes (A: 1:60, B: 1:60 in PBS mixed 30 min prior to use). Slides were washed in PBS (3×5 min) and peroxidase substrate solution DAB (DAKO, Carpinteria, Calif.) was added to sections (1 drop of DAB in 1 ml buffer). Slides were immersed in dH2O as soon as color developed. Sections were counterstained with hematoxylin, cleared and dehydrated with alcohols and xylene, and covered with Permount™ mounting medium (Thermo Fisher Scientific, Inc Waltham, Mass., U.S.A.), and a glass coverslip.

Bright-Field and Fluorescent Microscopy

Bright-field and fluorescent images were acquired using a light and fluorescence microscope (BX61; Olympus, Melville, N.Y., USA) with a filter set at excitation and emission wavelengths of 595 nm and 615 nm, respectively.

Quantification

Bright field images were white corrected with same correction for both right (control) and left (sonicated) images. Diaminobenzidine (DAB) stain density was then extracted from the bright field images using a color deconvolution method and implemented in Matlab (Mathworks, Natick, Mass.) by the Open Microscopy Environment project (OME, www.openmicroscopy.org). H&E DAB built-in vectors were used for the deconvolution step. Where DAB is uptaken, the cellular region in question turns brown. For each image, the mean stain intensity was computed using the logarithm of the stain intensity. Image artifacts (folded tissue, holes or stain droplets) were manually segmented in each image and removed from the analysis. For each mouse and each antibody, the percentage change (PC) of the stain intensity between the left and the right sides was then computed as follows: PCI=100 [(ILeft−IRight)/IRight]

Statistical Analysis

Statistical analysis was performed using a two-tailed Student's t-test to determine whether the BDNF concentration is significantly increased in the sonicated (left hippocampus) region compared to the BDNF concentration in the unsonicated (right hippocampus) region. A $p<0.05$ was considered significant in all comparisons.

Results

Figure 14A:
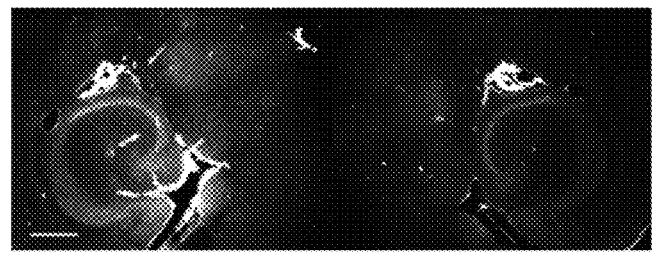
FIGS. 14A-14E illustrate images of a mouse brain subjected to sonication in accordance with an exemplary embodiment of the disclosed subject matter.
Figure 14B:
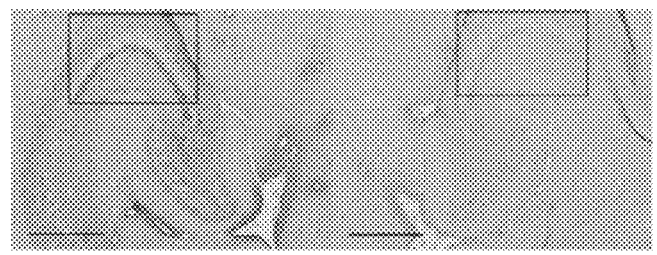
Figure 14C:
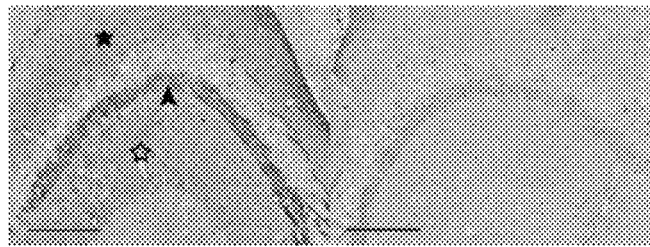
Figure 14D:
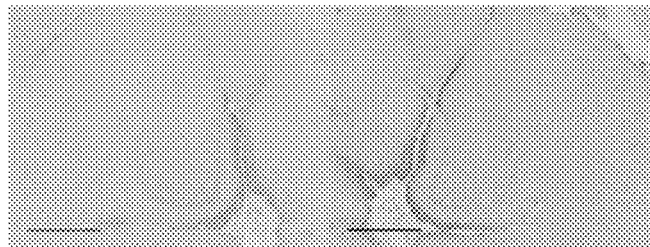
Figure 14E:
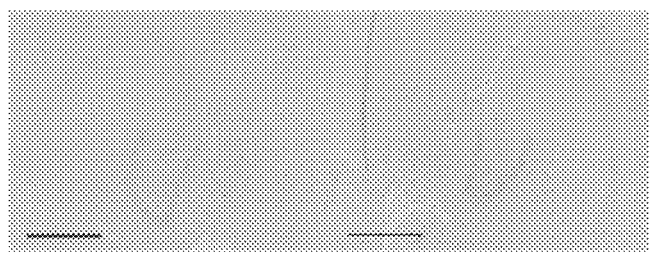

FIG. 14A shows a fluorescent image of a 100-micron frozen brain section from a mouse that was sacrificed 20 min after sonication. The sonicated hippocampus (left) shows much higher fluorescent intensity than the un-sonicated hippocampus (right), depicting blood-brain barrier opening and the extravasation of fluorescent-tagged (Alexa Fluor 594) BDNF in the sonicated region; FIG. 14B shows a 5-micron frozen section from the same mouse was immunohistochemically stained using a primary antibody against phosphorylated MAPK (pMAPK). Consistent with the fluorescent image in FIG. 14A, the intensity of DAB staining is much greater in the left sonicated hippocampus compared to the right control; the black box shows the enlarged area in FIG. 14C, where immunoreactivity to pMAPK is shown in mossy fiber terminals (arrowhead), suprapyramidal CA3 dendrites (black star), and the axons of the Schaffer collateral system (hollow star); FIG. 14D shows immunohistochemical staining of a 5-micron frozen section from a mouse that was sacrificed 3 min after sonication; the same primary antibody against pMAPK was used. No difference in DAB intensity is shown between the sonicated and the control hippocampus, i.e., the 3-min case did not show significantly greater immunoreactivity to MAPK in the sonicated region in contrast to all three 20-30 min mice that did in FIGS. 14B-14C; FIG. 14E shows negative control performed at the same time and for the same mouse as in FIG. 14A; no primary antibody (against pMAPK) was added to this 5-micron frozen section during the staining procedure. All magnifications are 40× and scale bars are 500 μm except for FIG. 14C, which is 100× and 200 μm, respectively.

FIG. 14A shows the diffusion of BDNF at the sonicated region in the left hippocampus as detected by fluorescent intensity of Alexa Fluor 594 (mouse sacrificed 20 min after BDNF injection). A difference can be shown in fluorescent intensities between the sonicated hippocampus (left) and the control un-sonicated hippocampus (right). Regions of greater intensity included parts of the thalamus, the transverse hippocampal artery and its branches inside the hippocampus, the neurons in the pyramidal (CA1-CA3) layers of the hippocampus proper, and the neurons in the hilus and granular layers of the dentate gyrus. FIGS. 14B-14C depict the extent of immunoreactivity to phosphorylated MAPK (activated molecule downstream of BDNF signaling; discussed below) in a DAB-stained section that was sectioned ~300 μm dorsally from the frozen section imaged in FIG. 14A. The DAB-stained regions closely matched the areas of BDNF diffusion, providing a multi-modality confirmation of BDNF delivery across the BBB. Similar DAB intensity was observed in the case of the mouse sacrificed 3 min after sonication (FIG. 14D) and the negative control for the case in FIG. 14A, i.e., no primary antibody added (FIG. 14E).

To demonstrate post-delivery bioactivity of the BDNF compound, immunohistochemical techniques were utilized to detect activated downstream signaling molecules using two primary antibodies against the activated TrkB receptor (pTrkB Y816 and pTrkB Y515), and three primary antibodies against the phosphorylated MAPK (T202-T204), phosphorylated CREB (S133), and phosphorylated Akt (S473). The relative activation of these signaling molecules in sonicated vs. non-sonicated hippocampi of both BDNF-administered (N=3) and control mice (N=3) were quantified by measuring the DAB stain intensity as described herein.

Figure 15A:
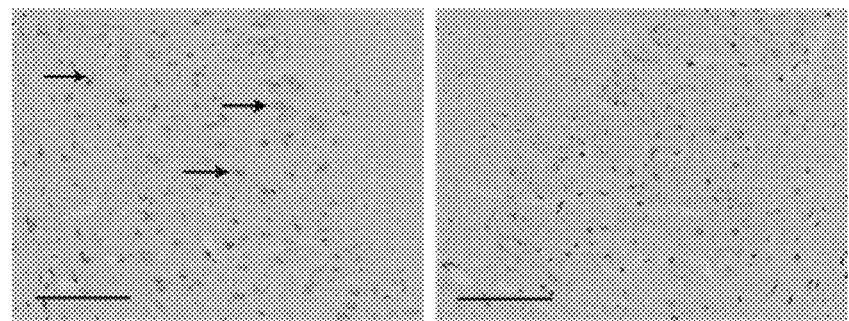
FIGS. 15A-15D illustrate images of a mouse brain subjected to sonication in accordance with an exemplary embodiment of the disclosed subject matter.
Figure 15B:
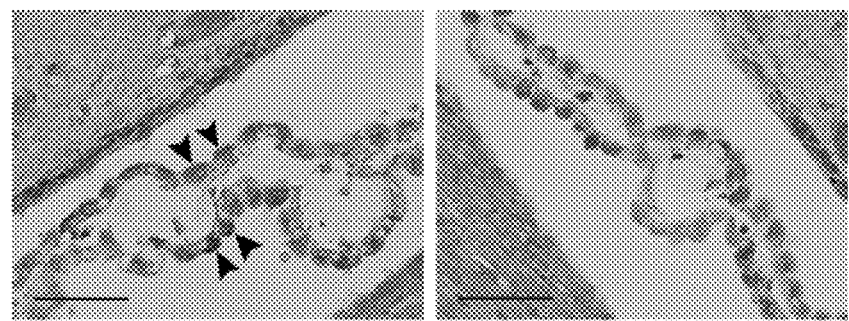
Figure 15C:
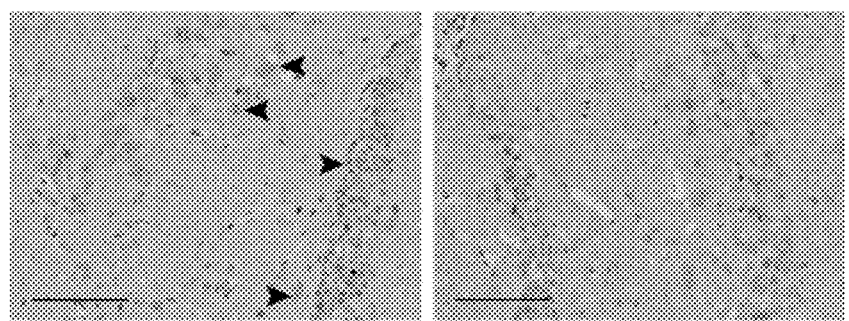
Figure 15D:
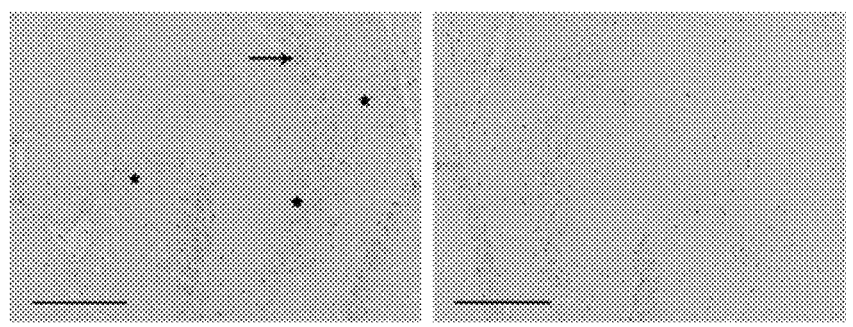

FIGS. 15A-15D show immunohistochemical staining of 5-micron frozen sections using a primary antibody against phosphorylated TrkB 816 (FIGS. 15A-15C) and a primary antibody against phosphorylated TrkB 515 (d). Mice were sacrificed 20-30 min (FIGS. 15A, 15B, and 15D) or 3 min (FIG. 15C) after sonication. The difference in DAB intensity between the sonicated hippocampus (left column) and the contralateral control hippocampus (right column) is detectable in all the sections (FIGS. 15A-15D). In FIGS. 15A and 15B, the 20-30 min mice show increased DAB intensity in the presence of TrkB 816, although, in contrast to MAPK and CREB, a lower proportion of the sections showed notable differences between the left and right hippocampus. FIG. 15B shows a difference in the DAB intensity in the choroid plexus of left vs. right. hippocampus given that the former is stained in brown (examples of DAB staining are indicated by the arrows) while the latter is only stained in blue. In FIG. 15C, the 3-min-circulation case shows increased DAB intensity in the presence of TrkB 816. The immunoreactivity to pTrkB is shown at the plasma membrane of neuronal cells in CA1 region (arrows in FIG. 15A), ependymal cells of choroid plexus (arrowheads in FIG. 15B), neuronal cells in hilus and granular layers of dentate gyrus (arrowheads in FIG. 15C), and at the plasma membrane of pyramidal neurons (arrow in FIG. 15D) and axons (stars in FIG. 15D). Magnifications and scale bars are 400× and 50 µm (FIG. 15B), 200× and 100 µm (FIGS. 15A and 15C), and 100× and 200 µm (FIG. 15D), respectively.

Figure 16A:
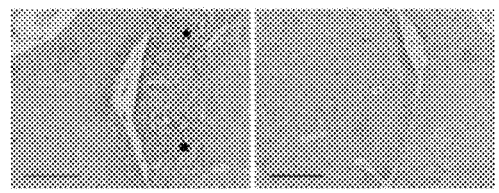
FIGS. 16A-16F illustrate images of a mouse brain subjected to sonication in accordance with an exemplary embodiment of the disclosed subject matter.
Figure 16B:
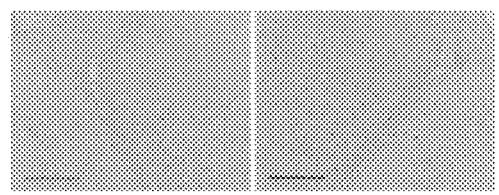
Figure 16C:
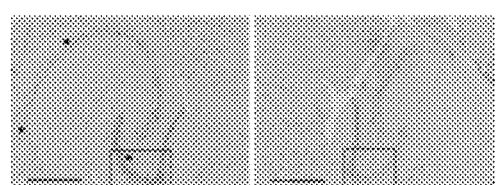
Figure 16D:
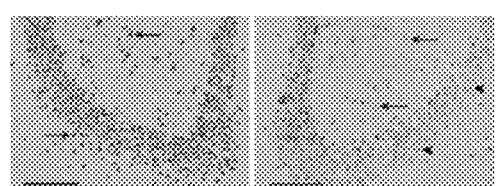
Figure 16E:
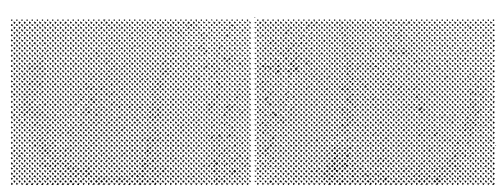
Figure 16F:
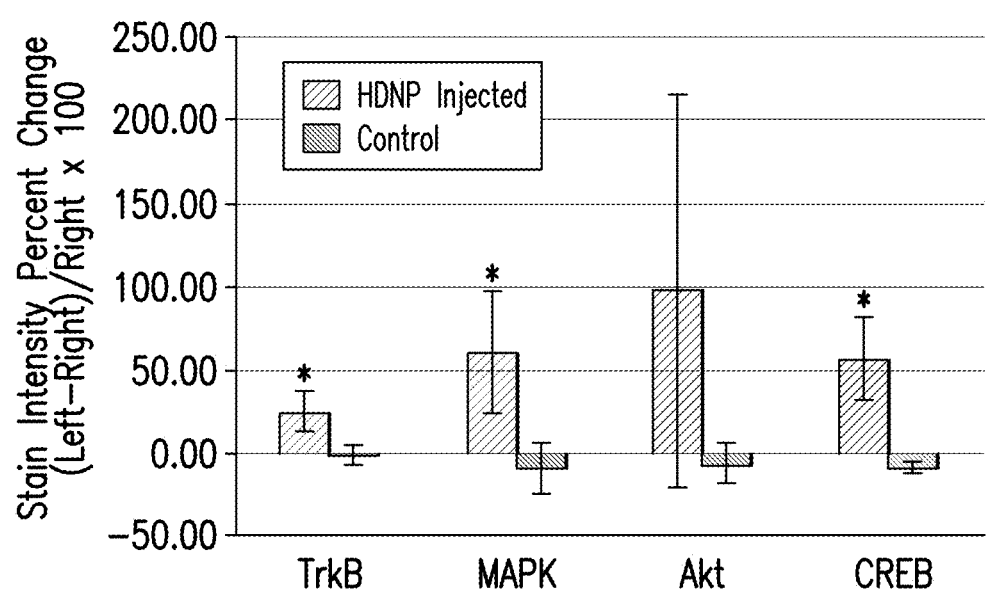

FIGS. 16A-16F show immunohistochemical staining of 5-micron frozen sections using primary antibodies against phosphorylated Akt (FIGS. 16A and 16B) and phosphorylated CREB (FIGS. 16C-16E). Mice were sacrificed 20 min (FIGS. 16A, 16C, and 16D) or 3 min (FIGS. 16B and 16E) after sonication. The box in FIG. 16C shows the enlarged area in FIG. 16D. Difference in DAB intensity between sonicated regions (left images) and the contralateral control (right images) is observable in the 20 min samples (FIGS. 16A, 16C, and 16D; black stars). The greater intensity of the DAB stain in the sonicated region is especially noticeable in the thalamus in the case of pAkt (stars in FIG. 16A), and in the CA1 region of hippocampus (the left two stars in FIG. 16C), and in neuronal cells of the hilus and granular layers of dentate gyrus in the case of pCREB (arrows in FIG. 16D, left image). Contrast these findings with the minimal or lack of DAB staining in neuronal cells of the hilus and granular layers of dentate gyrus in the control un-sonicated hippocampus (arrows and arrowheads in FIG. 16D, right image, respectively). Magnifications and scale bars are 40× and 500 µm in FIG. 16C, 100× and 200 µm in FIGS. 16A-16B and 16E, and 200× and 100 µm in FIG. 16D, respectively. In FIG. 16F, immunohistology stain intensity analysis shows percentage change between the left (FUS) and the right (no FUS) sides of the mice brains. A significant difference ($p<0.05$, N=3; depicted by asterisks) was found between the BDNF administered animal group and the control (no BDNF) animal group for the TrkB, MAPK, and CREB antibodies. Bars represent mean±standard deviation.

Across all BDNF-administered mice (sacrificed 20-30 min post-sonication), immunoreactivity to each activated signaling molecule displayed a distinct characteristic stain that was unique and easily identifiable among various brain slices. FIGS. 15A-15D demonstrate the greater presence of immunoreactivity to pTrkB Y816 (FIGS. 15A-15C) and pTrkB Y515 (FIG. 15D) in the sonicated brain regions (left column) compared to the non-sonicated contralateral regions (right column). On the sonicated side, DAB staining can be seen on neuronal cell membranes in the hilus and granular layers of the dentate gyrus (FIG. 15C), CA1 (FIG. 15A) and CA3 (FIG. 15D) regions of the hippocampus, and on the ependymal cell membranes of the choroid plexus in the adjacent lateral ventricle (FIG. 15B). Such difference in DAB intensity was not apparent in all the sections, but only in some, probably due to loss of TrkB phosphorylation state after the 20-30 min delay in sacrificing the mice post-sonication and BDNF injection. On the other hand, there was strong immunoreactivity to pMAPK and pCREB in the sonicated left hippocampus of BDNF-administered mice in most of the sections analyzed 20-30 min post-injection. The temporal sequence of phosphorylation in downstream signaling molecules can be demonstrated when the results are compared to those of the mouse expiring 3 min post-sonication. In those 3-min cases, the difference in DAB intensity between the left sonicated hippocampus and the control was observed in the case of the pTrkB antibody (FIG. 15C), but not in pMAPK (FIG. 14D), pAkt (FIG. 16B), and pCREB (FIG. 16E) cases, demonstrating that the BDNF-mediated phosphorylation of the TrkB receptor is faster compared to phosphorylation of downstream molecules. As described herein, immunoreactivity to downstream molecules was more pronounced, but also unique and distinct in the sonicated left hippocampus of >20 min samples. Phosphorylated MAPK was detected in axons and dendrites of the pyramidal and granular neurons, but not in the neuronal cell bodies. pMAPK immunoreactivity was present in the mossy fibers of the CA3 hippocampal neurons (FIGS. 14B-14C). The phosphorylated CREB immunoreactivity was observed in the nuclei and cytoplasm of the neuronal soma in all CA regions and layers of the sonicated hippocampus. With respect to the right (unsonicated) hippocampus (in both the control and BDNF-administered cases), lower levels of pMAPK and pCREB immunoreactivity were detectable (FIGS. 14B-14C and FIGS. 16C-16D, right columns). In the case of pCREB, however, the CA1 region and parts of the granular layers of the dentate gyrus in the right unsonicated hippocampus showed absence of immunoreactivity (FIGS. 16C-16D, right columns).

Figure 17A:
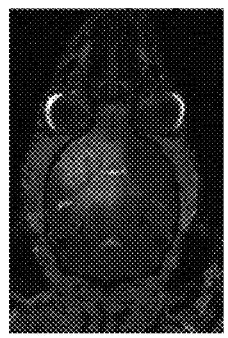
FIGS. 17A-17D illustrate images of a mouse skull subjected to sonication in accordance with an exemplary embodiment of the disclosed subject matter.
Figure 17B:
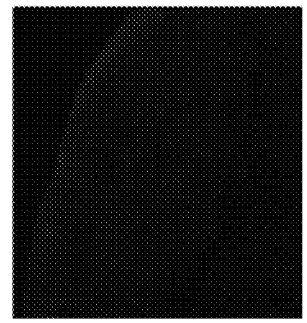
Figure 17C:
Figure 17D:
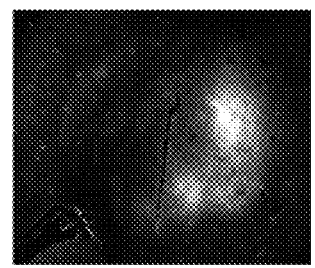

FIGS. 17A and 17C show T1-weighted MR image of the entire mouse head verifying BBB opening using gadolinium enhancement and FIGS. 17B and 17D show fluorescence image magnified in the region of interest where the highest gadolinium enhancement was detected (white rectangle) in two separate murine brains, one with fluorescently tagged (Alexa Fluor) GDNF (Invitrogen, Inc.) in FIGS. 17A-17B and the other with Neurturin (courtesy of Judith P. Golden, Ph.D., Washington University Medical Center and Invitrogen, Inc.) in FIGS. 17C-17D, were systemically administered with the target being the caudate putamen instead of the hippocampus.

According to the statistical results, more significant cascade effects were shown to be triggered in the sonicated regions compared to the contralateral (control) side in all cases, indicative of the fact that a critical BDNF concentration was reached sufficient of triggering these effects. Also, two additional neurotrophic factors that have shown promise in treating Parkinson's disease (both involved in clinical trials), were also tested, namely the glia-derived neurotrophic factor (GDNF) (FIGS. 17A-17B) and neurturin (NTN) (FIGS. 17C-17D) using the same sonication parameters as in the BDNF study but targeting the caudate putamen instead of the hippocampus in two mice as that region is more relevant to Parkinson's. It can be shown that, although all these three proteins can be of similar molecular weight and overall consistency, not all neutrotrophic factors cross the blood-brain barrier after opening with FUS. Neurturin may behave similarly to BDNF permeating through the opened barrier and into the parenchyma (FIGS. 17C-17D); however, GDNF does not (FIGS. 17A-17B). The latter finding was shown in ten mice while the former in two. There may be fewer receptors in the brain for GDNF than for BDNF, i.e., the two proteins on two different transport mechanisms. Also, the GDNF may be broken down in circulation within the first 45 s and upon imaging post-mortem no fluorescence was found in the brain (FIG. 17D), kidneys, liver, bladder or testes. Therefore, GDNF may be undetectable in the brain parenchyma but may also be absent from other organs, indicating potential differences in the GDNF systemic administration compared to those of BDNF and NTN.

In the case of antibodies against pTrkB (Y515 and Y816 results combined), pMAPK, and pCREB, mean percent changes in DAB stain intensity between the left and right hippocampal regions were greater in the BDNF-administered mice (25.22, 60.58, and 56.91%) compared to those in the control mice (−1.36, −9.20, and −8.67%), respectively ($p<0.05$; FIG. 16F). In the case of the pAkt antibody, the mean percent changes in the DAB stain intensity of the BDNF-administered mice and the control mice were similar, although parts of the sonicated thalamus in the BDNF-administered mice showed greater DAB stain intensity than the un-sonicated side in a few sections (FIG. 16A).

Thus, the brain-derived neurotrophic factor (BDNF) can cross the ultrasound-induced blood-brain barrier opening, and can also trigger signaling pathways in the pyramidal neurons of mice in vivo from the membrane to the nucleus. As shown with two additional neurotrophic factors, namely GDNF and NTN, these findings can depend on the pharmacokinetics and other properties of the molecular uptake of the molecule in the brain. However, as the molecule after permeation through the opened BBB triggered a molecular cascade and entered the neuronal nucleus, focused ultrasound in conjunction with microbubbles can generate downstream effects at the cellular and molecular level and thus increase the drug's efficacy and potency in controlling or reversing disease.

Example 3

In another exemplary experiment, the dependence of both the spatial extent and the duration of FUS-induced BBB opening in vivo with different microbubble sizes and peak-rarefactional pressures (PRPs) is shown. Gd-DTPA-BMA retention in the brain parenchyma can be used as a signature of the area of BBB opening. Volumetric quantification of the region of BBB opening can be assessed by measuring the diffusion volume of Gd-DTPA-BMA in the sonicated region of the brain, for example the right hippocampus, detected by the longitudinal signal enhancement. In the experiment, starting with the day of sonication and continuing up to 5 days following sonication, pre and postcontrast enhancement T1-weighted high resolution MR images were consecutively acquired at each timepoint.

Materials and Setup
Ultrasound Setup

Acoustic waves used were generated by a single-element, spherical-segment FUS transducer (center frequency: 1.5 MHz, focal depth: 60 mm, radius: 30 mm; Imasonic, France), which was driven by a function generator (Agilent, Palo Alto, Calif.) through a 50-dB power amplifier (E&I, Rochester, N.Y.) (for example as shown in FIG. 5). A central-void (radius: 11.2 mm) of the therapeutic transducer held a pulse-echo ultrasound transducer (center frequency: 10 MHz, focal length: 60 mm), which was used for imaging, with their two foci aligned. The imaging transducer was driven by a pulser-receiver (Olympus, Waltham, Mass.) connected to a digitizer (Gage Applied Technologies, Lachine, QC, Canada). A cone filled with degassed and distilled water was mounted onto the transducer system and was fitted with a polyurethane membrane (Trojan; Church & Dwight Co., Princeton, N.J.). The transducers were attached to a computer-controlled 3D positioning system (Velmex, Lachine, QC, Canada). The targeting procedure has been described herein. For example, the FUS transducer was moved 3 mm laterally of the sagittal suture and 2 mm anterior of the lambdoid suture. A needle hydrophone (Precision Acoustics, Dorchester, Dorset, UK, needle diameter: 0.2 mm) was used to measure the three-dimensional pressure field in a degassed water-tank prior to the in vivo application. The FUS focal spot overlapped with the right hippocampus and the latter portion of the thalamus, since the axial and lateral full-widths at half-maximum intensities of the beam were 7.5 mm and 1 mm, respectively. The left hippocampus fissure was used as a control, and was not sonicated. Pulsed FUS was emitted for 60 s, with a burst rate of 10 Hz, 100 burst cycles, at acoustic pressures adjusted to correspond to 0.30, 0.45, and 0.60 MPa (peak-rarefractional), after accounting for 18% murine skull attenuation. These pressures were obtained experimentally in degassed water. The mice were anesthetized using 1.25-2.50% isoflurane (SurgiVet, Smiths Medical PM, Wisconsin) mixed with oxygen during FUS.

Size Isolated Microbubbles

The microbubbles used were size-isolated from a polydispersed microbubble distribution using differential centrifugation. The bubbles had a 1,2-disearoyl-sn-glycero-3-phosphocholine (DSPC) and polyoxyethylene-40 stearate (PEG40S) lipid shell and perfluorobutane (PFB) core. After the centrifugation and resuspension processes were repeated several times, three desired ranges of 1-2, 4-5, and 6-8 mm in diameter were isolated. A bolus of 1 mL/g at a concentration of $8 \times 10^8$/mL was injected intravenously through the tail vein prior to sonication.

Magnetic Resonance Imaging

BBB opening in the murine hippocampus was confirmed using a 9.4 T system (Bruker Medical; Boston, Mass.). All mice were anesthetized orally using 1-2% of isoflurane mixed with oxygen and were placed inside the vertical-bore, having a fixed position in a plastic tube with a 3.0 cm diameter birdcage coil. Vital signals were monitored and respiration rate was approximately 55 breaths/min. Each MRI session included a pre and a postcontrast enhancement, T1-weighted 2D FLASH acquisition (TR/TE: 230/3.3 ms, flip angle: 70°, NEX: 18, resolution 86 mm×86 mm, slice thickness: 500 mm, 23 slices, F.O.V.: 22 mm×16.5 mm, matrix size 256×192, receiver bandwidth: 50 kHz), obtained respectively 15 min after sonication and 55 min after injection of the MRI contrast agent (Gd-DTPA-BMA). Signal enhancement in the area of the sonicated hippocampus reached a peak approximately 1 h after IP injection. Therefore, the CE-T1 images were acquired 55 min following the injection. Omniscan™ (Gd-DTPA-BMA) was used to enhance the MR contrast in the murine brain, as a tracer for the BBB opening since it can diffuse into the brain parenchyma following BBB's altered permeability in the targeted area. Gd-DTPA-BMA was administered intraperitoneally (IP) at a dose of 6 mmol/kg. An IP bolus can provide more temporally consistent and sustained MR enhancement than an IV bolus and can be logistically simpler. Preliminary work on the IP bolus dosage indicated that the 6 mmol/kg can avoid the signal decrease which can be observed when, due to excessive Gd-DTPA-BMA, the T2 relaxivity dominates the T1 relaxivity. The same MRI session was repeated daily starting from the day of the BBB opening (day 0) and lasting up to 5 days. In the five cases where signal enhancement was detected on day 5, MRI sessions were repeated on day 7.

Animal Preparation

All procedures used in this study involving animals were approved by the Columbia University Institutional Animal Care and Use Committee. A total of forty-two (n=42) wild-type mice, (strain C57BL/6, mass: 20-25 g, sex: male, Harlan, Indianapolis, Ind.) was used for this experiment, separated into ten groups. Each mouse in the first nine groups was sonicated with a different combination of PRP, i.e., 0.30, 0.45, or 0.60 MPa, and a microbubble diameter, i.e., 1-2, 4-5, or 6-8 mm. These mice underwent MRI for several days after FUS. A sham group had three (n=3) mice, for which the whole procedure was repeated without FUS, i.e., anesthesia, injection of microbubbles, and MRI sessions for up to 5 days.

Histology and Imaging

On day 7, all mice were euthanized and transcardially perfused with 30 mL PBS and 60 mL 4% paraformaldehyde. Brains were soaked in paraformaldehyde for 24 h. Skulls were removed, and the brains were fixed again in 4% paraformaldehyde for 6 days, followed by conventional postfixation procedures. The paraffin-embedded specimens were sectioned horizontally at a thickness of 6 mm. 24 sections were stained and examined for each brain. Sections were stained with hematoxylin and eosin and then examined for red blood cell extravasations into the brain parenchyma as well as cell loss.

Image Processing and Volumetric Measurements

The enhancement in CE-T1 MR images was quantified in elliptic cylindrical VOIs encompassing the hippocampal formation, at two contralateral regions, in the right (sonicated) and the left (control) hemisphere, on each brain for each day. The major diameter of the elliptic cylinders was 4.3 mm, the minor diameter 3.4 mm, and the height 4.5 mm, covering an area of approximately 14,000 voxels from a total of nine consecutive horizontal slices, on each side. Therefore, the total volume on each cylinder was 52 mm$^3$. In order to quantify the BBB opening volume at the sonicated side, an intensity threshold was determined and the contrast-enhanced pixels in the vessels and ventricles were excluded. To address these issues, the signal intensity was averaged over a small circular region of 1 mm in diameter, centered around the nonsonicated contralateral side close to the hippocampus and used as a reference. The number of voxels in the right (sonicated) and left (control) VOI at an intensity of 2.5 standard deviations (S.D.) or above the reference were counted. The total number of these voxels in the left VOI was then subtracted from the respective total number of voxels in the right VOI, to exclude volume contrast-enhancement in the vessels and ventricles. Precontrast images were used for the detection of any hyperintense areas before Gd-DTPA-BMA injection, and were not coregistered with the postcontrast.

The measurements in the sham group were used as the baseline, denoting that the integrity of the BBB was fully restored. Following the calculation of the mean and standard deviation (S.D.) of the volumetric measurements for each group, i.e., mice sonicated at the same PRP and microbubble size, a two-tailed Student's t-test was performed, and if no statistically significant difference compared to the control baseline was observed ($P>0.05$), then the BBB was considered to have closed. In other words, the closing criterion was checked on each day for each group and not for each measurement individually. All groups met the closing criterion by day 5. For the five individual cases where signal enhancement was shown on day 5, MRI was repeated on day 7. Not all of these cases however belonged to the same group, and the groups they belonged to could still meet the closing criterion based on the statistical analysis.

In order to show the differences in the timeline for closing between microbubble sizes and pressures, a statistical analysis was performed on the volume of diffusion of Gd-DTPA-BMA on day 0. To evaluate the effect of the microbubble size, a two-tailed Student's t-test was performed for each PRP, i.e., between 1-2 mm and 4-5 mm, between 1-2 mm and 6-8 mm, as well as between 4-5 mm and 6-8 mm. Differences between the different groups regarding the volume of BBB opening and the time required for the opened BBB to be reinstated were examined.

Results

Figure 18:
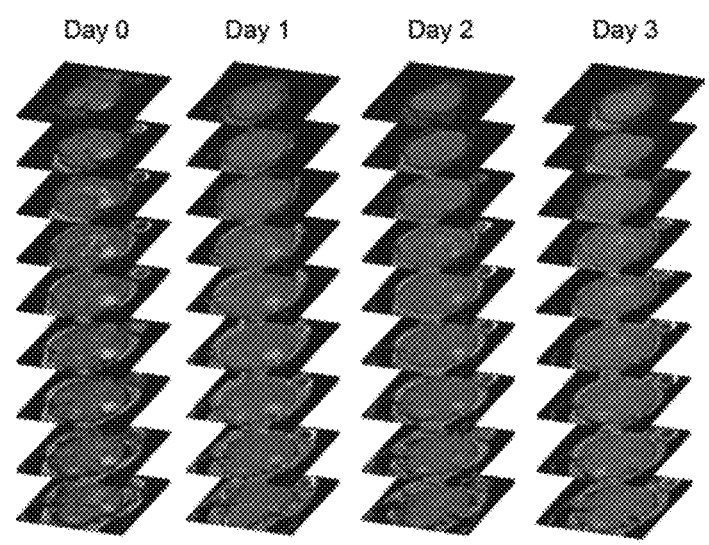
FIG. 18 illustrates images of a mouse brain subjected to sonication in accordance with an exemplary embodiment of the disclosed subject matter.

FIG. 18 shows horizontal consecutive CE-T1 images (500 mm thickness, dorsal on top, ventral on bottom) from day 0 to 3 for a 6-8 mm/0.30 MPa case. The BBB opening reduced radially towards the center of the FUS beam over time, until closing was detected in day 3, when no Gd-DTPA-BMA diffused from the vasculature to the brain parenchyma.

An example of the volume quantification can be shown in FIG. 18. The VOIs were manually traced to overlap with the right and left hippocampi. On both sides, voxels with an intensity 2.5 S.D. or above the reference intensity are overlaid in red. As shown in these images, when there is no diffusion of Gd-DPTA-BMA from the vasculature to the brain parenchyma, e.g., on the control side, the vessels and the ventricles can have CE-T1 intensity above the threshold. However, when the permeability of the BBB is altered on the right hippocampus as a result of the FUS, Gd-DTPA-BMA can diffuse in that region and the area of opening can be overlaid in red. The example in FIG. 18 shows the same brain in multiple 2D slices where 6-8-mm bubbles at a PRP of 0.30 MPa were used. The volume of opening was reduced radially towards the focal region over several subsequent days, until no trans-BBB diffusion was detected on day 3, signifying that the BBB was successfully reinstated.

Figure 19:
FIG. 19 illustrates images of microbubbles in accordance with an exemplary embodiment of the disclosed subject matter.
Figure 20A:
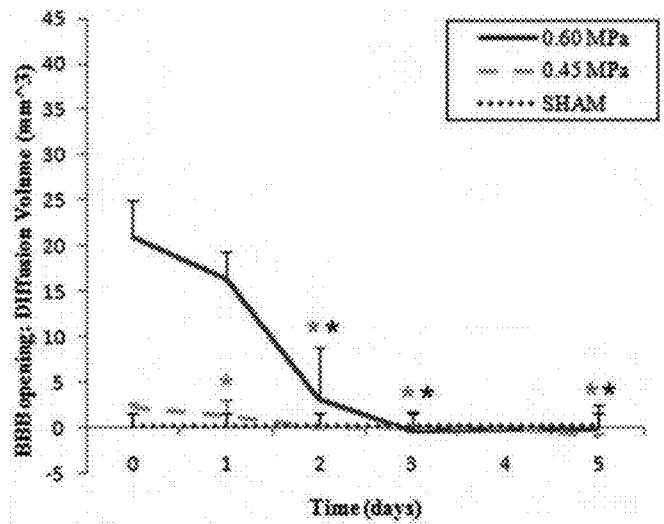
FIGS. 20A-20C are diagrams illustrating further features of the disclosed subject matter.
Figure 20B:
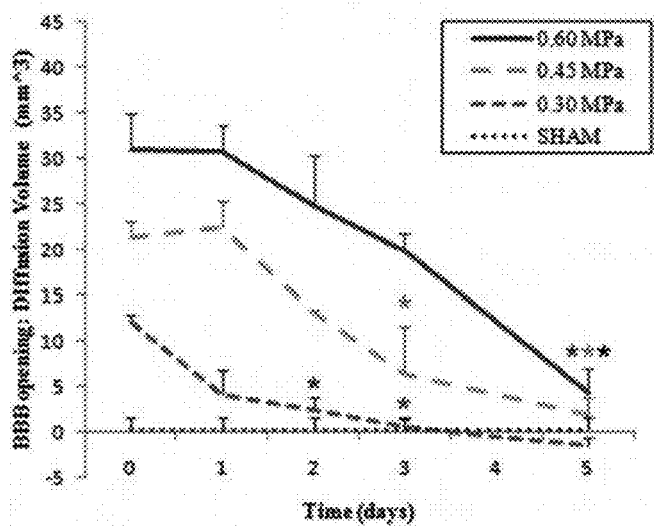
Figure 20C:
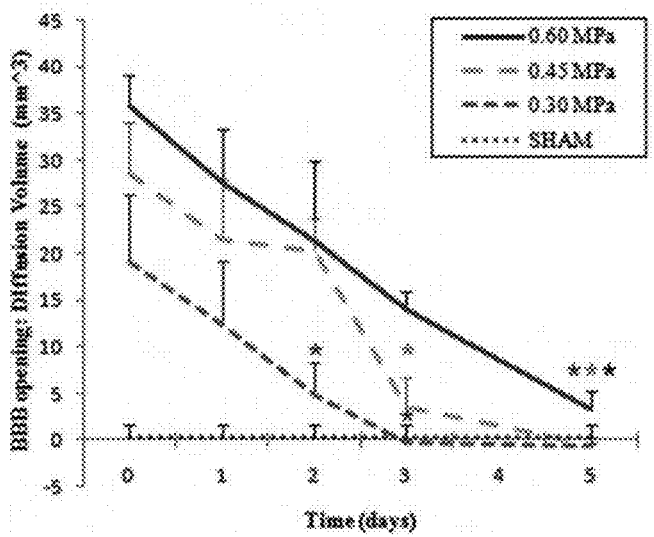
Figure 21:
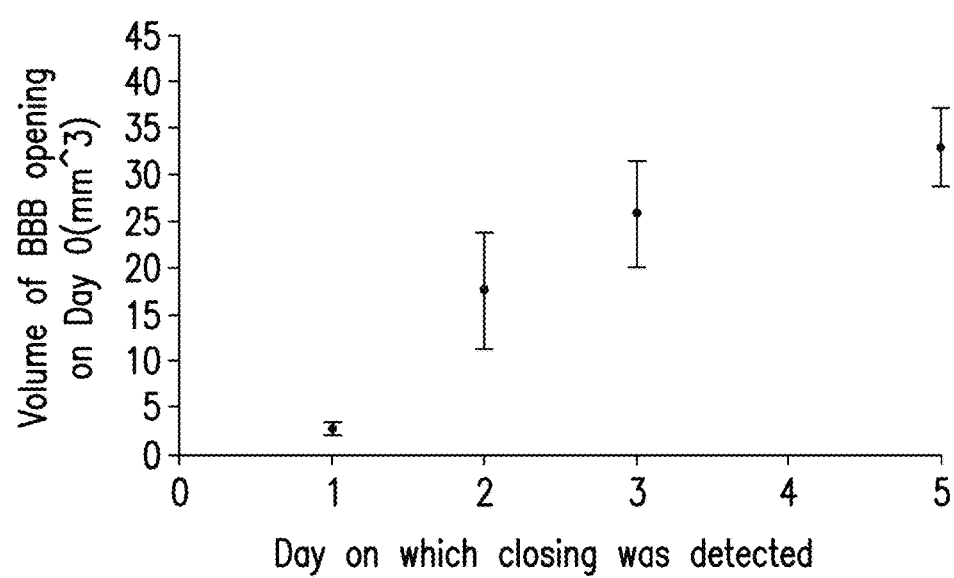
FIG. 21 is a diagram illustrating further features of the disclosed subject matter.

FIG. 19 shows coronal reconstructions from horizontal CE-T1 images with one example provided in each case of PRP and microbubble size. FIGS. 20A-20C show volume of diffusion of Gd-DTPA-BMA area, depicting BBB opening, for PRP of 0.30, 0.45, and 0.60 MPa and the sham group with microbubbles of 1-2 mm in FIG. 20A, 4-5 mm in FIG. 20B, and 6-8 mm in FIG. 20C in diameter. Error bars correspond to standard deviation and (*) denotes closing. FIG. 21 shows volume of BBB opening on day 0 versus time to closing, showing that the duration of BBB opening increased monotonically with the volume of opening on day 0.

For all cases of microbubble sizes and pressures studied, the BBB was found to be reinstated by day 5, and the duration of opening depended on the microbubble diameter and PRP used. In FIG. 19, reconstructions of the horizontal planes, sliced coronally at the level of the hippocampal formation, at all pressures and microbubble sizes are shown. In FIG. 19, it can also be shown that the area of Gd-DTPA-BMA diffusion in the brain and its spatial characteristics can depend on the microbubble size and pressure used. The BBB permeability to Gd-DTPA-BMA can occur dorsally in the brain in the cases when larger microbubbles were used, i.e., not in the 1-2 mm case, where diffusion of the contrast agent Gd-DTPA-BMA was observed mainly ventrally in the brain near the vasculature. This effect can be shown further at higher PRPs, i.e., 0.60 MPa. Volumetric measurements are shown in FIGS. 20A-20C for the 1-2, 4-5, and 6-8 mm microbubble cases. At 0.30 MPa with the 1-2 mm microbubbles no BBB opening was detected. Depending on the microbubble and pressure used, the BBB closing occurred within 24 h and 5 days after sonication. More specifically, with the 1-2 mm microbubbles (FIG. 20A), closing was found to be closed on day 1 and 2 at 0.45 and 0.60 MPa, respectively. With the 4-5 mm and 6-8 mm microbubbles, the BBB was found to be closed on day 2 at 0.30 MPa, day 3 at 0.45 MPa, and day 5 at 0.60 MPa. A proportional relationship between the volume and the duration of the BBB opening regardless of the PPR and microbubble size used to induce the opening can thus be shown (for example in FIG. 21). Linear regression can show a correlation of R2=0.72. Excluding day 0 a logarithmic fit indicated a correlation of R2=0.78.

The results of the statistical analysis on day 0 are shown in Table 4. At 0.30 MPa, opening was induced only in the 4-5 and 6-8 mm cases, without statistically significant difference (P>0.05) between these two diameter ranges (Table 4), and the BBB was restored by day 2 in both cases. At 0.45 MPa, the volume of BBB opening induced with 1-2 mm microbubbles, was statistically different (P<0.01) than that with larger microbubbles (Table 4), and occurred within 24 h, compared to 2-3 days needed in the cases of the larger microbubbles. Finally, in Table 4, it can be shown that at 0.60 MPa, there was a statistically significant difference between the 1-2-mm and 6-8-mm bubbles (P<0.05), and at least 2 days were required for the BBB to be reinstated in the 1-2 mm case, as opposed to 4-5 days required for the larger microbubbles.

FIGS. 22A-22D show examples of one out of the five cases where damage was detected. FIGS. 22A-22B are horizontal precontrast T1-weighted images, acquired on day 0 and 7, respectively. Hyperintensity can be shown (white arrows) on the sonicated side, more enhanced on day 7. FIGS. 22C-22D are the H&E stained slices, magnified (10) at the left (control) hippocampus and at the right (sonicated) hippocampus, respectively. In FIG. 22C cell loss can be detected at the dentate gyrus and CA1 area (white arrows).

Correlation can also be found between all histological damage cases and hyperintensity in the precontrast T1-w images. An example is shown in FIGS. 22A-22D, where hyperintensity was detected at the sonicated region in the precontrast image, and cell loss was detected on the H&E stained slices at the level of the hippocampus. Damage was observed upon histological examination only in five animals, approximately 13% of the total number of animals used, all of which were at higher PRPs.

Discussion

In this Example, the reversibility of BBB opening was investigated using Gd-DTPA-BMA that cannot cross the BBB when the BBB is reinstated or closed. Spatial (i.e., volume) and temporal (i.e., duration) characteristics of the intact or BBB's altered function were analyzed, while opening was induced using three different microbubble sizes and three different PRPs. BBB opening induced by FUS can be shown to be transient, but the duration can depend on the acoustic parameters and bubbles used. Also, the BBB opening can be dependent on the acoustic pressure used as well as the microbubble size. The features of the BBB self-repairing characteristic were analyzed under a combination of different acoustic parameters, and a range of mono-dispersed microbubbles. A proportional relationship between the BBB opening volume and the time required for closing can be shown. Therefore, both the BBB opening volume and duration was shown to be dependent on the acoustic pressure and the microbubble size used.

The spatial characteristics of the BBB opening and its reversibility was shown as follows. Firstly, as seen in the examples of FIGS. 18 and 19, the BBB function can be reinstated in a reverse direction to that of the diffusion after opening, i.e., closing starts from the outer opened regions and ends at the focal region while also being dependent on the hippocampal vasculature. It was also shown that the permeability values towards the center of the focal region were higher. The peak of the acoustic pressure distribution can lie at the center of the focal spot which can result in larger BBB openings, hence taking longer to close. Additionally or alternatively, where the vasculature is denser, there can be a higher number of opening sites, and thus longer timelines for closing to be completed.

Even though the volume of opening induced by the 6-8-mm bubbles can be greater than the volume induced by the 4-5 mm microbubbles, these two micro-bubble sizes did not differ significantly in this experiment (as shown in Table 4) and the days required for closing were also similar (FIGS. 20B-20C). The differences can be relatively small because both 4-5-mm and 6-8-mm bubbles can be within the diameter size range of the capillary, i.e., 4-8 mm, and therefore they can both be in contact with the capillary wall, exerting forces on it while being acoustically driven. However, the mechanical stress on the capillary walls due to the acoustically driven microbubbles for a specific pressure when induced by the 6-8-mm can be larger than when induced by the 4-5-mm bubbles, because higher PRP can reach a similar size expansion as the 6-8-mm and have a similar effect, hence the BBB opening volume can be increased.

TABLE 4

Statistical Significance of the Volume of Diffusion of Gd-DTPA¬BMA on Day 0, Comparing Different Cases of Microbubble Diameters per PRP

| Day 0 | | 1-2 (μM) | 4-6 (μM) |
|---|---|---|---|
| 0.30 MPa | 6-8 μM | — | P > 0.05 |
| 0.45 MPa | 6-8 μM | P < 0.01 | P > 0.05 |
|  | 4-5 μM | P < 0.01 | — |
| 0.60 MPa | 6-8 μM | P < 0.05 | P > 0.05 |
|  | 4-5 μM | P > 0.05 | — |

The BBB opening volume using 1-2-mm bubbles can be lower than for the larger microbubbles, (Table 4) and the BBB can close faster. Therefore, for improved BBB recovery at high pressures, smaller microbubbles can be preferable. The relative expansion of a microbubble can be inversely proportional to its resting diameter. 1-2-mm bubbles can induce no opening at 0.30 MPa, where only stable cavitation is expected. Thus, stable oscillations of smaller microbubbles can be insufficient to induce the repeated stress against the capillary wall at 0.30 MPa, but can be adequate at 0.45 MPa, and even more so at 0.60 MPa. It can also be shown that fragmentation occurs more frequently for microbubbles with a relatively small rather than a large resting diameter at a threshold size of 2.5 mm. Below that level, fragmentation may occur and bubbles smaller than 2 mm can be fragmented prior to reaching the endothelium and not interact with the vessel wall. Therefore, it was shown that the smaller microbubbles can be incapable of inducing opening in sites away from the bigger vessels, because they can undergo fragmentation at the beginning of the FUS pulse before perfusing the microvasculature. And thus, the therapeutic efficacy of 1-2 mm bubbles in the capillaries may be decreased.

The timeline for closing can be longer than 3-24 h. This can be due to multiple factors. First, the microbubble formulation used in this Example could be different than the commercially available contrast agents, in terms of the combination of shell properties, gas core and diameter size; therefore, this microbubble formulation used here can be a parameter to induce variations. However, the size range of the commercially available microbubbles can be closer to the 1-2-mm bubbles used in this experiment, which were shown to induce BBB opening that can close within 24 h.

At lower PRPs, the BBB can close relatively faster, and the PRPs used can be below 0.50 MPa. Moreover, the FUS frequency (1.5 MHz) can affect closing time. The resonance frequency can decrease with the microbubble radius, and can also decrease with decreasing microvessel radius. Therefore, using a lower frequency for example, which can be closer to the resonance frequency of the micro-bubbles within the microvessles and capillaries, the aforementioned effects can be further enhanced. Finally, the agents used to cross the BBB for the detection of opening can have larger MWs (Magnevist®: 938 Da, HRP: 40 kDa, Evans Blue: 961 Da) while it was shown that the BBB becomes less permeable at higher MWs. Since the administered Gd-DTPA-BMA can be a relatively smaller (574 Da) agent and above the size threshold to cross the BBB (400 Da), the disclosed subject matter can have an increased sensitivity regarding the detection of BBB opening, which can contribute to longer closing times.

In the five cases where cell loss was detected in the H&E stained brain sections on the sonicated region, hyperintensity was also detected on the precontrast MRI images at the corresponding regions. The signal enhancement detected in these areas in the precontrast T1-w images can be due to permanent damage, blood present in the brain or arrested Gd-DTPA-BMA in damaged vasculature, and thus BBB can not be completely restored.

The BBB remained opened over several days in some cases. It was thereafter restored and 87% of the cases showed no detectable damage, while the remaining 13% showed minimal cell loss. Thus, first, at shorter burst lengths opening can be induced with less damage, and second, the self-repairing mechanism of the BBB can restore certain types of injury induced to the brain after FUS.

BBB can be disrupted longer than the MRI system used can detect and the resolution of the images can acquire. Additionally, the first acquisition or postcontrast T1-w images can be 1 h after FUS, and within this time some cases with relatively small BBB opening can be undetected. Finally, the circulation times and persistence of all the different sizes of microbubbles can be similar for the 10-20 s interval between injection and FUS, however, differences can affect the results.

In this Example, the volume of BBB opening and the time required for the BBB to be reinstated depends on the microbubble size and the acoustic pressure. In addition, the time for closing is proportional to the volume of opening induced by FUS, and BBB can recover its functionality between 24 h and 5 days after. The BBB opening volume can decrease radially towards the center of the focal spot over time. At lower acoustic pressures, relatively smaller microbubble diameters can induce a lower volume of BBB opening, and the closing timeline can be different than that using larger microbubbles. As the PRP increases, the differences in BBB opening and closing between the different microbubble sizes can be reduced. The BBB can close relatively faster when small microbubbles are used, while for the 4-5 and 6-8 mm the same duration for closing can be shown. Finally, hyperintensity in the area of BBB opening can be detected in the precontrast MR images in the cases where damage was concluded in histology. The FUS-opened BBB self-repairing characteristics can be shown, spatially and temporally, and the systems and methods described herein can be adjusted according to the pharmacokinetic needs of administered CNS drugs.

It will be understood that the foregoing is only illustrative of the principles described herein, and that various modifications can be made by those skilled in the art without departing from the scope and spirit of the disclosed subject matter. For example, the system and methods described herein are used for opening the blood-brain barrier of a subject. It is understood that that techniques described herein are useful for opening of other tissues. Further, the techniques described have been performed on mice but it is understood the techniques are applicable to other subject, such as humans. Moreover, features of embodiments described herein can be combined and/or rearranged to create new embodiments.

We claim:

1. A method for opening a tissue to a target value using microbubbles, comprising:
    targeting a region of the tissue to open;
    determining at least one acoustic parameter corresponding to the target value, the at least one acoustic parameter is selected to control one or more acoustic cavitation events to open the tissue to the target value to thereby allow passage of molecules and/or agents; and
    applying an ultrasound beam at the at least one acoustic parameter to the targeted region such that the tissue is opened with the microbubbles to the target value.

2. The method of claim 1, further comprising positioning the microbubbles in proximity to the targeted region, wherein positioning the microbubbles comprises performing at least one injection of the microbubbles such that the microbubbles are positioned proximate to the targeted region.

3. The method of claim 2, further comprising determining at least one of a number of injections of the microbubbles corresponding to the target value and a duration of injection of the microbubbles corresponding to the target value.

4. The method of claim 2, wherein the at least one injection comprises at least one of a systemic injection, a bolus injection and a slow diffusion injection.

5. The method of claim 1, wherein controlling the one or more acoustic cavitation events comprises controlling a magnitude, a type or a number of the one or more acoustic cavitation events.

6. The method of claim 1, wherein the acoustic parameter is selected from at least one of a pulse length, a pulse repetition frequency, a burst length, and a burst repetition frequency.

7. The method of claim 1, wherein determining at least one acoustic parameter further comprises determining at least one of a frequency, a duration and a pressure range corresponding to the target value.

8. The method of claim 7, wherein the at least one acoustic parameter comprises the pressure range, and wherein the pressure range corresponds to a resonance frequency of the microbubbles proximate to the targeted region.

9. The method of claim 1, further comprising determining a concentration range of microbubbles corresponding to the target value prior to the positioning of the microbubbles.

10. The method of claim 1, wherein the tissue comprises at least one of a vessel, a cell and a blood-brain barrier.

11. The method of claim 1, further comprising applying an ultrasound beam to move the microbubbles into vessels of the tissue.

12. The method of claim 1, wherein the microbubbles comprise at least one of acoustically activated microbubbles, molecule carrying microbubbles and microbubbles having a size range between 1 and 10 microns.

13. The method of claim 12, wherein the microbubbles comprises the molecule-carrying microbubbles, and wherein the molecule comprises at least one of a medicinal molecule, a contrast agent, a biomarker and a liposome.

14. The method of claim 1, further comprising positioning at least one of a medicinal molecule and a contrast agent in proximity to the targeted region.

15. The method of claim 1, further comprising imaging the targeted region to form an image of the opened tissue, wherein imaging the targeted region comprises applying an ultrasound beam to the targeted region, utilizing a magnetic resonance imaging device to image the targeted region, or utilizing a fluorescence imaging device to image the targeted region.

16. The method of claim 1, wherein at least a portion of the opened tissue closes, and the method further comprises imaging the targeted region to form an image of the closed tissue.

17. The method of claim 16, further comprising reopening at least a portion of the closed tissue.

18. The method of claim 1, wherein the target value comprises a target size of an opening of the tissue.

19. The method of claim 1, wherein the target value comprises a target rate at which molecules pass through the tissue.

20. The method of claim 1, wherein the at least one acoustic parameter is selected to open the tissue to the target value using the controlled type of the one or more acoustic cavitation events.

21. The method of claim 20, wherein the controlled type of the one or more acoustic cavitation events comprises at least one of stable cavitation and inertial cavitation.

22. A system for opening a tissue to a target value using a solution of microbubbles having size range corresponding to the target value, comprising:
a targeting assembly for targeting a region of the tissue;
an introducer for delivering the solution to a location proximate to the targeted region; and
a transducer, coupled to the targeting assembly, for applying an ultrasound beam to the targeted region at least one acoustic parameter corresponding to the target value thereby opening the tissue with the microbubbles to the target value, wherein the at least one acoustic parameter is selected to control one or more acoustic cavitation events to open the tissue to the target value to thereby allow passage of molecules and/or agents.

23. The system of claim 22, wherein the target value corresponds to an imaging value to allow passage of certain molecules and/or agents.

24. The system of claim 22, wherein the targeting assembly comprises at least one of an ultrasound transducer and one or more members for placement on an anatomical landmark of the tissue, and
wherein the system further comprises an imaging device for capturing image data of the opened tissue of the targeted region, and a processor, operatively coupled to the imaging device, for processing the image data to form an image therefrom.

25. The system of claim 22, wherein the solution of microbubbles further comprises a microbubbles concentration range corresponding to the target value.

26. A method for delivering a drug across a tissue, comprising opening a tissue to a target value using microbubbles, comprising:
targeting a region of the tissue to open;
determining at least one acoustic parameter corresponding to the target value, wherein the at least one acoustic parameter is selected to control one or more acoustic cavitation events to open the tissue to the target value to thereby allow passage of molecules and/or agents;
applying an ultrasound beam at the at least one acoustic parameter to the targeted region such that the tissue is opened with the microbubbles to the target value; and
injecting the drug into the tissue in proximity to the opening.

27. The method of claim 26, wherein the tissue comprises a blood-brain barrier.

28. A method for opening a tissue for a target duration of time using microbubbles, comprising:
targeting a region of the tissue to open;
selecting microbubbles having at least one microbubble parameter corresponding to the target duration of time, wherein the at least one microbubble parameter is selected to control one or more acoustic cavitation events to open the tissue for the target duration of time to thereby allow passage of molecules and/or agents; and
applying an ultrasound beam to the targeted region such that the tissue is opened with the microbubbles for the target duration of time.

29. The method of claim 28, wherein the at least one microbubble parameter comprises a microbubble size.

30. The method of claim 28, further comprising selecting at least one acoustic parameter and applying the ultrasound beam at the at least one acoustic parameter, wherein the at least one acoustic parameter is selected to further control a magnitude, a type, or a number of the one or more acoustic cavitation events to open the tissue for the target duration of time.

* * * * *